US009067181B2

(12) United States Patent
Rybtchinski et al.

(10) Patent No.: US 9,067,181 B2
(45) Date of Patent: Jun. 30, 2015

(54) SEPARATION OF NANOPARTICLES

(71) Applicant: YEDA RESEARCH AND DEVELOPMENT CO.LTD, Reovot (IL)

(72) Inventors: Boris Rybtchinski, Givatayyim (IL); Elisha M. Krieg, Rehovot (IL); Haim Weissman, Rehovot (IL); Shira Albeck, Rehovot (IL); Yaron Tidhar, Rehovot (IL)

(73) Assignee: YEDA RESEARCH AND DEVELOPMENT CO. LTD., Rehovot, IL (US)

( * ) Notice: Subject to any disclaimer, the term of this patent is extended or adjusted under 35 U.S.C. 154(b) by 73 days.

(21) Appl. No.: 13/779,248

(22) Filed: Feb. 27, 2013

(65) Prior Publication Data

US 2013/0303769 A1 Nov. 14, 2013

Related U.S. Application Data

(63) Continuation-in-part of application No. PCT/IL2011/000687, filed on Aug. 25, 2011.

(60) Provisional application No. 61/377,540, filed on Aug. 27, 2010.

(51) Int. Cl.
| | |
|---|---|
| *C08G 73/06* | (2006.01) |
| *C07D 471/08* | (2006.01) |
| *B01D 71/64* | (2006.01) |
| *B01D 65/02* | (2006.01) |
| *B01D 69/14* | (2006.01) |
| *C08G 73/10* | (2006.01) |
| *C08J 5/22* | (2006.01) |
| *C08G 65/333* | (2006.01) |
| *C07F 1/12* | (2006.01) |
| *C07F 3/08* | (2006.01) |
| *C08L 65/00* | (2006.01) |

(52) U.S. Cl.
CPC .............. *B01D 71/64* (2013.01); *B01D 65/02* (2013.01); *B01D 69/14* (2013.01); *C08G 73/10* (2013.01); *C08G 73/1046* (2013.01); *C08J 5/2256* (2013.01); *C08G 65/33396* (2013.01); *C07F 1/12* (2013.01); *C07F 3/08* (2013.01); *C08G 2261/415* (2013.01); *C08L 65/00* (2013.01); *C08G 2261/344* (2013.01)

(58) Field of Classification Search
USPC ............................................ 528/423; 546/37
See application file for complete search history.

(56) References Cited

U.S. PATENT DOCUMENTS

| | | | |
|---|---|---|---|
| 6,143,905 A | 11/2000 | Böhm et al. | |
| 6,184,378 B1 | 2/2001 | Böhm et al. | |
| 6,326,494 B1 | 12/2001 | Böhm et al. | |
| 2005/0176970 A1 | 8/2005 | Marks et al. | |
| 2007/0202353 A1 | 8/2007 | Inagaki et al. | |
| 2011/0137008 A1 | 6/2011 | Yeh et al. | |

FOREIGN PATENT DOCUMENTS

| | | |
|---|---|---|
| CN | 1706842 | 5/2005 |
| CN | 101157757 A | 4/2008 |
| EP | 0422535 A1 | 4/1991 |
| WO | WO 97/22607 | 6/1997 |
| WO | WO 02/14318 A1 | 2/2002 |
| WO | WO 02/14414 A3 | 2/2002 |
| WO | WO 2005/124453 A2 | 12/2005 |
| WO | WO 2008/139452 A3 | 11/2008 |
| WO | WO 2009/118742 | 10/2009 |

OTHER PUBLICATIONS

Addicott et al. "Synthesis of a bis(pyridyl)-substituted perylene diimide ligand and incorporation into a supramolecular rhomboid and rectangle via coordination driven self-assembly" J Org Chem. ;70(3):797-801, Feb. 4, 2005.

Ahrens et al.; "Self-Assembly of Supramolecular Light-Harvesting Arrays from Covalent Multi-Chromophore Perylene-3,4:9,10-bis(dicarboximide) Building Blocks", J. Am. Chem. Soc. 2004, 126, 8284-8294.

Aprahamian; "Anions and Polyanions of Oligoindenopyrenes: Modes of Electron Delocalization and Dimerization", Chem. Asian J. 2006, 1, 678-685.

Baram et al.; "Control over Self-Assembly through Reversible Charging of the Aromatic Building Blocks in Photofunctional Supramolecular Fibers", J. Am. Chem. Soc. 2008, 130, 14966-14967.

Becke; "Density-functional thermochemistry. III. The role of exact exchange," J. Chem. Phys.98 (7), pp. 5648-5652, (1993).

Beggin; "Supramolecular Templates as Porogenes", Adv. Mater. 1998, 10, 1391-1394.

Benfer et al.; "Ceramic Membranes for Filtration Applications—Preparation and Characterization", Eng. Mater. 2004, 6, 495-500.

Bhattacharjee et al.; "Studies on the fractionation of β-lactoglobulin from casein whey using ultrafiltration and ion-exchange membrane chromatography", J. Membr. Sci. 2006, 275, 141-150.

Binsilong et al.; "Synthesis and Structure of a Novel Silver(1) Perchlorate 2,2':6',2"-Terpyridine Adduct Solvated with Acetonitrile", Aust. J. Chem. 1994, 47, 1545-1551.

Breeze et al. "Polymer—perylene diimide heterojunction solar cells," Appl. Phys. Lett., 81, 3085, (2002).

Brust; "Synthesis of thiol-derivatised gold nanoparticles in a two-phase Liquid-Liquid system", J. Chem. Soc., Chem. Commun., 801 (1994).

(Continued)

*Primary Examiner* — Charanjit Aulakh
(74) *Attorney, Agent, or Firm* — Pearl Cohen Zedek Latzer Baratz LLP; Mark S. Cohen

(57) ABSTRACT

This invention is directed to separation, optimization and purification of nano-materials using self-assembled perylene diimide membranes, wherein said perylene diimide membrane is recyclable.

26 Claims, 42 Drawing Sheets

(56) References Cited

OTHER PUBLICATIONS

Busbee et al.; "An Improved Synthesis of High-Aspect-Ratio Gold Nanorods", Adv. Mater.15, 414 (2003).
Che et al.; "Ultralong Nanobelts Self-Assembled from an Asymmetric Perylene Tetracarboxylic Diimide", J. Am. Chem. Soc. 2007, 129, 7234-7235.
Chen et al.; "Self-assembled π-stacks of functional dyes in solution: structural and thermodynamic features", Chem. Soc. Rev. 2009, 38, 564-584.
Cohen et al.; "The Charge Alternation Concept: Application to Cyclic Conjugated Doubly Charged Systems", J. Am. Chem. Soc. 1988, 110, 4634-4640.
Corbin et al.; "Self-Association without Regard to Prototropy. A Heterocycle That Forms Extremely Stable Quadruply Hydrogen-Bonded Dimers", J. Am. Chem. Soc. 1998, 120, 9710-9711.
Cui et al.; "Block Copolymer Assembly via Kinetic Control", Science 2007, 317, 647-650.
Dalsin et al.; "Protein Resistance of Titanium Oxide Surfaces Modified by Biologically Inspired mPEG-DOPA", Langmuir 2004, 21, 640-646.
Demmig et al. "Easily soluble and photostable perylene fluorescent dyes," Chemische Berichte, vol. 121 Issue 2, pp. 225-230, (1988).
Dimitrakopoulos et al. "Organic thin film transistors for large area electronics," Advanced Materials, 14, pp. 99-117, (2002).
Dreiss; "Wormlike micelles: where do we stand? Recent developments, linear rheology and scattering techniques", Soft Matter 2007, 3, 956-970.
Ebeid et al. "Emission characteristics and photostability of N, N'-bis (2, 5-di-tert-butylphenyl)-3, 4:9, 10- perylenebis (dicarboximide)," Journal of physical chemistry, vol. 92, No. 15, pp. 4565-4568, (1988).
Ego et al.; "Attaching perylene dyes to polyfluorene: three simple, efficient methods for facile color tuning of light-emitting polymers" J. Am. Chem. Soc, 125, 437, (2003).
Fan et al. "1,6-Disubstituted perylene bisimides: concise synthesis and characterization as near-infrared fluorescent dyes," Tetrahedron Letters, vol. 46, Issue 26, pp. 4443-4447, Jun. 27, 2005.
Ford et al.; "Photochemistry of 3,4,9,10-perylenetetracarboxylic dianhydride dyes. 4. Spectroscopic and redox properties of oxidized and reduced forms of the bis(2,5-di-tert-butylphenyl)imide derivative" J. Phys. Chem., 93 (18), pp. 6692-6696, (1989).
Fox; "The Photoexcited States of Organic Anions", Chem. Rev. 1979, 79, 253-273.
Frim et al.; "Helicene Dianions : Paratropicity of Twisted Phenanthrene Dianions", Chem. Int. Ed. 1990, 29, 919-921.
Gibb; "Supramolecular Assembly and Binding in Aqueous Solution: Useful Tips Regarding the Hofmeister and Hydrophobic Effects", Isr. J. Chem. 2011, 51, 798-806.
Golubkov et al.; "Economical Design in Noncovalent Nanoscale Synthesis: Diverse Photofunctional Nanostructures Based on a Single Covalent Building Block", Angew. Chem. Int. Ed. 2009, 48, 926-930, Jan. 7, 2009.
Gosztola; "Excited Doublet States of Electrochemically Generated Aromatic Imide and Diimide Radical Anions", J. Phys. Chem. A 2000, 104, 6545-6551.
Holy; "Reactions of the Radical Anions and Dianions of Aromatic Hydrocarbons", N. L., Chem. Rev. 1974, 74, 243-277.
Huber et al.; "Effects of Electron-Transfer Processes on Conformation", Acc. Chem. Res. 1986, 19, 300-306.
Ichikawa et al; "Hydrogen Absorption and Hydrogen Exchange Reactions in Solution by 1 : 2 Electron Donor-Acceptor Complexes of Anthracene with Various Alkali Metals", J. Am. Chem. Soc. 1971, 93, 2079-2080.
International Search Report for PCT Application No. PCT/IL2011/000687 mailed on Nov. 7, 2011.
Jain et al.; "Consequences of Nonergodicity in Aqueous Binary PEO-PB Micellar Dispersions", Macromolecules 2004, 37, 1511-1523.
Jones et al. "High-Mobility Air-Stable n-Type Semiconductors with Processing Versatility: Dicyanoperylene-3, 4:20049, 10-bis (dicarboximides)," Angew. Chem. Int. Ed. 43, 6363-6366, (2004).
Kaminker et al.; "Molecular Structure-Function Relations of the Optical Properties and Dimensions of Gold Nanoparticle Assemblies", Angew. Chem. 2010, 122, 1240-1243.
Kane et al.; "Kosmotropes Form the Basis of Protein-Resistant Surfaces", Langmuir 2003, 19, 2388-2391.
Katz; "The Cyclooctatetraenyl Dianion", J. Am. Chem. Soc. 1960, 82, 3784-3785.
Keller et al.; "The bioseparation needs for tomorrow", Trends Biotechnol. 2001, 19, 438-441.
Kimling et al.; "Turkevich Method for Gold Nanoparticle Synthesis Revisited", J. Phys. Chem. B 2006, 110, 15700-15707.
Kingshott et al.; "Effects of cloud-point grafting, chain length, and density of PEG layers on competitive adsorption of ocular proteins", Biomaterials 2002, 23, 2043-2056.
Krieg et al.; "A recyclable supramolecular membrane for size-selective separation of nanoparticles", Nature Nanotech. 2011, 6, 141-146.
Krieg et al.; "Supramolecular Gel Based on a Perylene Diimide Dye: Multiple Stimuli Responsiveness, Robustness, and Photofunction", Am. Chem. Soc. 2009, 131, 14365-14373.
Langhals et al.; "Novel Fluorescent Dyes by the Extension of the Core of Perylenetetracarboxylic Bisimides," European Journal of Organic Chemistry, vol. 2000, Iss. 2, pp. 365-380, (2000).
Langhals; "Control of the Interactions in Multichromophores: Novel Concepts. Perylene Bis-imides as Components for Larger Functional Units," Helvetica Chimica Acta vol. 88, Issue 6, pp. 1309-1343, (2005).
Langhals; "Synthesis of highly pure perylene fluorescent dyes in large scale amounts-specific preparation of atropisomers," Chemische Berichte, vol. 118, No. 11, pp. 4641-4645, (1985).
Langhals;. "A novel fluorescent dye with strong, anisotropic solid-state fluorescence, small stokes shift, and high photostability," Angew Chem Int Ed Engl. 44(16):2427-8, Apr. 15, 2005.
Li et al. "Energy transfer switching in a bistable molecular machine," Org Lett.; 7(22):4835-8. Oct. 27, 2005.
Li et al.; "Synthesis and characterization of ferrocene-perylenetetracarboxylic diimide-fullerene triad", Tetrahedron, vol. 61, Issue 6, pp. 1563-1569, Feb. 7, 2005.
Li et al.; "Synthesis, Characterization, and Self-Assembly of Nitrogen-Containing Heterocoronenetetracarboxylic Acid Diimide Analogues: Photocyclization of N-Heterocycle-Substituted Perylene Bisimides," Chem. Eur. J., 12, pp. 8378-8385, (2006).
Li et al.; "Ultrafast Aggregate-to-Aggregate Energy Transfer within Self-assembled Light-Harvesting Columns of Zinc Phthalocyanine Tetrakis(Perylenediimide)," J. Am. Chem. Soc. 126, 10810-10811, (2004).
Li et al.; "Multicompartment Micelles from ABC Miktoarm Stars in Water", Science 2004, 306, 98-101.
Lightfoot et al.; "Bioseparations", Biotechnol. Bioeng. 2004, 87, 259-273.
Lim et al.; "Rod-coil block molecules: their aqueous self-assembly and biomaterials applications", Mater. Chem. 2008, 18, 2909-2909.
Locklin et al.; "Organic Thin Film Transistors Based on Cyclohexyl-Substituted Organic Semiconductors," Chem. Mater., 17 (13), pp. 3366-3374, (2005).
Lu et al.; "Electrochemical Characterization, Electrochroism, and Voltage-Dependent Fluorescence of Novel Perylene-Containing Polyimides", Macromolecules 1999, 32, 8880-8885.
Lu et al.; "Nanofiltration Membranes based on Rigid Star Amphiphiles", Chem. Mater. 2007, 19, 3194-3204.
Lu et al.; "Fractionation of Lysozyme and Chicken Egg Albumin Using Ultrafiltration with 30-kDa Commercial Membranes", Ind. Eng. Chem. Res. 2005, 44, 7610-7616.
Müllen et al.; "Dianion and Tetraanion of Octalene", Chem. Int. Ed. 1979, 18, 229-231.
Müllen et al.; "Highly Reduced Annulenes. Novel Probes for Spectroscopy and Theory", J. Am. Chem. Soc. 1982, 104, 5403-5411.
Müllen; "The Dianions of Phenanthrene and 1,2,3,4-Dibenzocyclooctatetraene", Helv. Chim. Acta 1978, 61, 1296-1304.
Müllen; "The Dianions of Pyrene and Pyrene Isomers as (4n)n-Perimeters')", Helv. Chim. Acta 1978, 61, 2307-2317.

(56) References Cited

OTHER PUBLICATIONS

Nunes et al.; "Switchable pH-Responsive Polymeric Membranes Prepared via Block Copolymer Micelle Assembly", ACS Nano 2011, 5, 3516-3522.

Peeva et al.; "Performance of Thin-Layer Hydrogel Polyethersulfone Composite Membranes during Dead-End Ultrafiltration of Various Protein Solutions", Ind. Eng. Chem. Res. 2012, 51, 7231-7241.

Peinemann et al.; "Asymmetric superstructure formed in a block copolymer via phase separation", Nat. Mater. 2007, 6, 992-996.

Peng; "Using redundant internal coordinates to optimize equilibrium geometries and transition states," Journal of Computational Chemistry, vol. 17 Issue 1, pp. 49-56, (1996).

Prathapan et al.; "Synthesis and Excited-State Photodynamics of Perylene-Porphyrin Dyads. 1. Parallel Energy and Charge Transfer via a Diphenylethyne Linker," J. Phys. Chem. B, 105 (34), pp. 8237-8248, (2001).

Prins et al.; "Noncovalent Synthesis Using Hydrogen Bonding", Chem. Int. Ed. 2001, 40, 2382-2426.

Qu et al.; "Dendronized perylenetetracarboxdiimides with peripheral triphenylamines for intramolecular energy and electron transfer," Chem. Eur. J. 10, 528-537, (2004).

Rabinovitz et al.; "From Charged to Super-chargedl Systems: The Problem of "Aromaticity" in Polycyclic Ions", Acc. Chem. Res. 1983, 16, 298-304.

Rabinovitz et al.; "π-Conjugated polycyclic anions; interplay between topology, electronic structure and patterns of charge distribution", Pure Appl. Chem. 1993, 65, 111-118.

Rajasingh et al.; "Selective Bromination of Perylene Diimides under Mild Conditions" J. Org. Chem., 72, 5973-5979, (2007).

Roger et al.; "Efficient Energy Transfer from Peripheral Chromophores to the Self-Assembled Zinc Chlorin Rod Antenna: A Bioinspired Light-Harvesting System to Bridge the „Green Gap", Am. Chem. Soc. 128, 6542-6543, (2006).

Rybtchinski B et al.; "Combining Light-Harvesting and Charge Separation in a Self-Assembled Artificial Photosynthetic System Based on Perylenediimide Chromophores," J. Am. Chem. Soc.126 (39), pp. 12268-12269, (2004).

Ryu et al.; Aqueous self-assembly of aromatic rod building blocks Chem. Commun. 2008, 1043-1054.

Sautter A et al.; "Ultrafast Energy-Electron Transfer Cascade in a Multichromophoric Light-Harvesting Molecular Square," J. Am. Chem. Soc. 127 (18), pp. 6719-6729, (2005).

Saxena et al.; "Membrane-based techniques for the separation and purification of proteins: An overview", Adv. Coll. Int. Sci. 2009, 145, 1-22.

Schlegel; "Optimization of equilibrium geometries and transition structures," Journal of Computational Chemistry, vol. 3 Iss. 2, pp. 214-218, (1982).

Schmidt-Mende; et al. "Self-Organized Discotic Liquid Crystals for High-Efficiency Organic Photovoltaics," Science: vol. 293. No. 5532, pp. 1119-1122, Aug. 10, 2001.

Schmuck et al.; "Highly Stable Self-Assembly in Water: Ion Pair Driven Dimerization of a Guanidiniocarbonyl Pyrrole Carboxylate Zwitterion", J. Am. Chem. Soc. 2003, 125, 452-459.

Shin et al.; "Effects of functional groups at perylene diimide derivatives on organic photovoltaic device application," J. Mater. Chem.16, 384-390, (2006).

Shirman et al.; "Stable Aromatic Dianion in Water", J. Phys. Chem. B, 2008, 112, 8855-8858.

Srere et al.; "Citrate condensing enzyme of pigeon breast muscle and moth flight muscle", Acta Chem. Scand. 1963, 17, S129-S134.

Struijk et al.; "Liquid Crystalline Perylene Diimides: Architecture and Charge Carrier Mobilities," J. Am. Chem. Soc. 122 (45), pp. 11057-11066, (2000).

Tidhar et al.; "Pathway-Dependent Self-Assembly of Perylene Diimide/Peptide Conjugates in Aqueous Medium", Chem. Eur. J. 2011, 17, 6068-6075.

Tokarev et al.; "Multiresponsive, Hierarchically Structured Membranes: New, Challenging, Biomimetic Materials for Biosensors, Controlled Release, Biochemical Gates, and Nanoreactors", Adv. Mater. 2009, 21, 241-247.

Turkevich et al.; "A Study of the Nucleationand Growth Processes in the Synthesis of Colloidal Gold", Discuss. Faraday Soc. 11, 55 (1951).

Tyagi et al.; "Dynamic Interactive Membranes with Pressure-Driven Tunable Porosity and Self-Healing Ability", Chem. Int. Ed. 2012, 51, 7166-7170.

Uehara et al.; "Size-Selective Diffusion in Nanoporous but Flexible Membranes for Glucose Sensors", ACS Nano 2009, 3, 924-932.

Ulbricht; "Advanced functional polymer membranes", Polymer 2006, 47, 2217-2262.

Vanburgel et al.; "The dynamics of one-dimensional excitons in liquids", J. Chem. Phys. 1995, 102, 20-33.

Wang et al."'Alternating DNA and π-Conjugated Sequences. Thermophilic Foldable Polymers," J. Am. Chem. Soc.125 (18), pp. 5248-5249, (2003).

Wasielewski; "Energy, Charge, and Spin Transport in molecules and Self-Assembled Nanostructures Inspired by Photosynthesis," J. Org. Chem. 71, pp. 5051-5066, (2006).

Willner et al.; "Manifestation of Dual Aromaticity in Doubly Charged Annelated Pentalenes", Am. Chem. Soc. 1979, 101, 395-401.

Wuelfing et al.; "Nanometer Gold Clusters Protected by Surface-Bound Monolayers of Thiolated Poly(ethylene glycol) Polymer Electrolyte", J. Am. Chem. Soc. 120, 12696 (1998).

Würthner et al.; "Preparation and Characterization of Regioisomerically Pure 1, 7-Disubstituted Perylene Bisimide Dyes," J. Org. Chem. 69, 7933-7939, (2004).

Würthner et al.; "Metallosupramolecular squares: from structure to function," Chem. Soc. Rev.,33, pp. 133-146, (2004).

Würthner; "Perylene bisimide dyes as versatile building blocks for functional supramolecular architectures," Chemical communications 2004, No. 14, pp. 1564-1579.

Xiao et al.; "Dyads and triads containing perylenetetracarboxylic diimide and porphyrin: efficient photoinduced electron transfer elicited via both excited singlet states," J Phys Chem B.;109(8):3658-67,Mar. 3, 2005.

Yakimov et al.; "High photovoltage multiple-heterojunction organic solar cells incorporating interfacial metallic nanoclusters," Appl. Phys. Lett. 80, 1667, (2002).

Yang et al.; "Single File Diffusion of Protein Drugs through Cylindrical Nanochannels", ACS Nano 2010, 4, 3817-3822.

Yoo et al.; "High-mobility bottom-contact n-channel organic transistors and their use in complementary ring oscillators," Appl. Phys. Lett. 88, 082104, (2006).

You et al.; "Light-harvesting metallosupramolecular squares composed of perylene bisimide walls and fluorescent antenna dyes," Chemistry.12 (28):7510-9, Sep. 25, 2006.

Zang et al.; "A Single-Molecule Probe Based on Intramolecular Electron Transfer," J. Am. Chem. Soc.124 (36), pp. 10640-10641, (2002).

Zhang et al.; "Morphology Control of Fluorescent Nanoaggregates by Co-Self-Assembly of Wedge- and Dumbbell-Shaped Amphiphilic Perylene Bisimides", J. Am. Chem. Soc. 2007, 129, 4886-4887.

Zhang et al.; "The Influence of Carboxyl Groups on the Photoluminescence of Mercaptocarboxylic Acid-Stabilized CdTe Nanoparticles", J. Phys. Chem. B107, 8 (2003).

Zhao et al;. "3, 4:9, 10-Perylenebis (dicarboximide) chromophores that function as both electron donors and acceptors," Tetrahedron Letters, vol. 40, Iss. 39, pp. 7047-7050, (1999).

Zollinger; "Color Chemistry. 3rd ed" Verlag Helvetica Chimica Acta, Zürich, Wiley-VCH, Weinheim, (2003).

PEG = polyethylene glycol

Before filtration:

Filtrate:

Before filtration:

Filtrate:

SEPARATION OF NANOPARTICLES

CROSS REFERENCE TO RELATED APPLICATIONS

This application is a Continuation-in-Part application of International Application Number PCT/IL2011/000687 filed 25 Aug. 2011, which claims priority of U.S. Provisional Ser. No. 61/377,540 filed 27 Aug. 2010 which are incorporated in their entirety herein by reference.

FIELD OF THE INVENTION

This invention is directed to separation, optimization and purification of nano-materials using self-assembled perylene diimide membranes, wherein said perylene diimide membrane is recyclable.

BACKGROUND OF THE INVENTION

Separation and purification of nanoparticles (NPs) or biomolecules becomes increasingly important both for fundamental studies and applications. Known separation techniques include size exclusion chromatography, size-selective precipitation, gel electrophoresis and (ultra)centrifugation. Although these techniques can be used to separate according to size they are usually time- or energy consuming. An emerging alternative to these methods is represented by filtration techniques. In particular, ultrafiltration is a pressure-driven separation process in which porous membranes retain particles larger than the membrane cut-off (ranging from 2 to 100 nm). Membrane processes allow fast separation, the use of small solvent volumes, and are suitable for separation and purification of various NPs. Filtration can be easily scaled up, allowing separation and purification on the industrial scale. All commercially available filtration membranes used today are either polymer-based or ceramic. Supramolecular structures have been used as templates for porous membranes and for modification of membrane pores. The challenge in creating supramolecular filtration membranes relates to the robustness and the structure that is adequate for filtration, requiring a uniform porous array that maintains its integrity and pore sizes under the forces created by percolation of solvents and solutes during the filtration process.

Membrane filtration is an essential tool in the biotechnological industry and appears to be particularly useful for the purification and concentration of proteins. Moreover, membranes can be used for immobilization and biocatalytic utilization of enzymes. As enzymes catalyze reactions under very mild conditions, exhibiting efficiency and selectivity largely unmatched by synthetic catalysts, such membrane reactors are emerging components in new, environmentally friendly industrial processes (heterogeneous biocatalysis), which may supplement or replace traditional chemical methods.

Separation of chiral compounds is of great interest since the majority of bioorganic compounds (sugars, amino-acids, sugar, proteins, nucleic acids) are chiral. Chirality is a major concern also in the pharmaceutical industry, since drugs with different chirality may have different pharmacological activities as well different pharmacokinetic and pharmacodynamic effects. Chiral HPLC and chiral GC have proven to be one of the methods for the direct separation of enantiomers. However, there is still no one universal column that has the ability to separate all classes of racemic compounds.

Filtration membranes which are used today are based on polymers or ceramics. Supramolecular systems have been utilized as templates for polymer membrane pores, rather than the membrane material itself. Recently, substantial progress has been made in fabricating supramolecular membranes. However, these membranes employ conventional high molecular weight polymers, and those that were applied to biological systems underwent elaborate modifications of the self-assembled material prior to use.

SUMMARY OF THE INVENTION

In one embodiment, this invention is directed to noncovalent self-assembled porous membrane comprising a perylene diimide supramolecular structure.

In one embodiment, this invention is directed to noncovalent self-assembled porous membrane comprising a perylene diimide supramolecular structure; providing a chromatography medium for size-selective separation of nano-materials, wherein the perylene diimide structure comprises perylene diimide monomeric units of formula I-XIV.

In one embodiment, this invention is directed to noncovalent self-assembled porous chiral membrane comprising a perylene diimide supramolecular structure of this invention; providing a chromatography medium for size-selective separation of nano-materials and chiral separation, wherein the perylene diimide structure comprises perylene diimide monomeric units of formula I-XIV.

In one embodiment, this invention is directed to a method of separation/filtration or purification of nanoparticles comprising (a) transferring an aqueous solution or emulsion comprising a perylene diimide supramolecular structure of this invention through porous solid support, thereby forming a noncovalent self-assembly perylene based membrane on said porous solid support; (b) transferring nanoparticles through said noncovalent self-assembly perylene based membrane of step (a); wherein the particles size which are larger than the pores of said membrane remain on said membrane.

In one embodiment, this invention is directed to a method of separation/filtration or purification of biomolecules comprising (a) transferring an aqueous solution or emulsion comprising a perylene diimide supramolecular structure of this invention through porous solid support, thereby forming a noncovalent self-assembly perylene based membrane on said porous solid support; (b) transferring a solution of biomolecules through said noncovalent self-assembly perylene based membrane of step (a); wherein the particles size which are larger than the pores of said membrane remain on said membrane.

In one embodiment, this invention is directed to a method of separation/filtration or purification of chiral nano-materials comprising (a) transferring an aqueous solution or emulsion comprising a chiral perylene diimide supramolecular structure of this invention through porous solid support, thereby forming a noncovalent self-assembly chiral perylene based membrane on said porous solid support; (b) transferring chiral nano-materials through said noncovalent self-assembly perylene based membrane of step (a); wherein the chiral-nano-materials are separated/filtered or purified.

In one embodiment, this invention provides a method of recycling the noncovalent self-assembly perylene diimide based membrane comprising; (a) washing said microfiltration filter with the membrane of this invention and the retained retentate with a mixture of alcohol and water; (b) extracting said perylene structure with an organic solvent; and (c) isolating said perylene structure which can be further used to form a noncovalent self-assembly perylene based membrane in aqueous conditions.

In one embodiment, this invention provides a method of isolating the retenate on the membrane of this invention the comprising (a) washing said microfiltration filter with said membrane of this invention and said retained nanoparticles with a mixture of alcohol and water; (b) extraction of said perylene structure with an organic solvent, and said retained nanoparticles remain in the aqueous phase.

In one embodiment, this invention is directed to a method of preparing a noncovalent self-assembly perylene diimide based membrane comprising (a) preparing an organic solution of perylene diimide of this invention, wherein said organic solvent is miscible in water; (b) adding excess of water to said solution of (a); wherein the ratio between said organic solvent to water is between about 3:97 to 8:92 v/v; (c) evaporating said organic solvent; and (d) transferring said aqueous solution or emulsion of (c) through a solid support to obtain a noncovalent self-assembly perylene based membrane.

In one embodiment, this invention is directed to a biocatalytic membrane comprising a noncovalent self-assembled porous membrane comprising a perylene diimide supramolecular structure and an enzyme; wherein said enzyme is immobilized within said membrane; and said perylene diimide supramolecular structure comprises perylene diimide monomeric units of formula I-XIV.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 5A depicts membrane fabrication and recycling. FIG. 5B depicts the molecular structure of Perylene V resulting in supramolecular fibers, 3D network, and membrane. The Hydrophobic groups of PeryleneV are located in the fibers' core, whereas their hydrophilic PEG shell provides a biocompatible interface. Recycling of the membrane is achieved by disaggregation or physical removal of the supramolecular layer from the support, followed by purification, and subsequent reassembly in aqueous solution. (PP2b in the figure refers to Perylene V).

(G)-(L) Filtration experiment of Au8. (G) Representative TEM image of particles before filtration, and (H) particle size histogram. (I) Representative TEM image of particles in the filtrate, and (J) particle size histogram. (K) Photograph of filtration. (L) UV/Vis spectra of an Au8 solution before filtration (solid line), after filtration over CA (control measurement, dashed line), and after filtration over the Perylene V membrane (dotted line). Since even small (~2 nm) charge-neutral (PEG-SH stabilized) AuNPs still exhibit a weak SPB (36, 37), the SPB does not vanish completely in the filtrate but weakens, and a resulting peak shift from 512 to 502 nm is observed. (PP2b in the figure refers to Perylene V).

Figure 8:
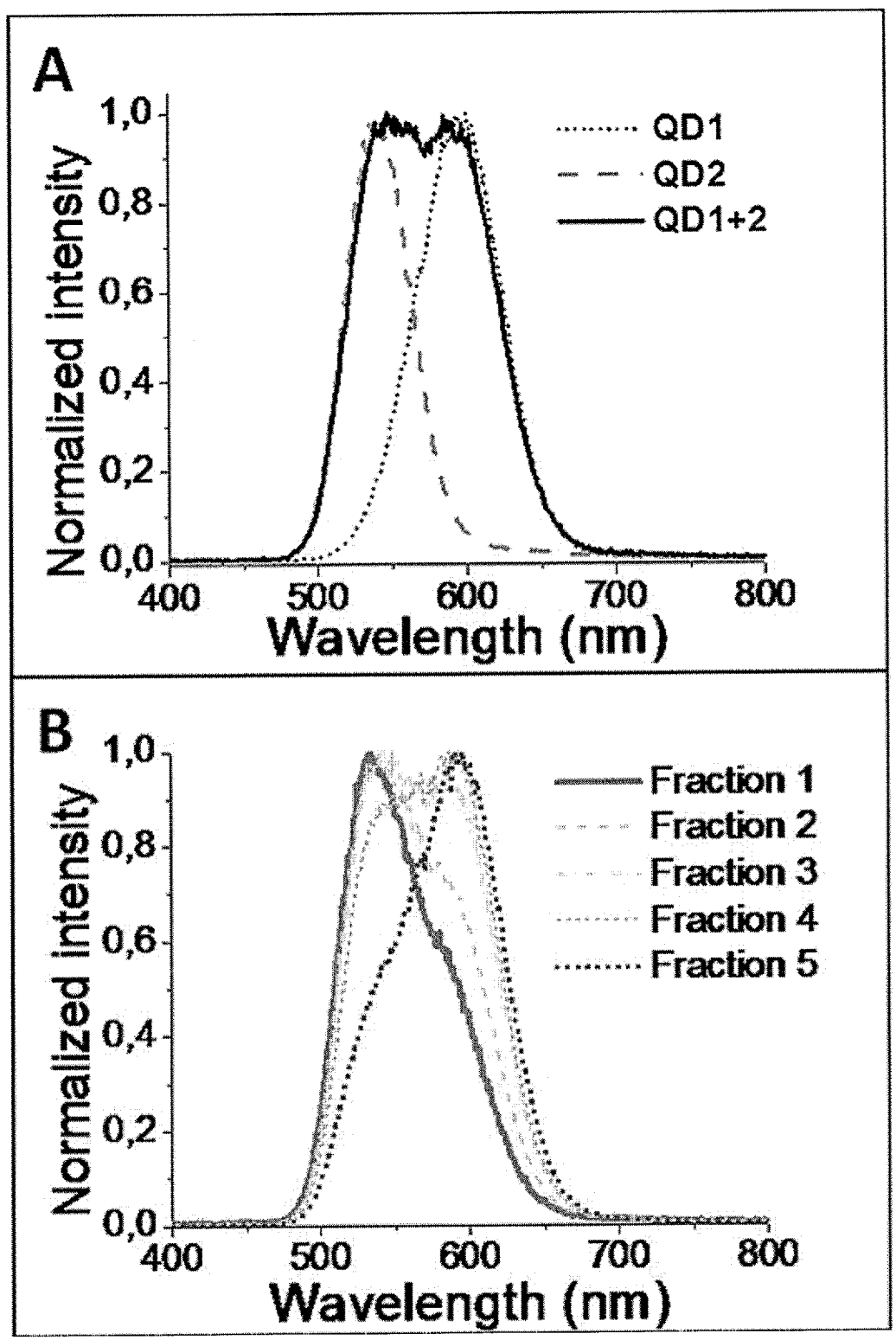
Figure 8:
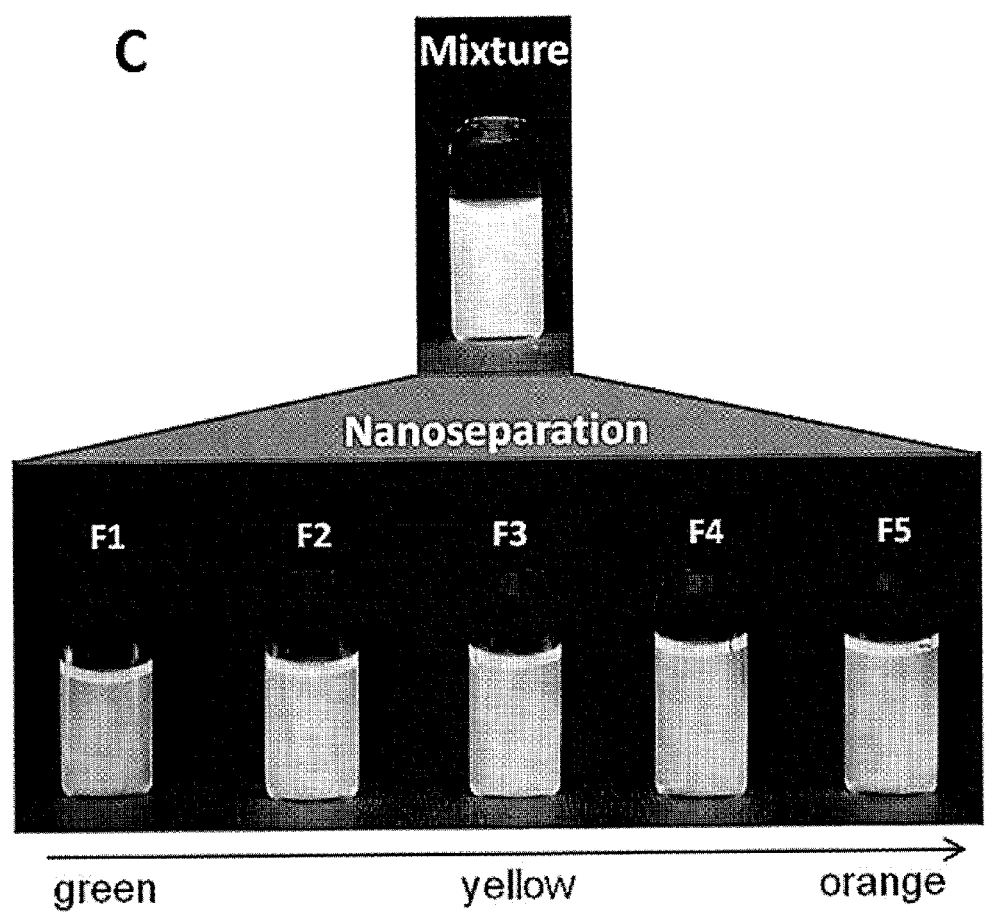

FIG. 8 depicts normalized luminescence spectra ($\lambda_{ex}$=390 nm) of (A) QD1 (dotted line), QD2 (dashed line), and their mixture (solid line), and (B) successive fractions collected by filtration of the QD mixture. (C) Photograph of the mixture (top) and the collected fractions (bottom) under UV light (365 nm).

Figure 9:
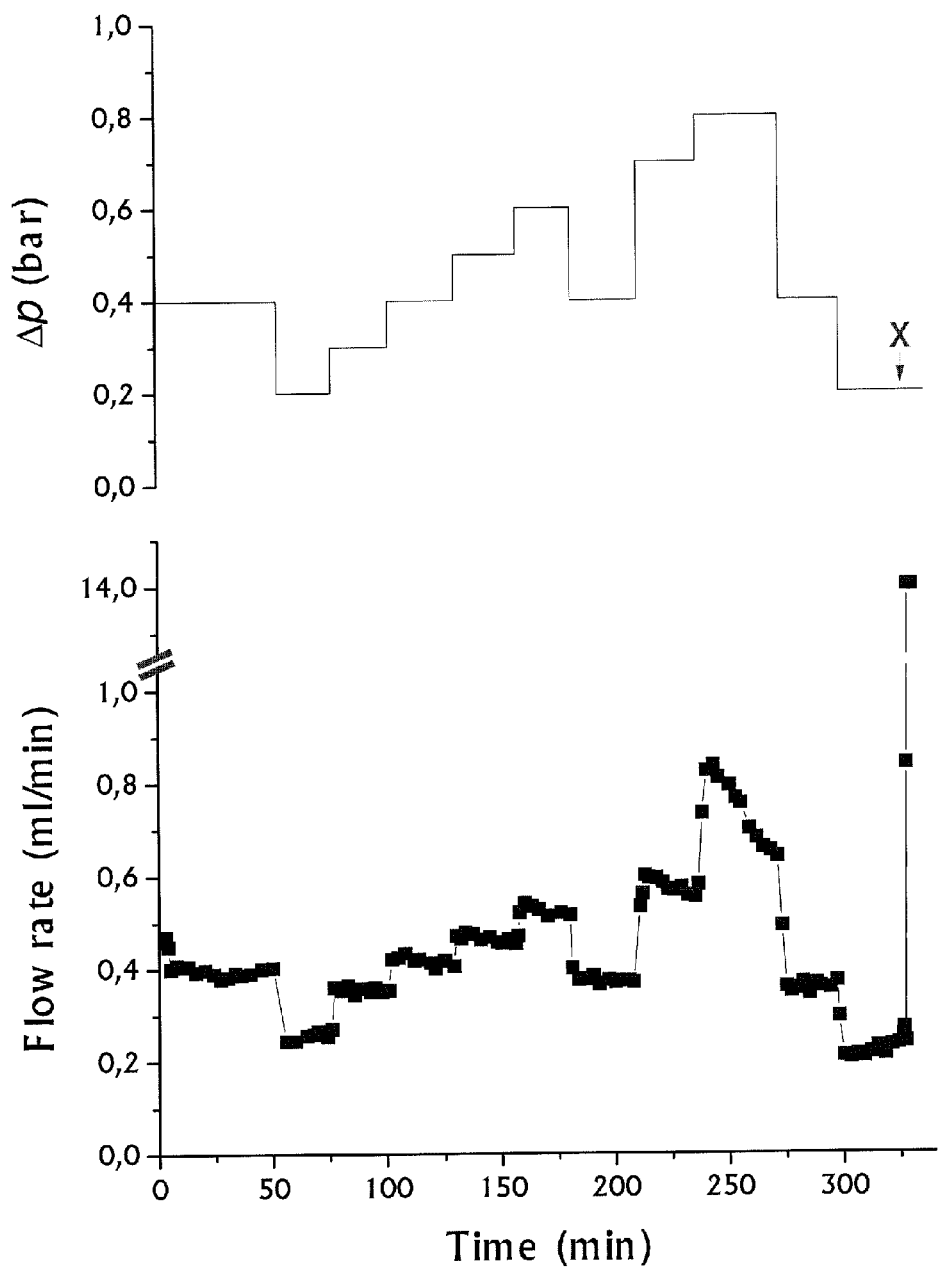

FIG. 9 depicts flow rate of water through a supramolecular membrane prepared from 0.5 ml Perylene V ($5 \cdot 10^{-4}$ M) on CA support (0.45 µm pore size, 5.7 cm$^2$ surface area; 0.13 mg Perylene V/cm$^2$) at 25° C. The top graph presents the stepwise variation of the trans-membrane pressure, $\Delta p$, with time. The bottom graph presents flow rate during that time and its response to changes in $\Delta p$. Flow rates are stable at pressures up to 0.7 bar. At 0.8 bar unstable flow is observed (minutes 240-270). The 'X' denotes the time of addition of water/ethanol (4:6, v/v) mixture, which causes disassembly of the supramolecular filter and a resulting jump in flow rate by almost two orders of magnitude. The flow rates were determined using the setup depicted in FIG. 2 in combination with a digital balance recording the weight gain caused by the change in filtrate volume.

Figure 10:
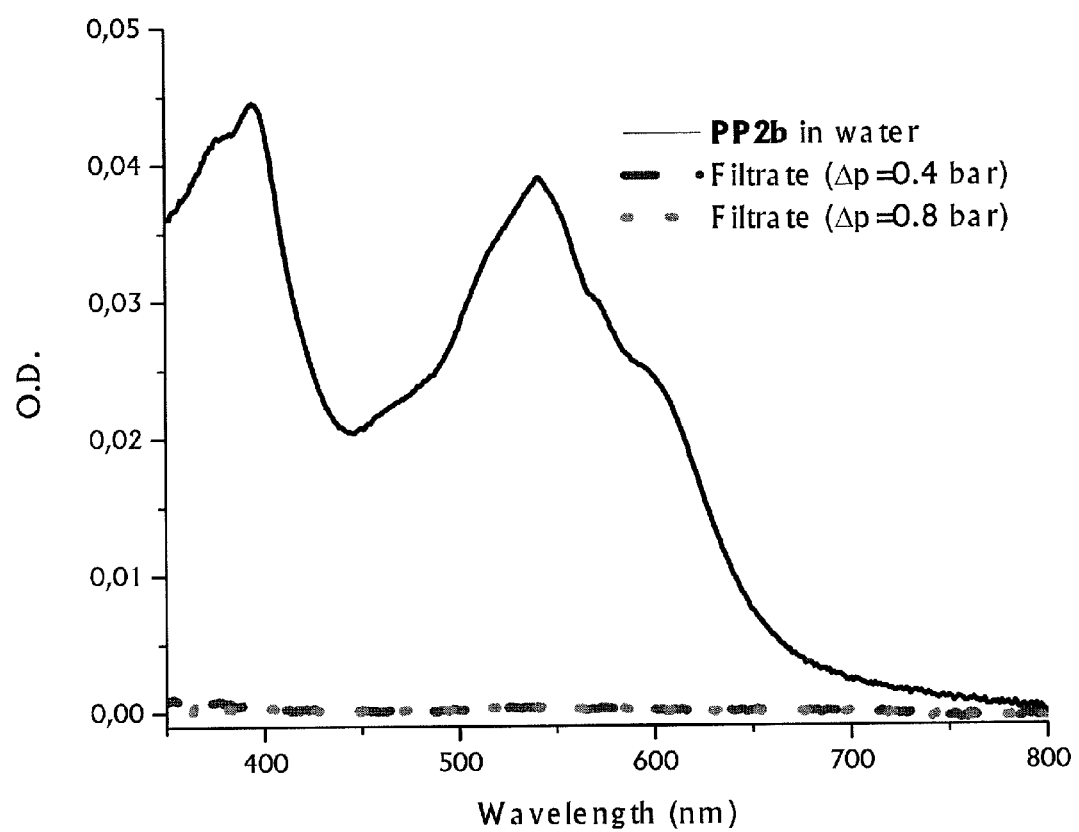

FIG. 10 depicts UV/Vis spectra of a dilute solution of Perylene V in water ($5 \cdot 10^{-6}$ M, solid line), the filtrates obtained from flow of water through a Perylene V supramolecular membrane at $\Delta p$=0.4 bar (dashed line) and at $\Delta p$=0.8 bar (dotted line). No traces of Perylene V are detectable in both filtrates. (PP2b in the figure refers to Perylene V).

Figure 11:
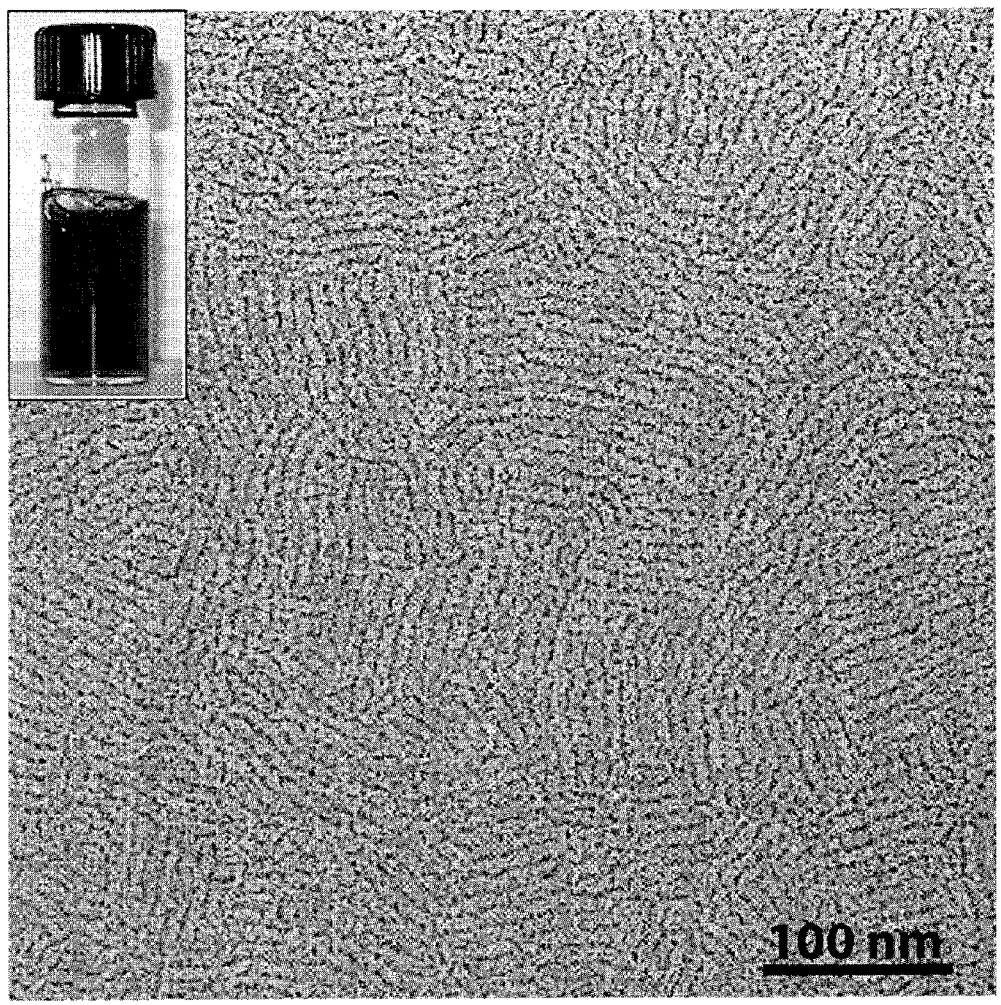

FIG. 11 depicts Cryo-TEM image of the solution of Perylene V ($10^{-4}$ M) in water. Inset: Photograph of the corresponding sample. Perylene V supramolecular fibers in water are composed of an inner core of stacked aromatic units (high contrast), and an outer PEG-shell (low contrast). The inner core is 2.8±0.5 nm wide. The total fiber width (inner core plus PEG-shell) is 8.3±1.1 nm. The fibers are uniform and very similar to previously reported Perylene V in water/THF mixtures.

Figure 12:
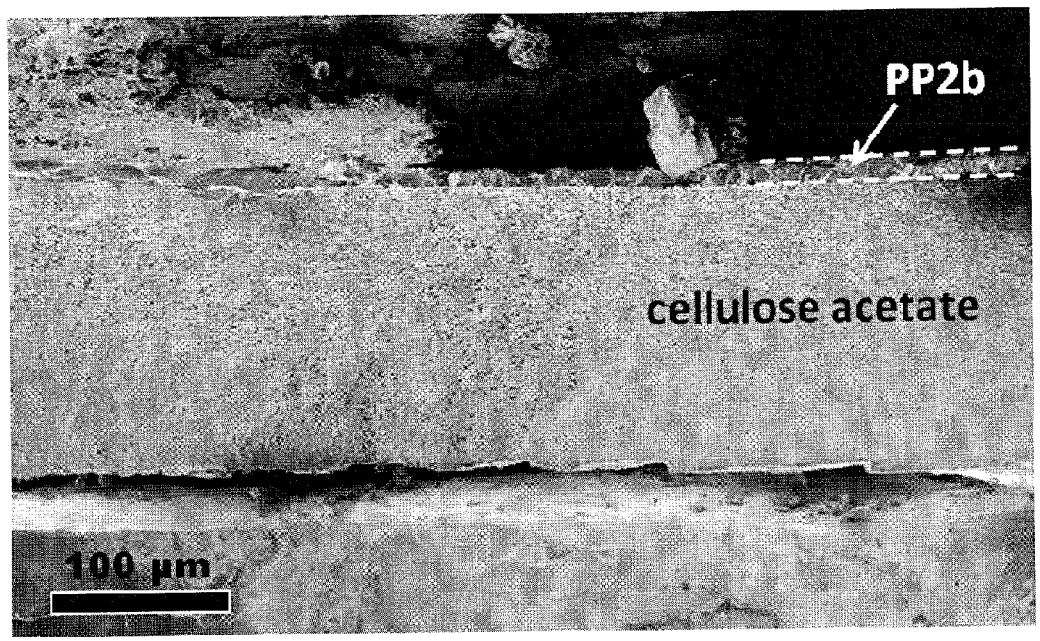

FIG. 12 depicts cryo-SEM image of the cross-section of the supramolecular filtration membrane (0.13 mg Perylene V/cm$^2$) on the CA support. (PP2b in the figure refers to Perylene V).

Figure 13:
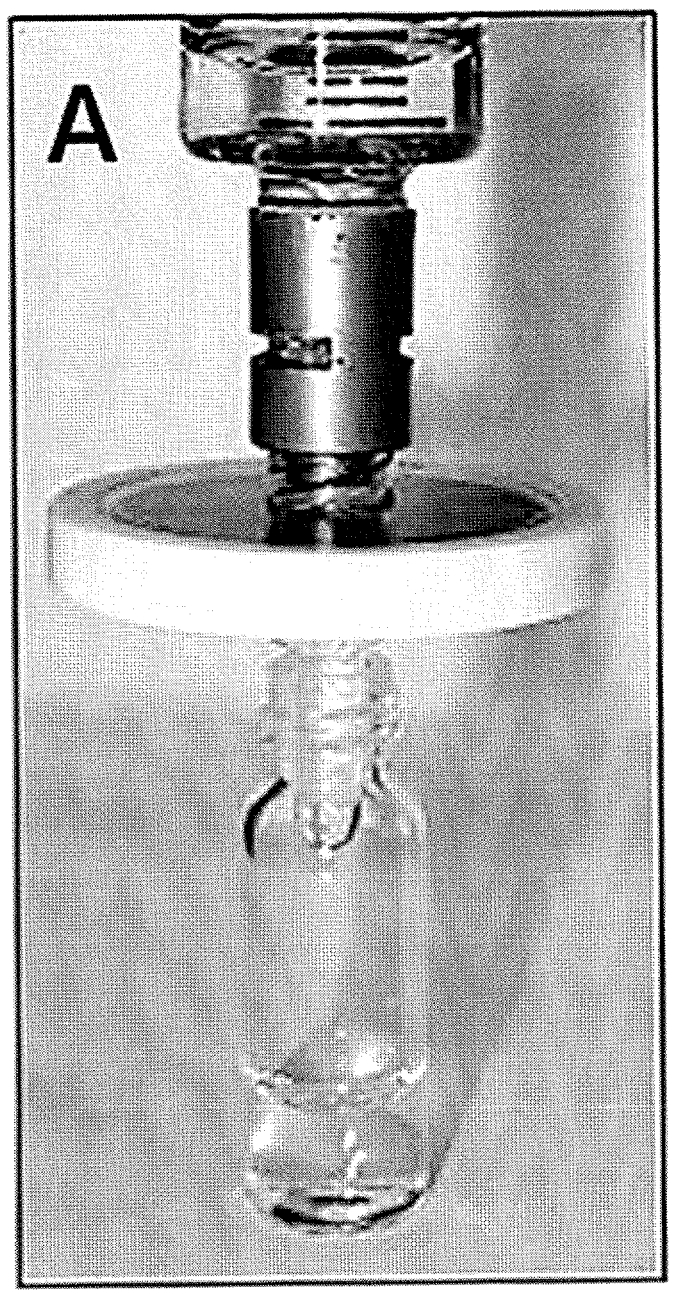
Figure 13:
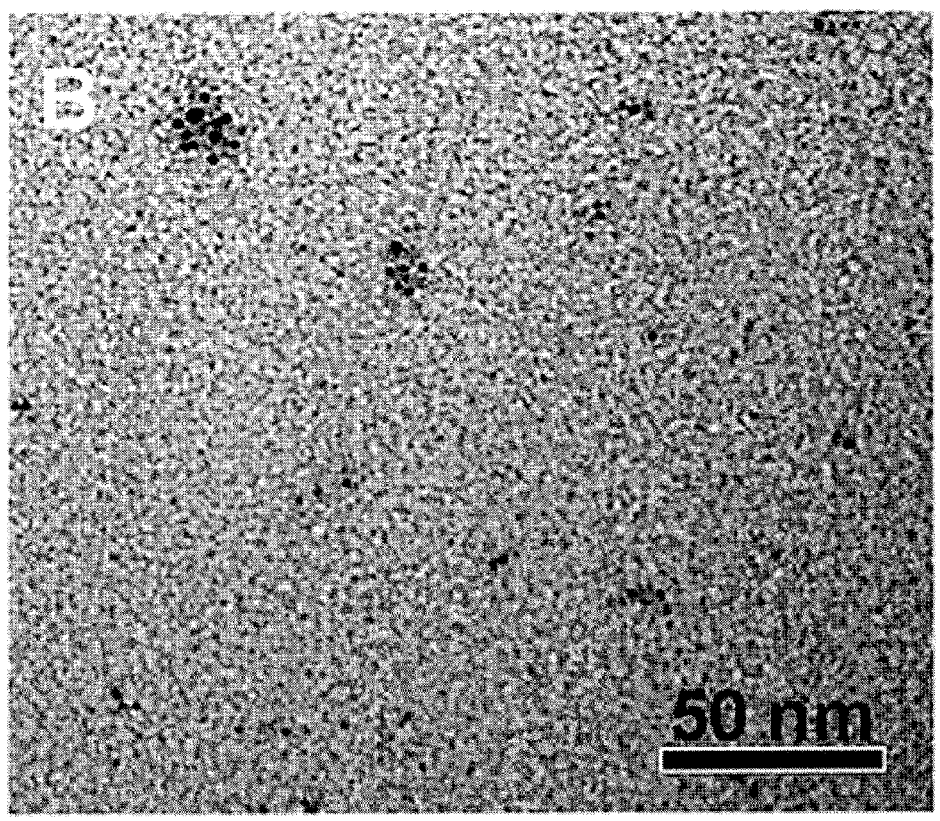
Figure 13:
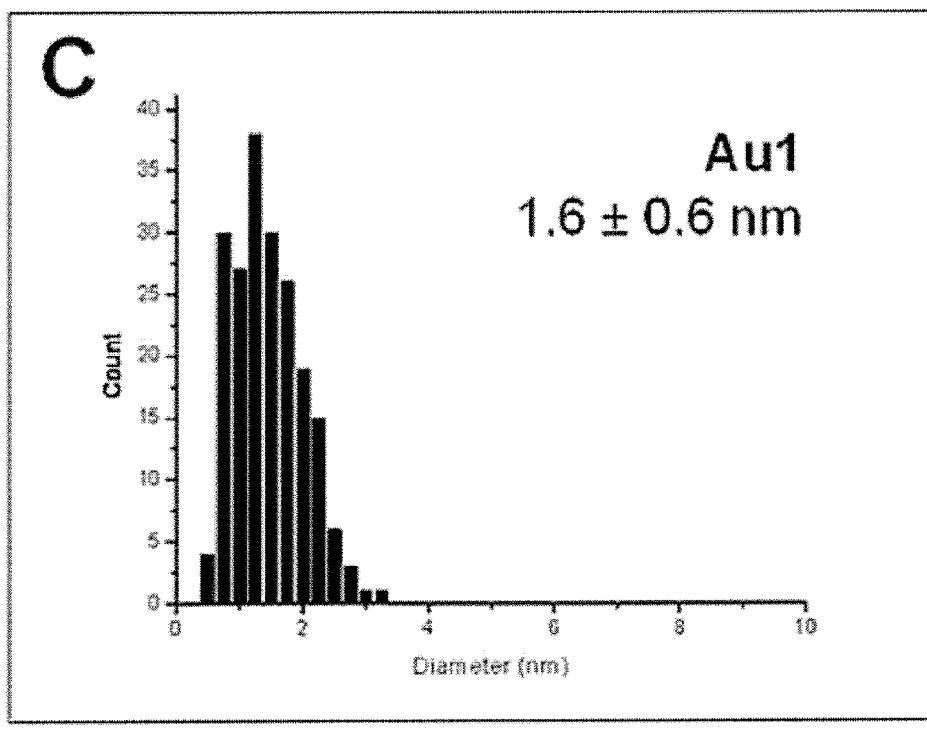
Figure 13:
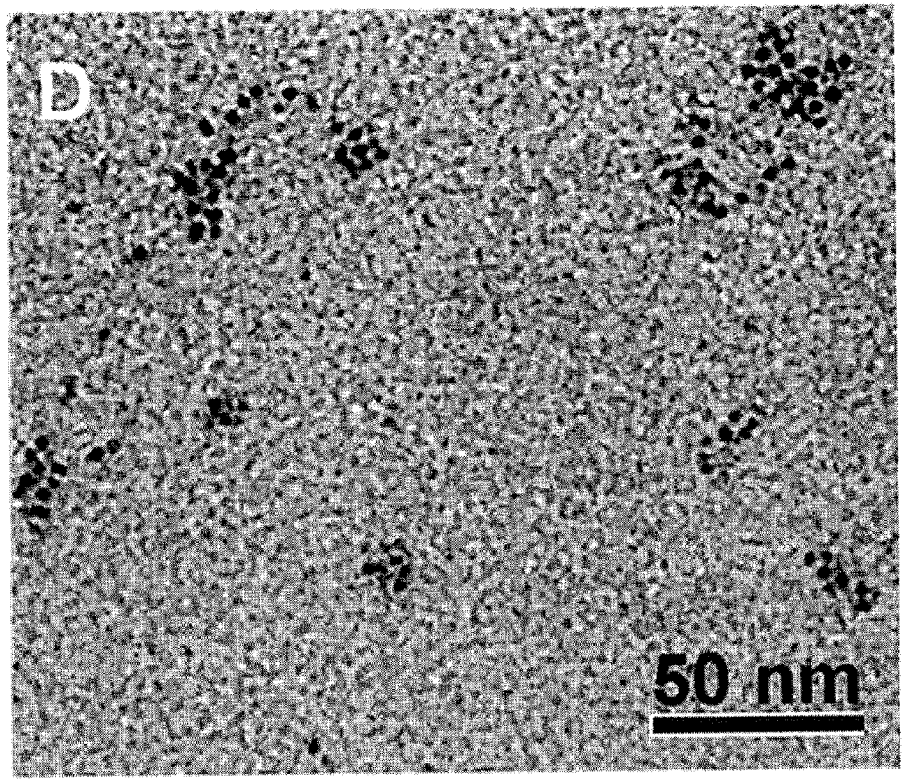
Figure 13:
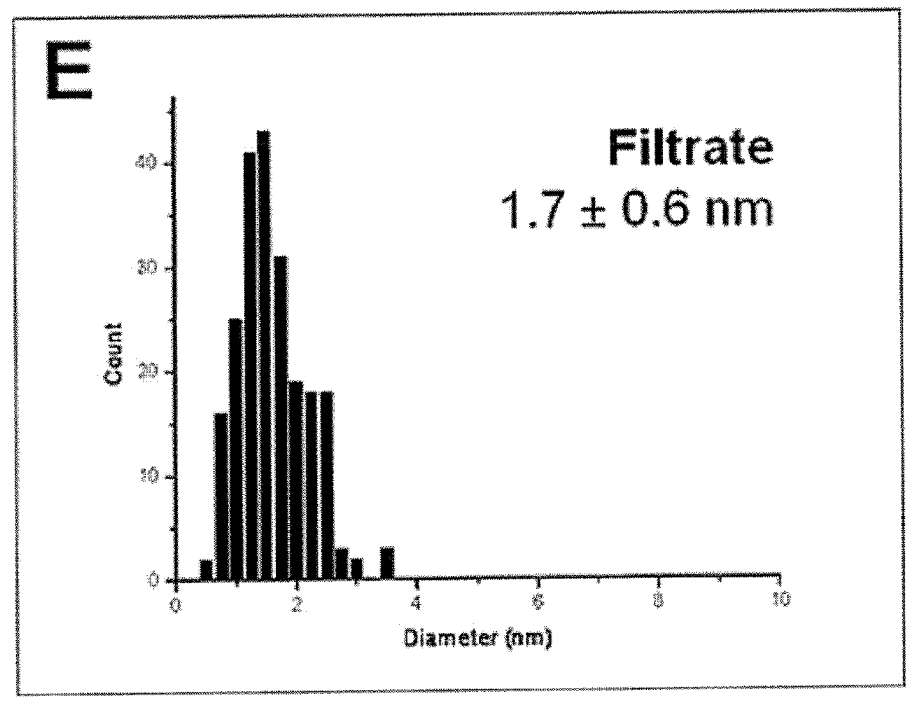

FIG. 13 depicts filtration experiment of Au1. (A) Photograph of filtration. (B) Representative TEM image of particles before filtration, and (C) particle size histogram. (D) Representative TEM image of particles in the filtrate, and (E) particle size histogram.

Figure 14:
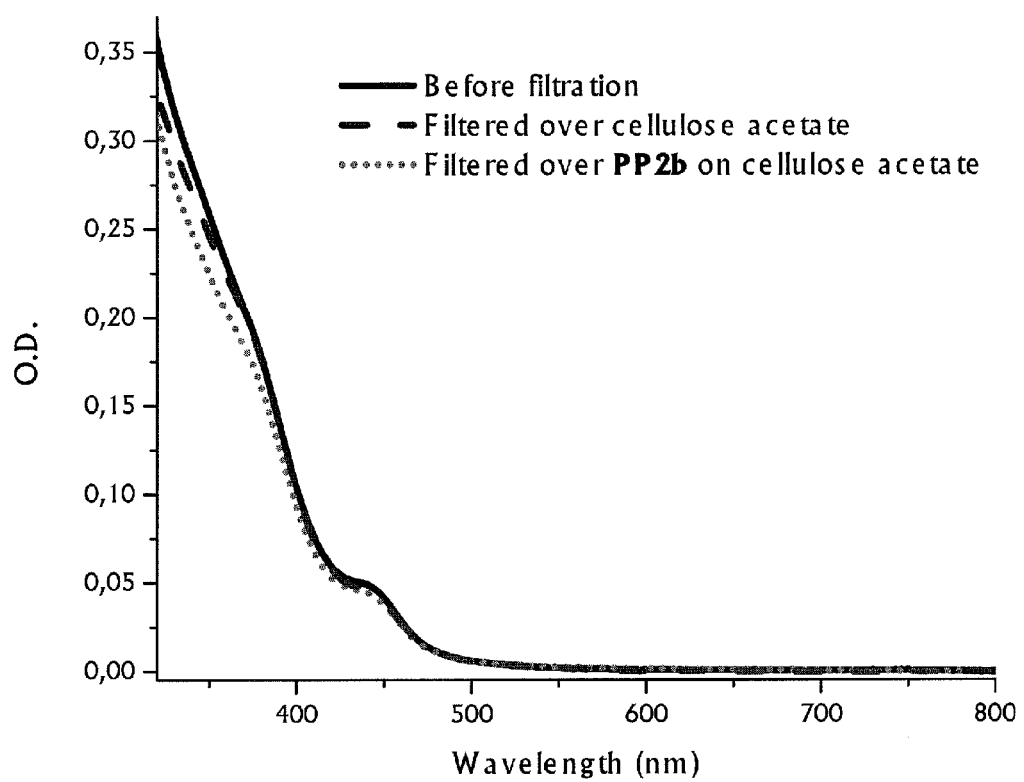

FIG. 14 depicts UV/Vis spectra of a Au1 solution before filtration (solid line), after filtration over CA only (dashed line), and after filtration over the Perylene V membrane (dotted line). (PP2b in the figure refers to Perylene V).

Figure 15:
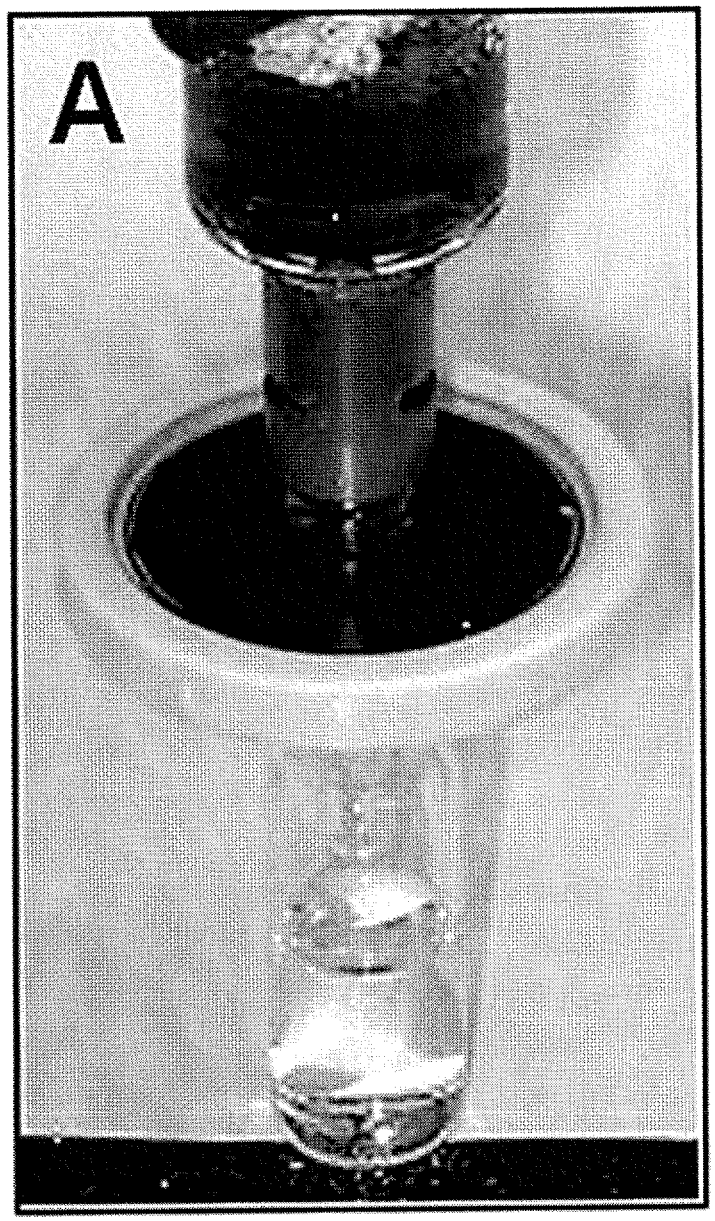
Figure 15:
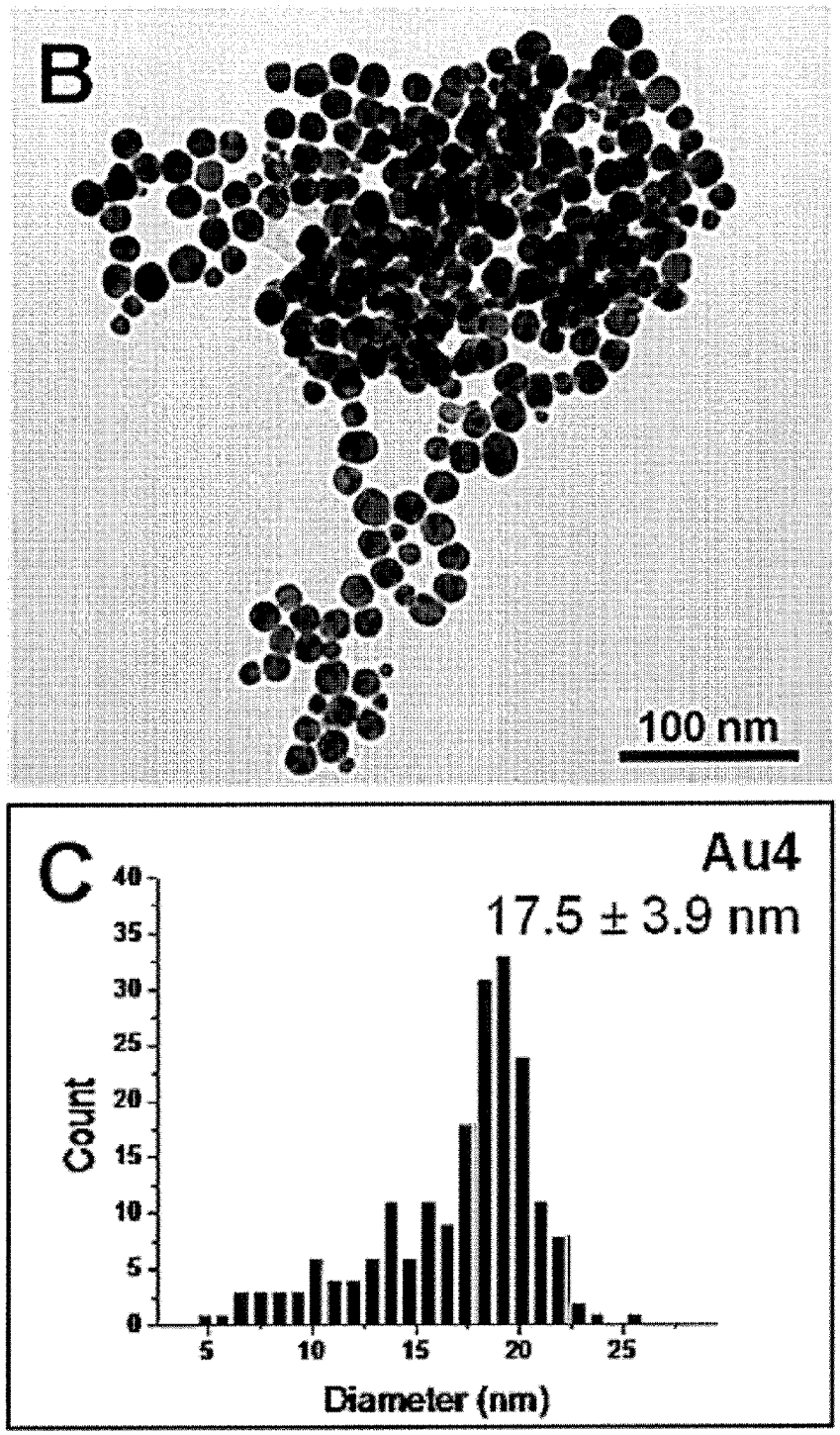
Figure 15:
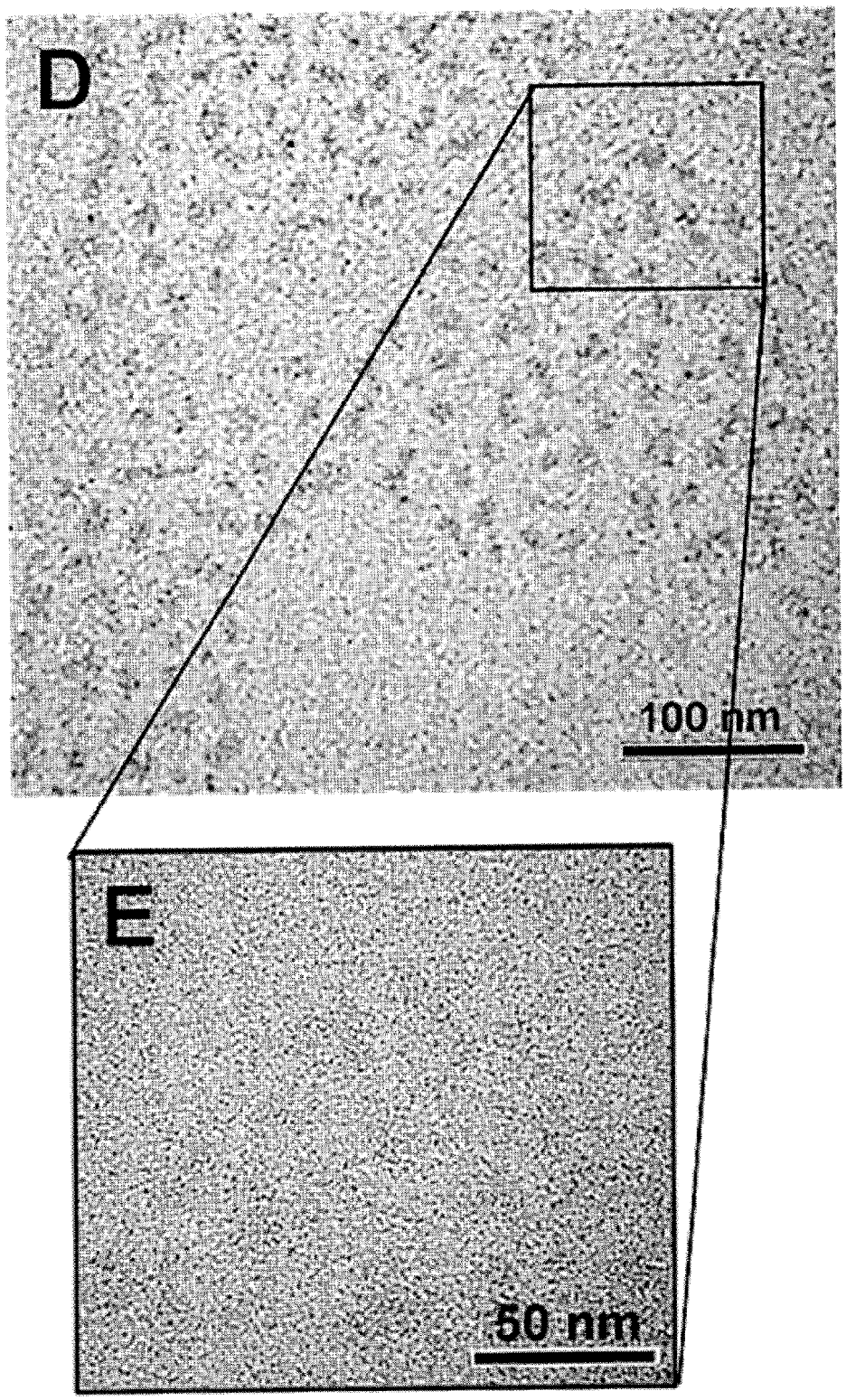

FIG. 15 Filtration experiment of Au4. (A) Photograph of filtration. (B) Representative TEM image of particles before filtration, and (C) particle size histogram. (D) Representative TEM image of the filtrate. (E) Magnified area. Low contrast dark areas in the filtrate are not nanoparticles, but may be excess of organic capping agent (MPA—Mercaptopropionic acid) that passes the membrane).

Figure 16:
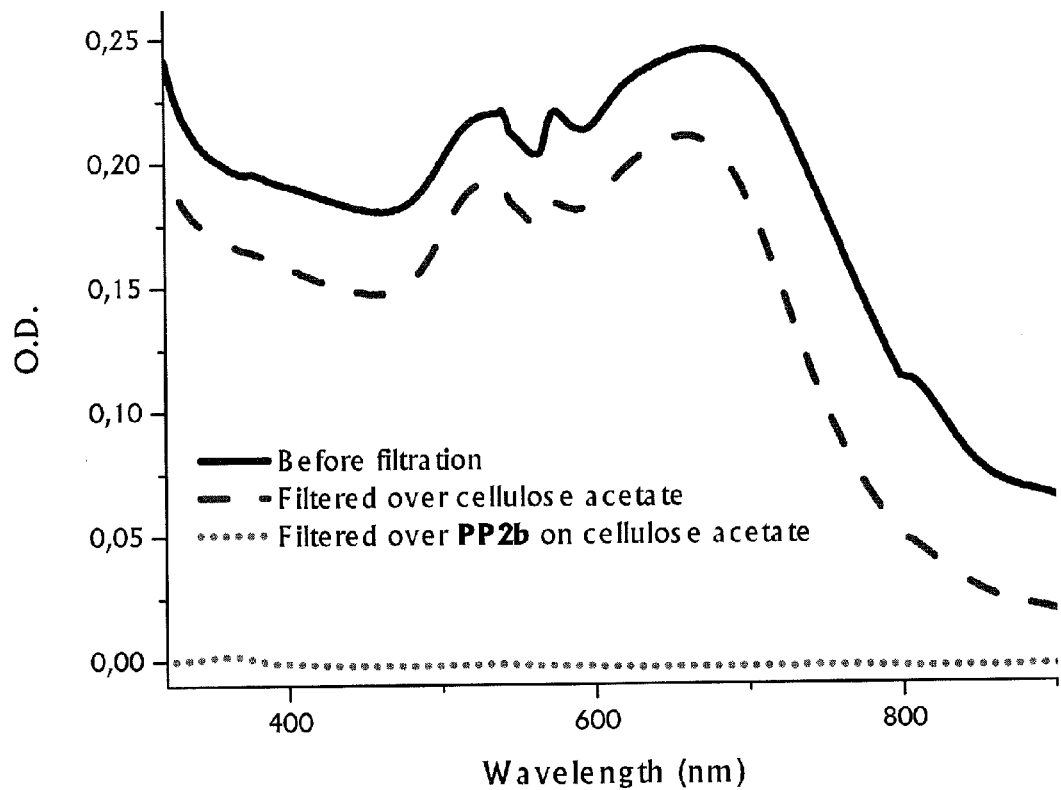

FIG. 16 depicts UV/Vis spectra of a Au4 solution before filtration (solid line), after filtration over CA as a control experiment (dashed line), and after filtration over the Perylene V membrane (dotted line). (PP2b in the figure refers to Perylene V).

Figure 17:
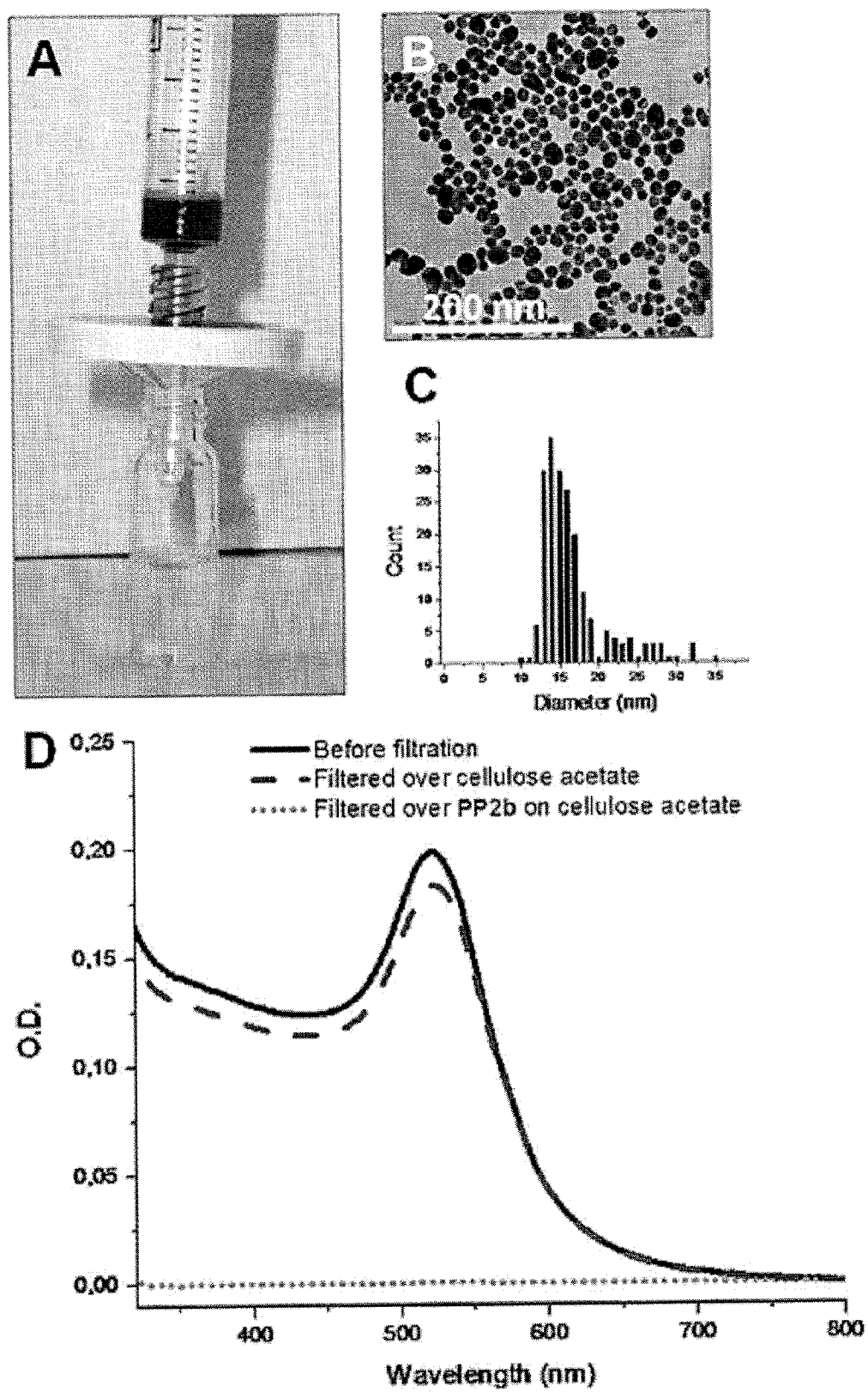

FIG. 17 depicts filtration experiment of Au5. (A) photograph of filtration. (B) Representative TEM image of particles before filtration. (C) corresponding histogram. (D) UV/Vis spectra of Au5 solution before filtration (solid line), after filtration over CA as a control experiment (dashed line), and after filtration over the Perylene V membrane (dotted line). (PP2b in the figure refers to Perylene V).

Figure 18:
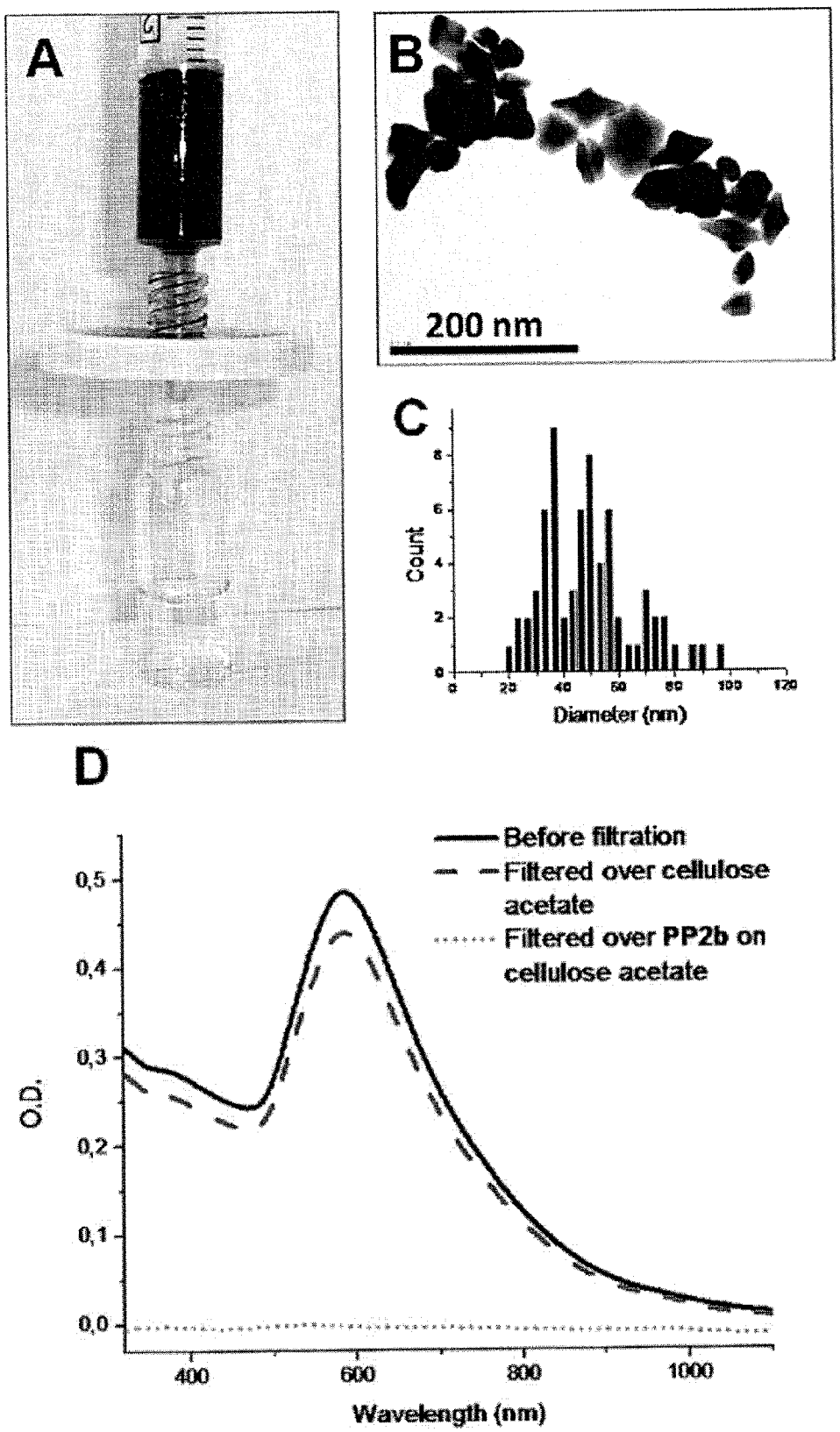

FIG. 18 depicts filtration experiment of Au6. (A) photograph of filtration. (B) Representative TEM image of particles before filtration. (C) corresponding histogram. (D) UV/Vis spectra of Au6 solution before filtration (solid line), after filtration over CA only (dashed line), and after filtration over the Perylene V membrane (dotted line). (PP2b in the figure refers to Perylene V).

Figure 19:
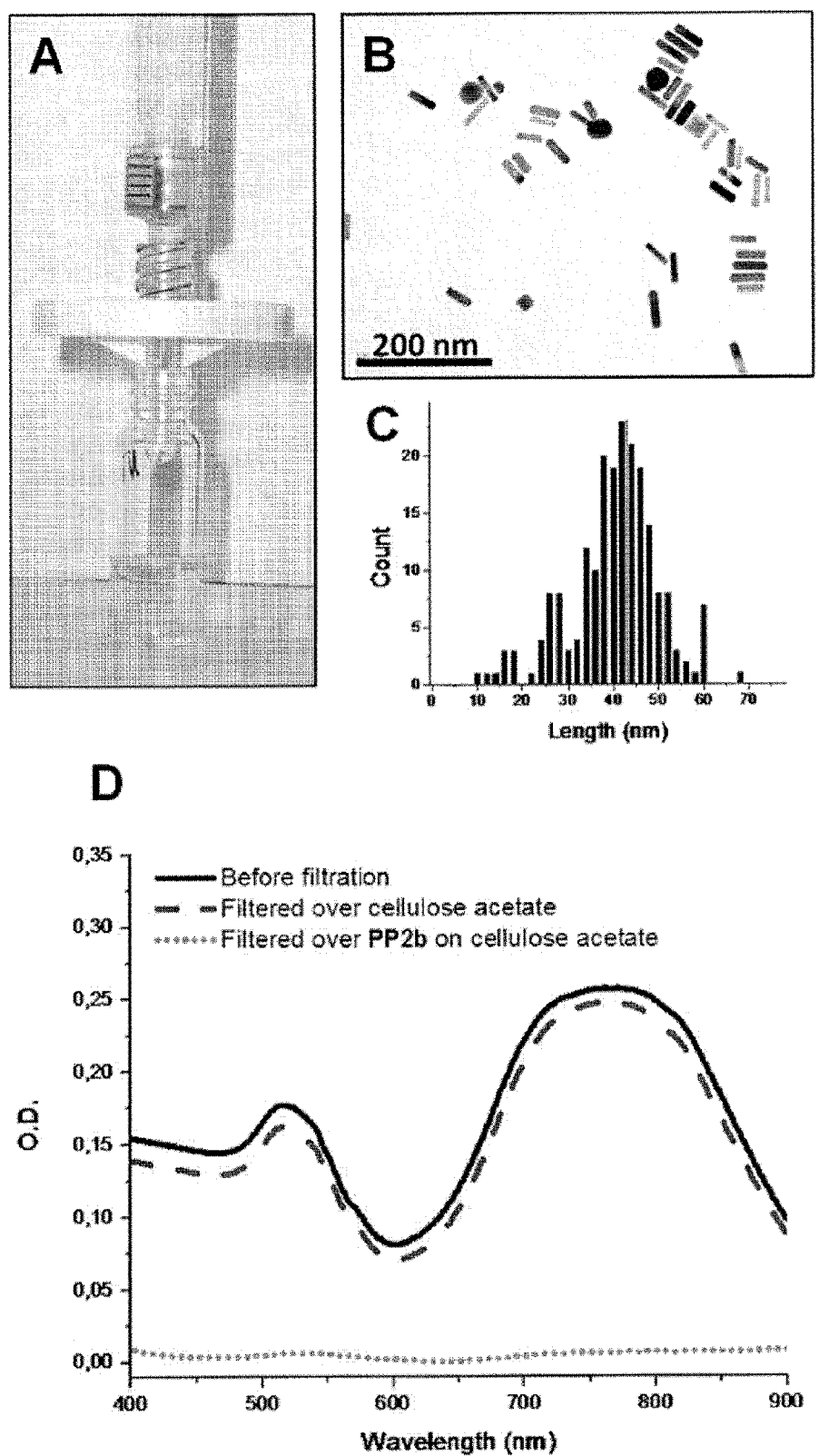

FIG. 19 depicts filtration experiment of Au7. (A) photograph of filtration. (B) Representative TEM image of particles before filtration. (C) corresponding histogram. (D) UV/Vis spectra of Au7 solution before filtration (solid line), after filtration over CA only (dashed line), and after filtration over the Perylene V membrane (dotted line). (PP2b in the figure refers to Perylene V).

Figure 20:
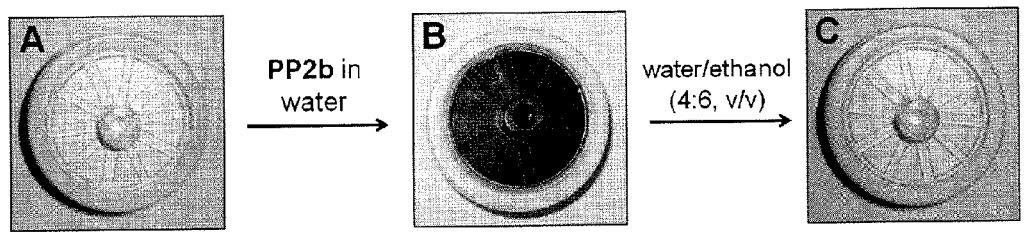

FIG. 20 presents photographs of (A) unused CA syringe filter, (B) Perylene V (=PP2b) supramolecular membrane on the filter, and (C) the same filter after rinsing with water/ethanol mixture.

Figure 21:
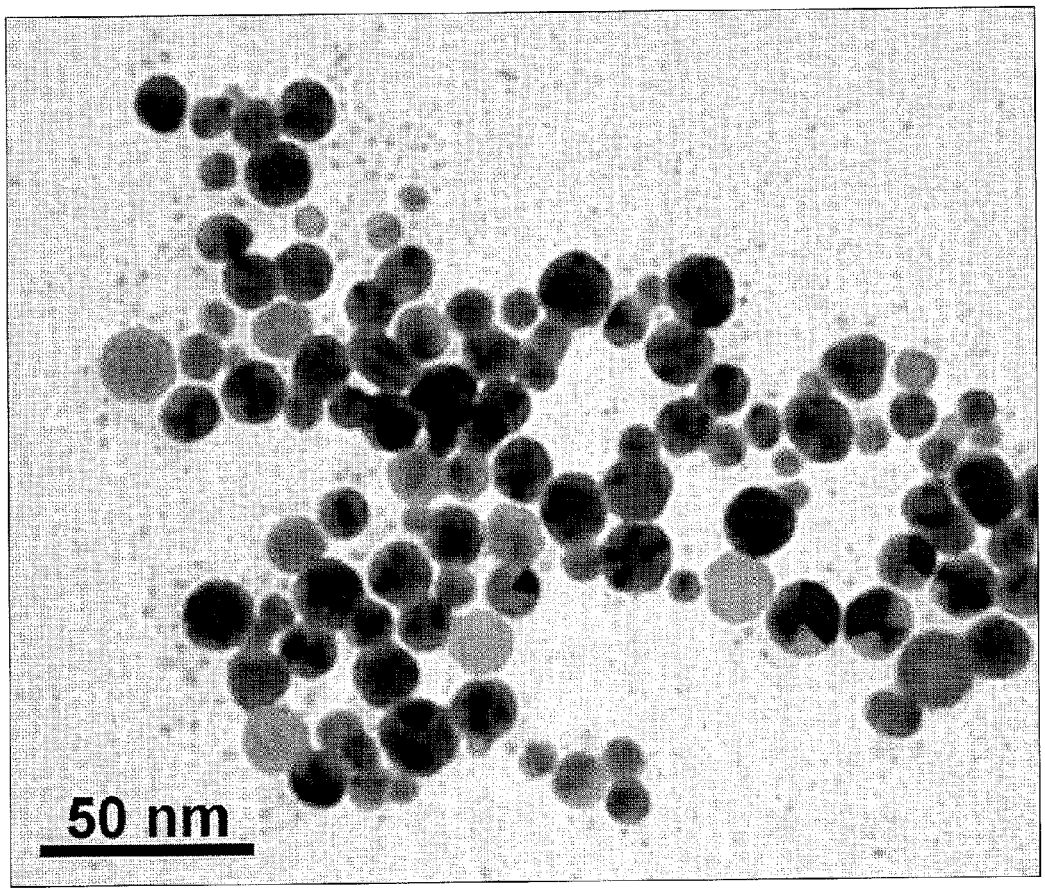
Figure 22:
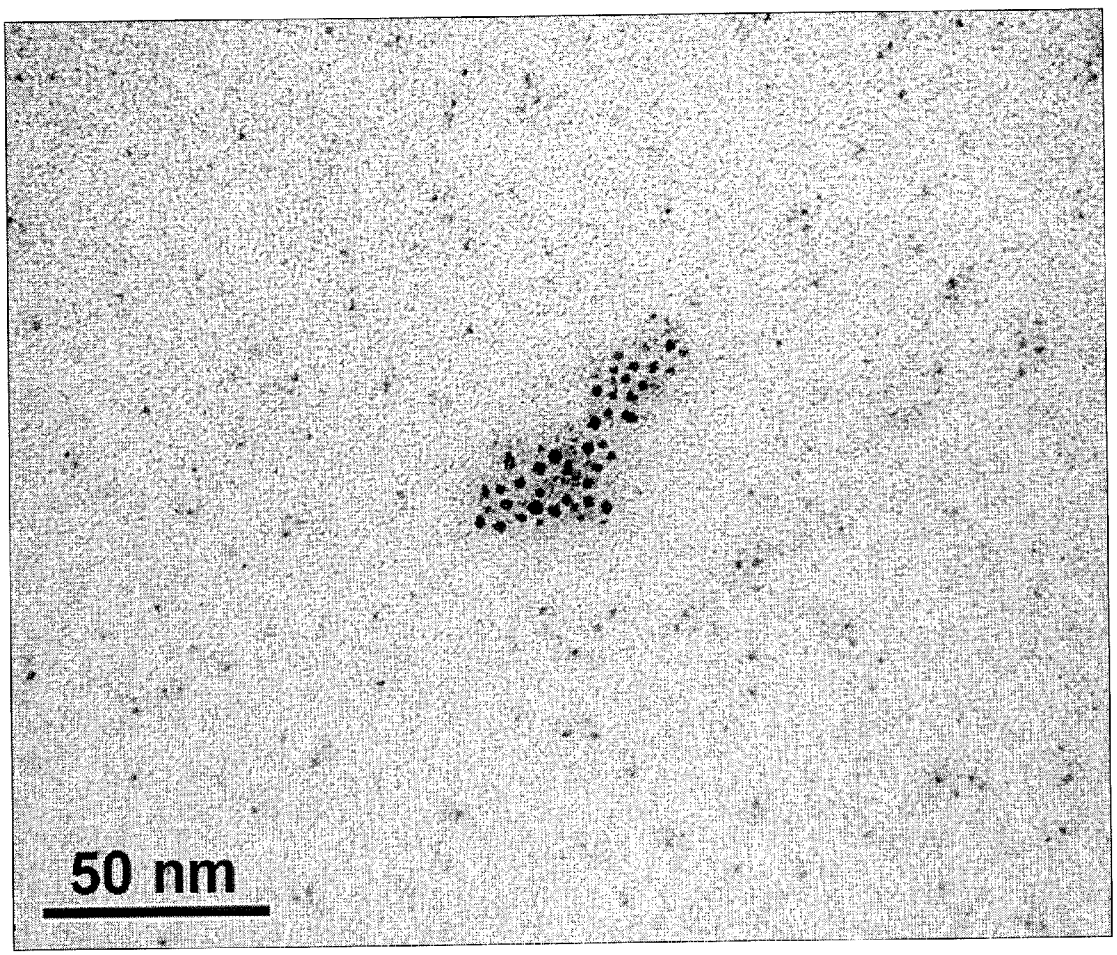
Figure 23:
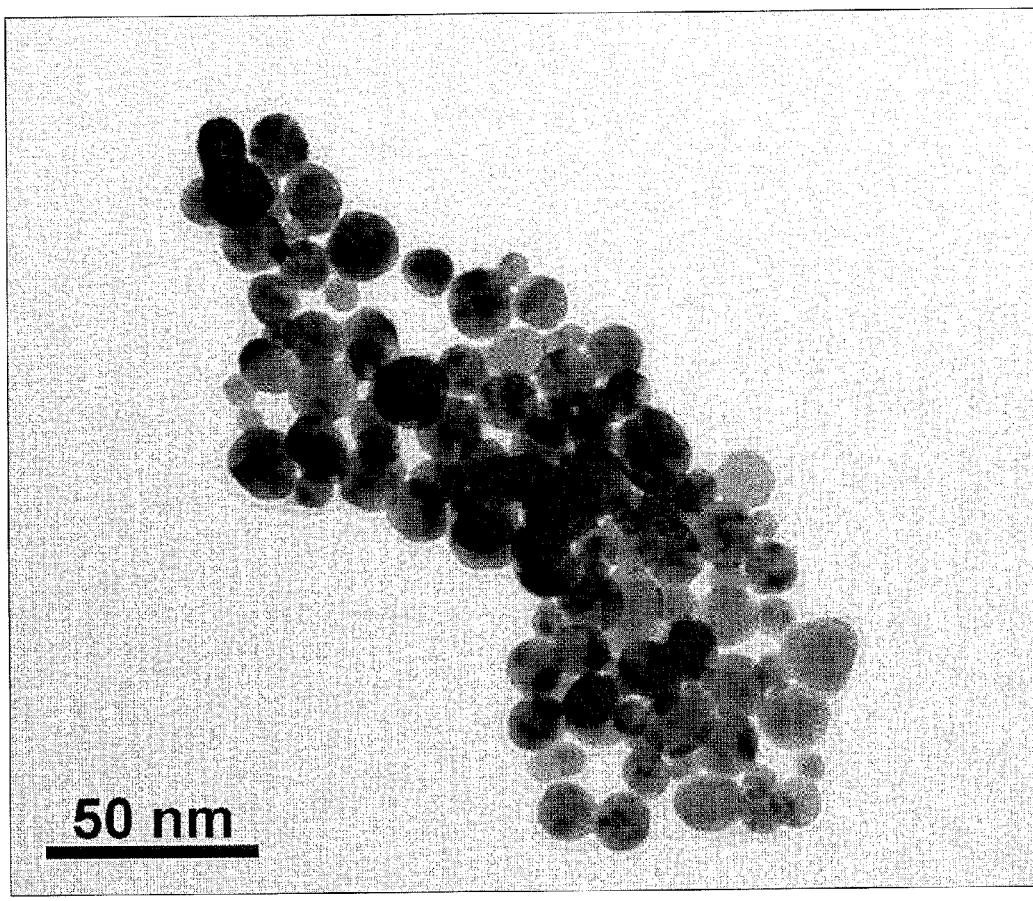
Figure 24:
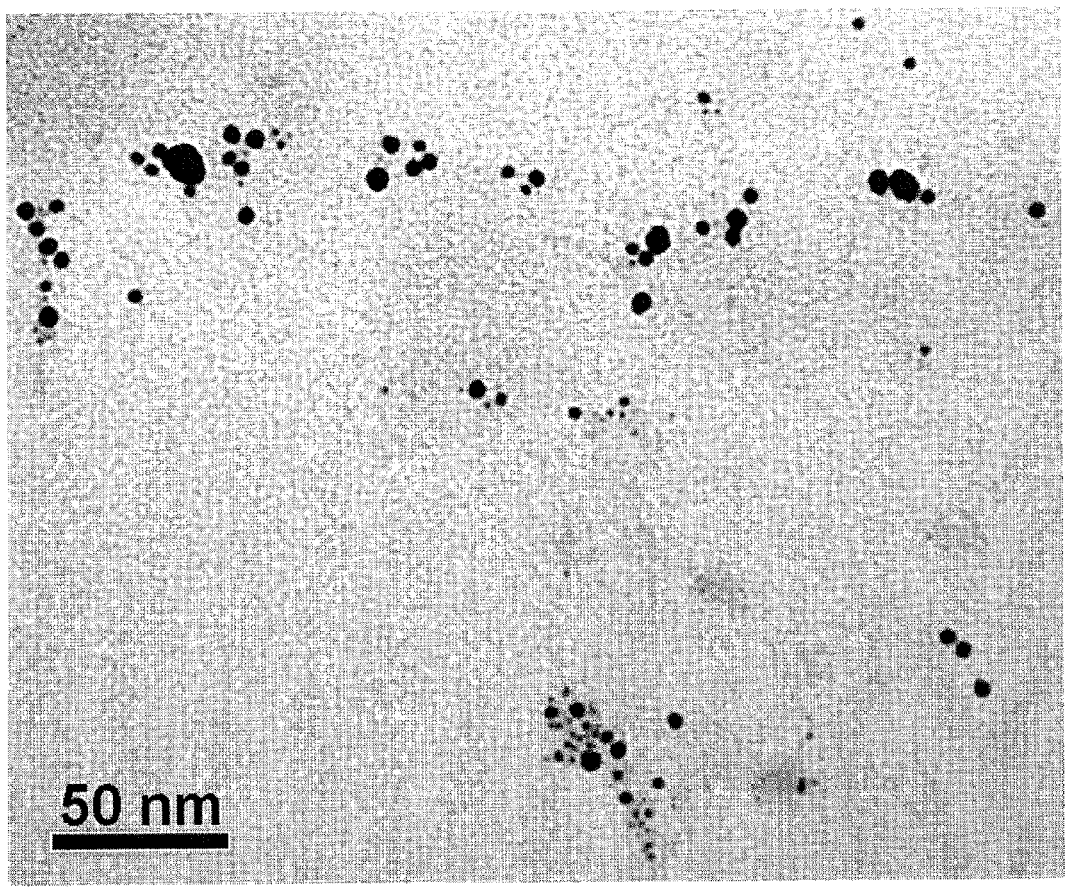
Figure 25:
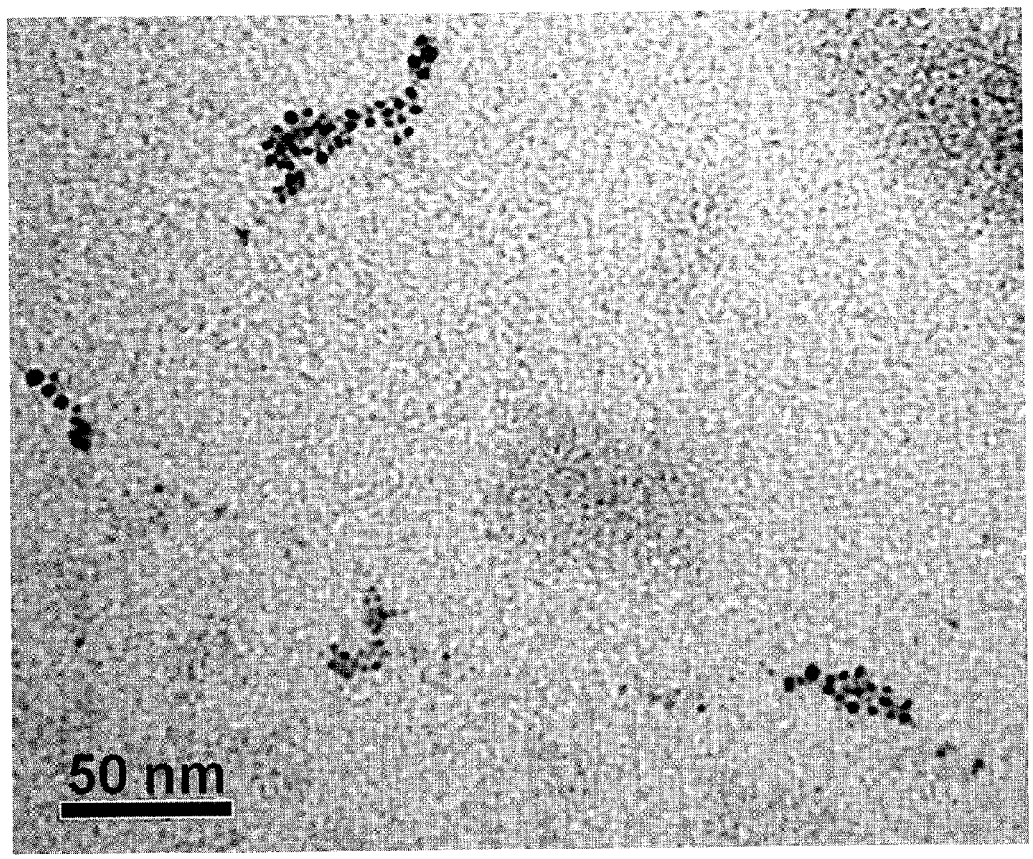
Figure 26:
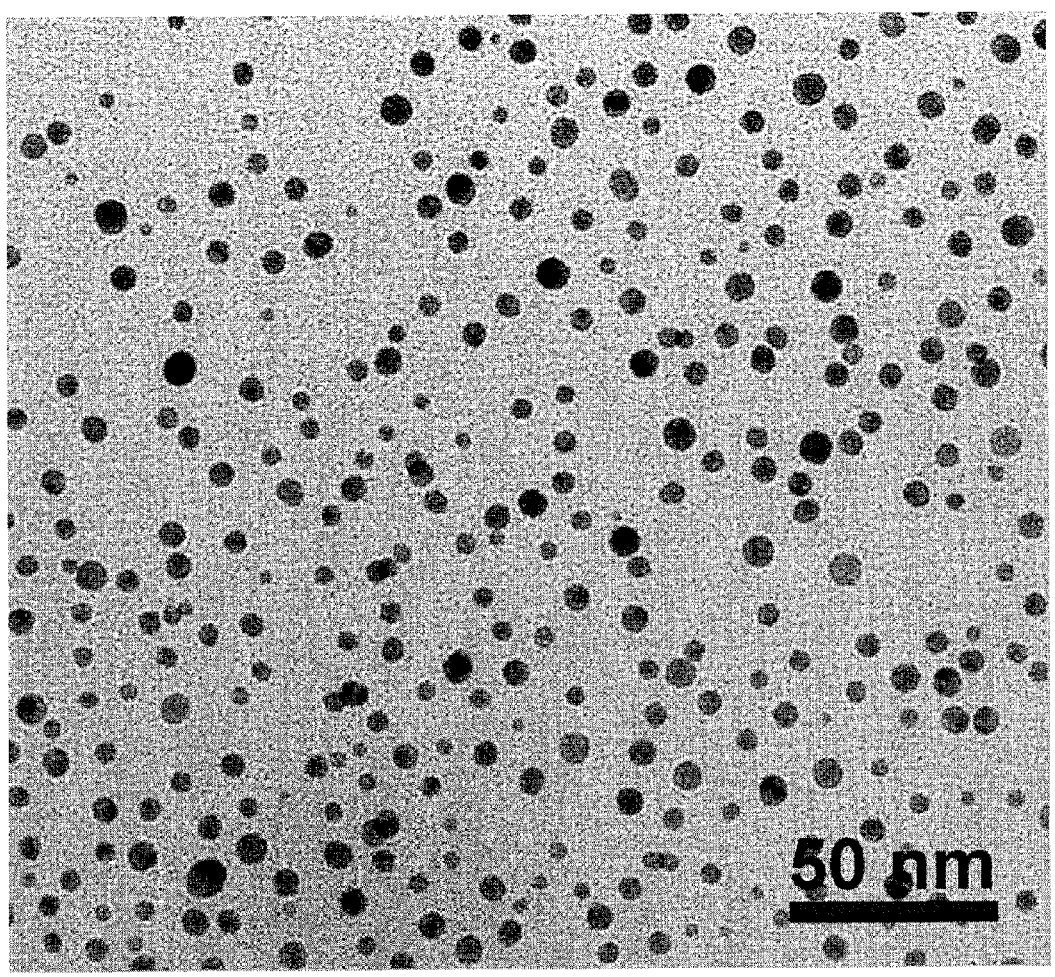
Figure 27:
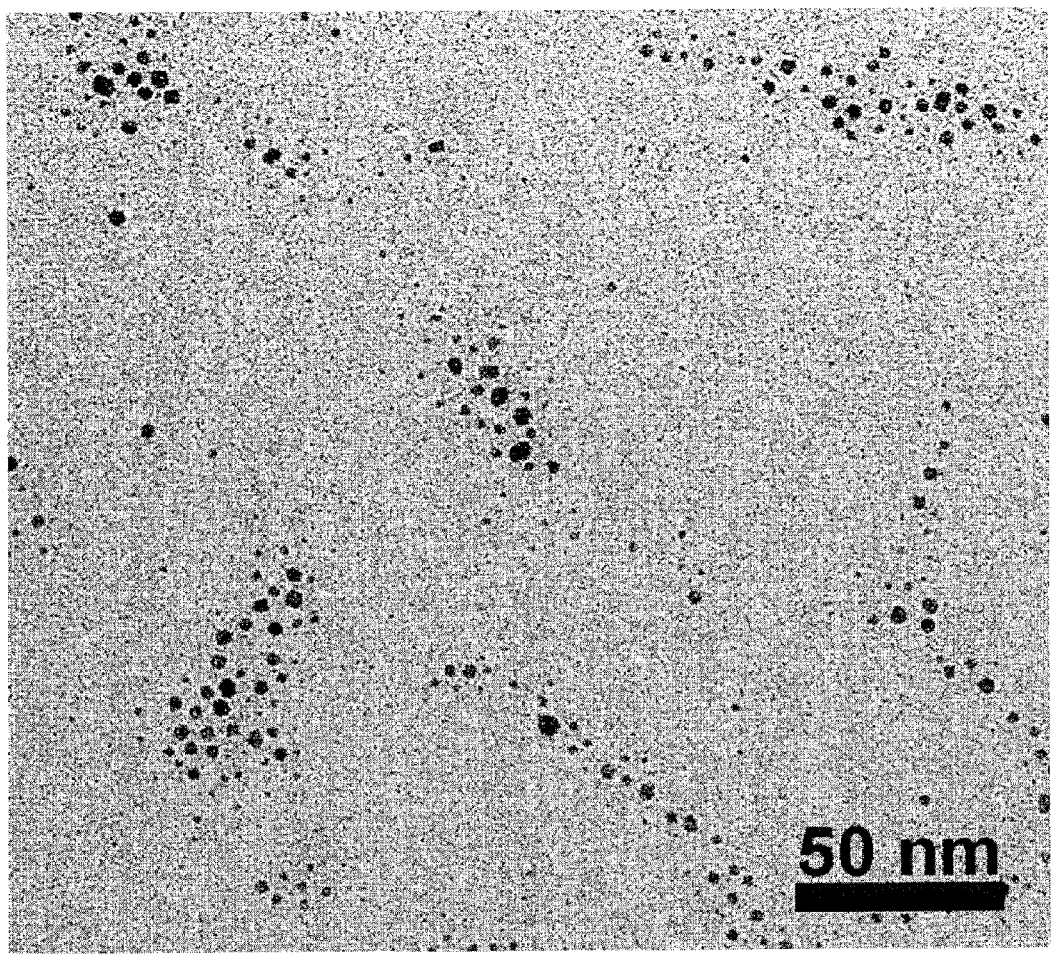
Figure 28:
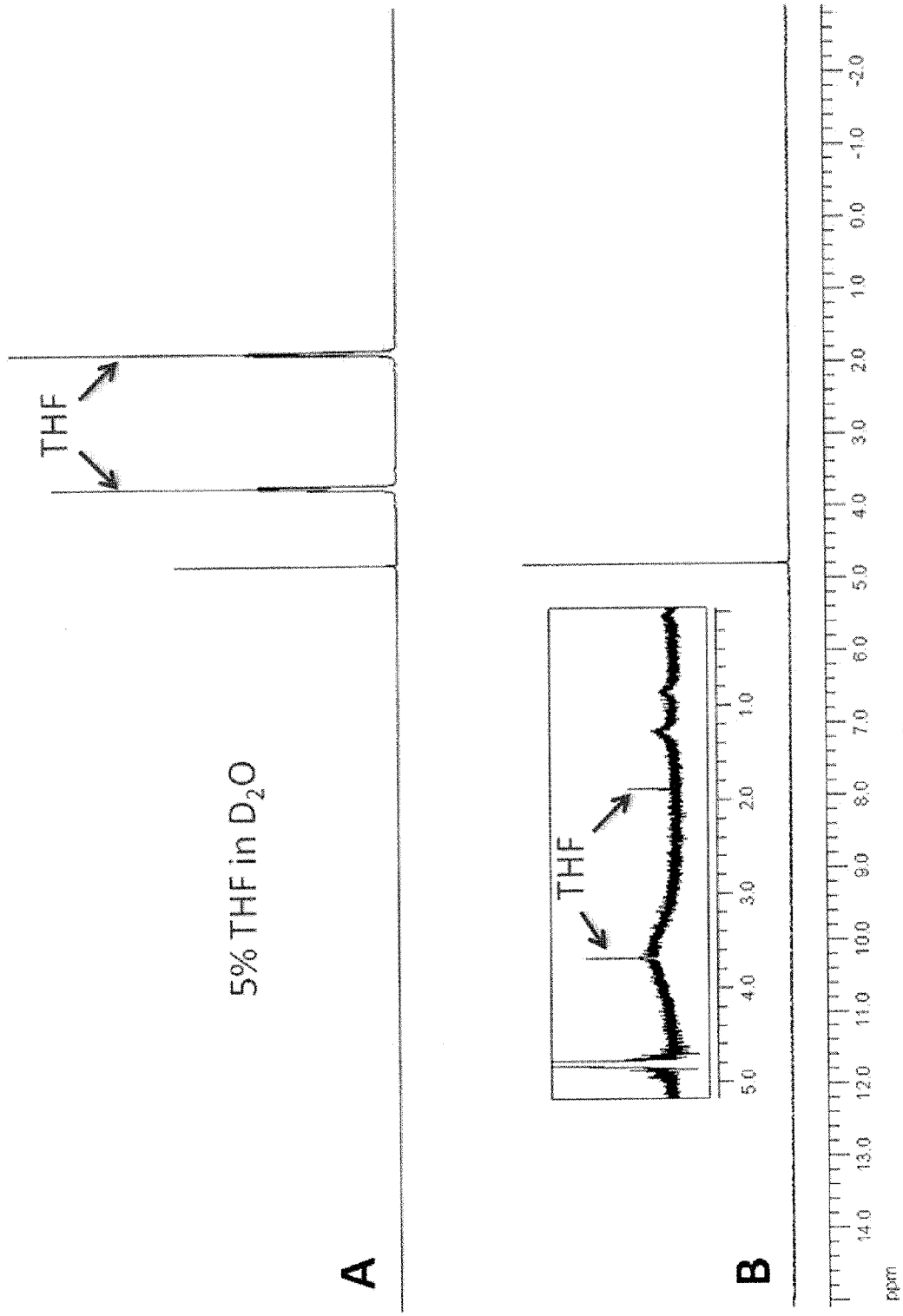

FIG. 21 depicts TEM image of Au3 before filtration.
FIG. 22 depicts TEM image of Au3 filtrate.
FIG. 23 depicts TEM image of Au3 retentate.
FIG. 24 depicts TEM image of Au2 before filtration.
FIG. 25 depicts TEM image of Au2 filtrate.
FIG. 26 depicts TEM image of Au8 before filtration.
FIG. 27 depicts TEM image of Au8 filtrate.
FIG. 28 depicts $^1$H-NMR spectra of Perylene V supramolecular solution (5·$10^{-4}$ M) (A) before and (B) after removal of THF. Inset: Only traces (≤0.01%) of THF are detectable after the removal procedure. Perylene V peaks are strongly broadened and poorly visible due to aggregation.

Figure 29:
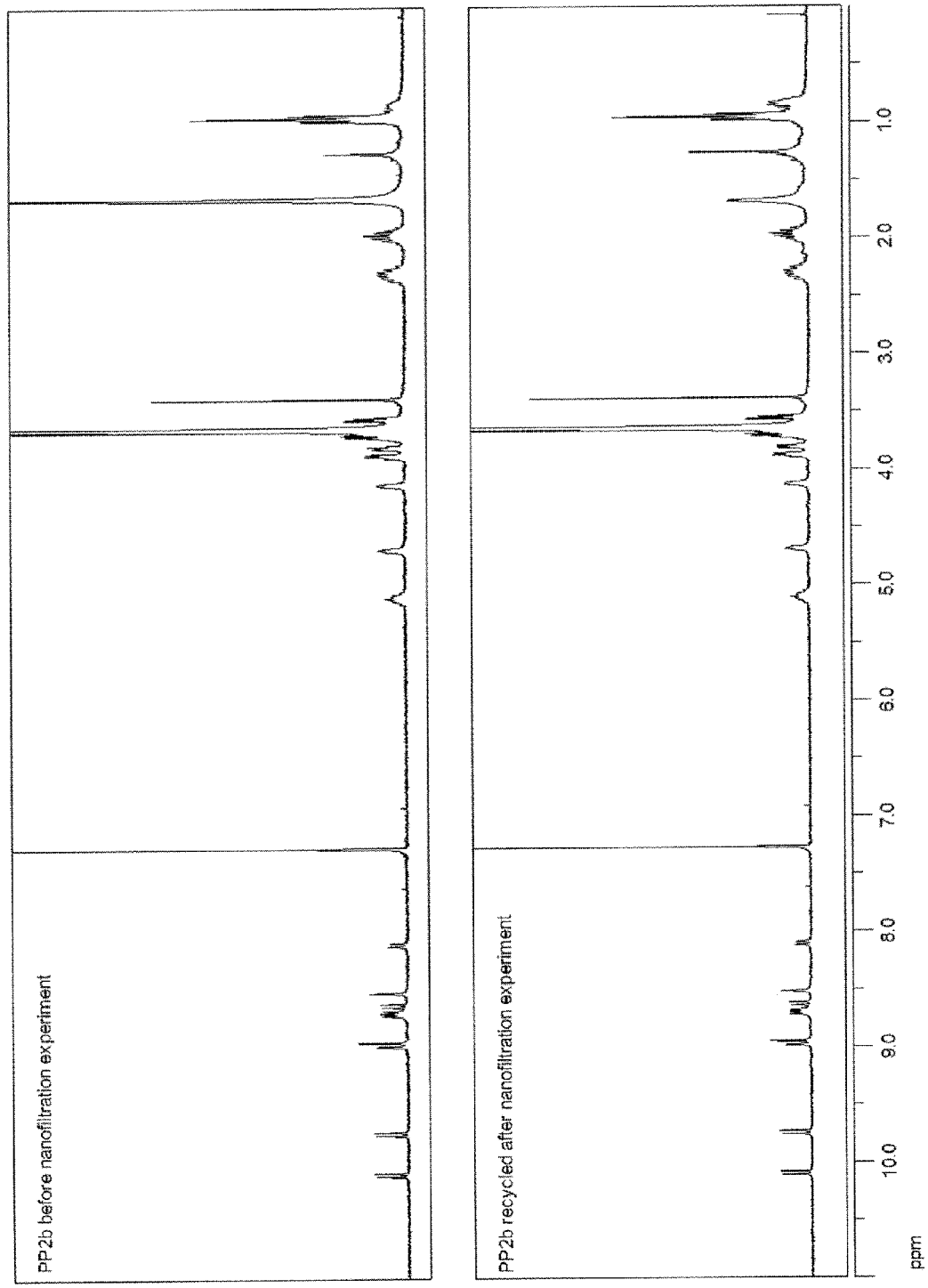

FIG. 29 $^1$H-NMR spectra of Perylene V in CDCl$_3$ before (top) and after recycling (bottom).

Figure 30:
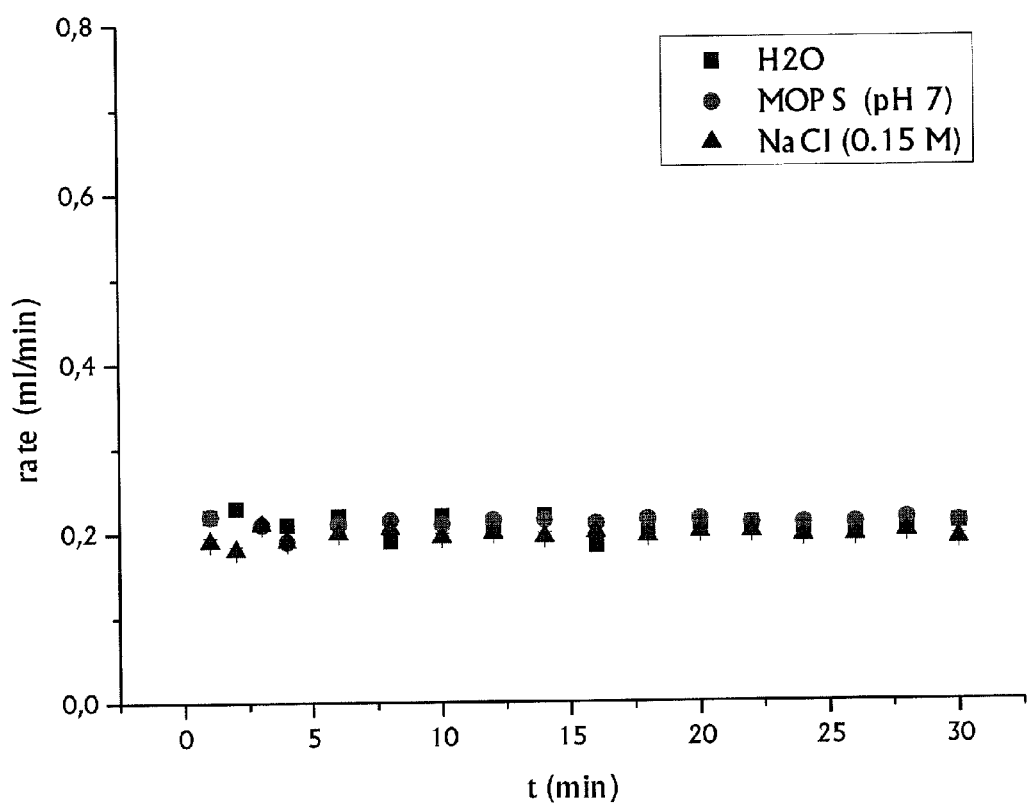

FIG. 30 a scheme presenting the flow rate of H$_2$O, MOPS (((3-(N-morpholino)propanesulfonic acid)) buffer solution (pH=7), and NaCl(aq) at constant pressure (0.4 bar) over a supramolecular membrane composed of 3.7 mg Perylene V deposited on 5.7 cm$^2$ cellulose acetate (thickness: ~12 µm).

Figure 31:
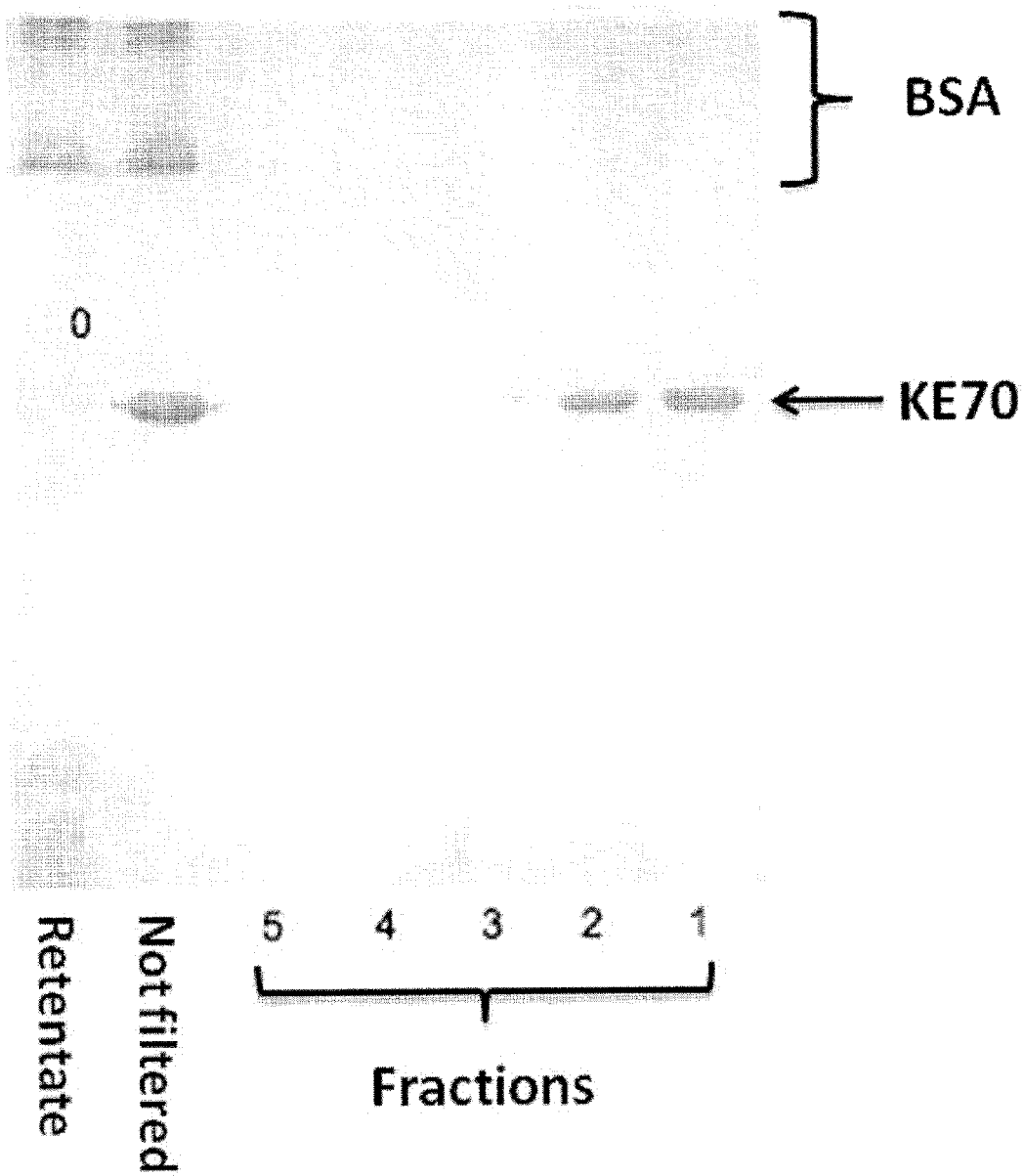

FIG. 31 SDS-PAGE of fractions 1-5, the initial protein solution (not filtered), and the retained proteins isolated from the supramolecular membrane (retentate).

Figure 32:
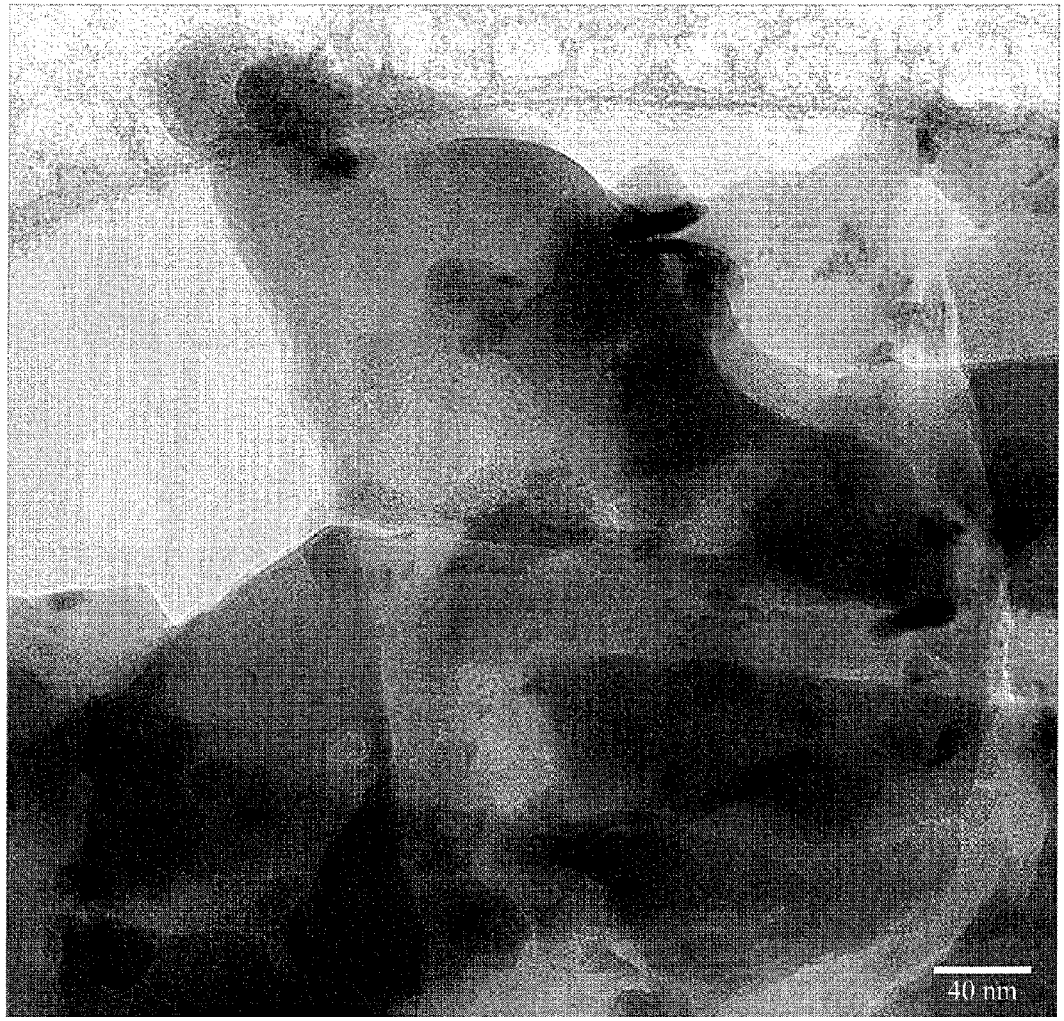

FIG. 32 depicts cryo TEM photograph of Perylene VIII membrane prepared in 5% acetonitrile in water aged 20 hr in 25° C.

Figure 33:
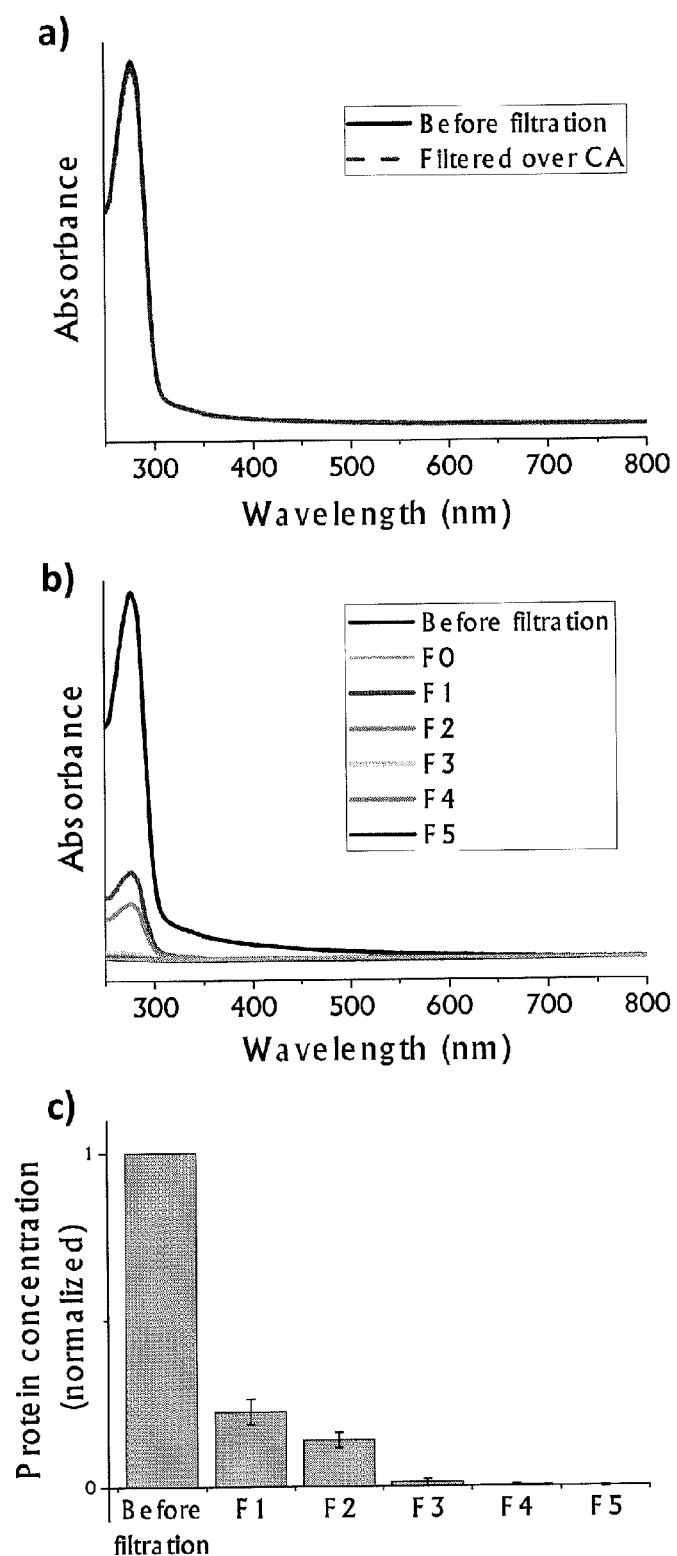

FIG. 33 depicts filtration results of a protein mixture of (1) N-terminal domain of EIIBCA-Bgl residues 2-84(EIIBCA); (2) In silico designed Kemp eliminase (KE70); (3). L-carnitinedehydratase (LCD); (4) L-Fuculose-1-Phosphate Aldolase (Aldolase); (5) Citrate Synthase (CS) and (6) Bovine Serum Albumin (BSA). FIG. 33A depicts UV/Vis spectra of the protein mixture before and after filtration over the pristine cellulose acetate (CA) membrane. FIG. 33B depicts UV/Vis spectra of the protein mixture before filtration through the supramolecular membrane, the filtrate (collected in 5×1.5 ml fractions, F1-F5), and filtered buffer solution as a reference (F0). FIG. 33C depicts the total protein concentration in the filtrate fractions F1-F5 as compared to the feed solution, determined from absorbance at 280 nm. Error bars correspond to the standard deviation of 5 independent filtration experiments.

Figure 34:
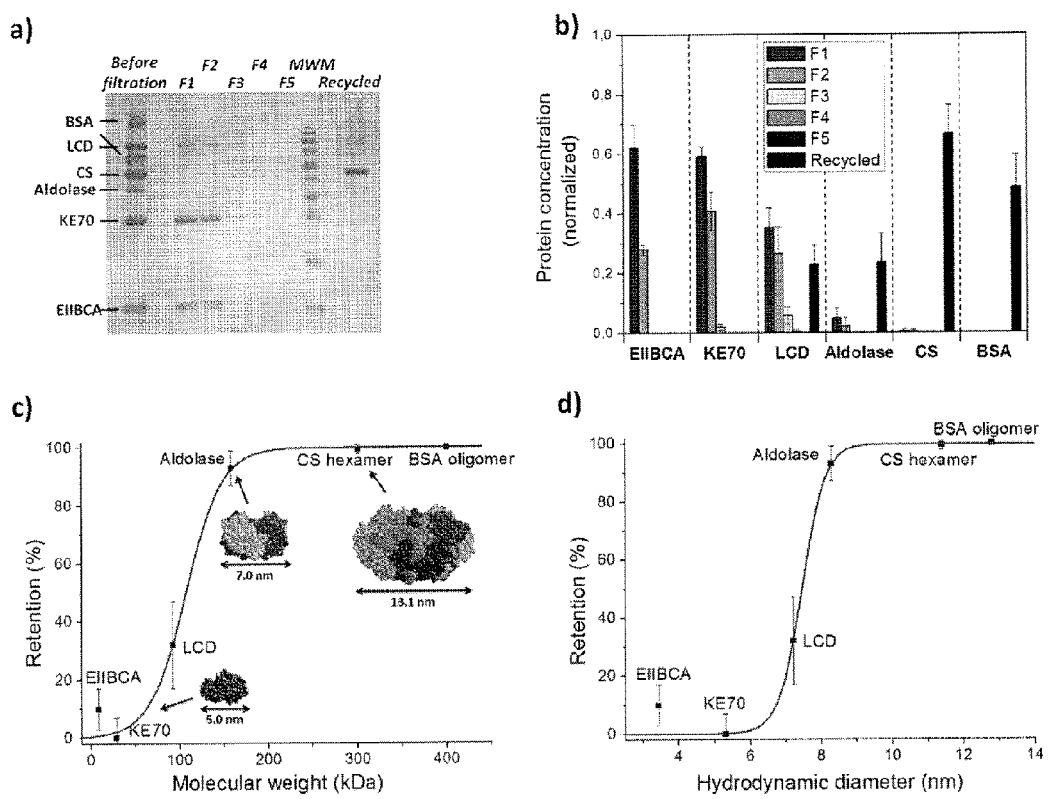

FIG. 34 depicts Separation of protein mixtures over the Perylene V supramolecular membrane. FIG. 34A presents a typical SDS-PAGE used for densitometric quantification of individual protein concentrations. MWM=molecular weight marker (170, 130, 95, 72, 55, 43, 34, 26, 17, 11 kDa). FIG. 34B presents the concentrations of individual proteins in fractions F1-F5 (normalized with respect to the non-filtered solution), and recycled proteins. FIG. 34C presents the protein retention against molecular weight (data points) and sigmoid fit (curve). Protein structures of KE70 (PDB;3Q2D), Aldolase (PDB;1DZU) and CS hexamer (PDB;1NXG) and their long-axis diameters are shown. FIG. 34D presents the dependence of protein retention on the hydrodynamic diameter (data points) and sigmoid fit (curve). All error bars represent the standard deviation of 5 independent filtration experiments. (PDB refers to protein data bank).

Figure 35:
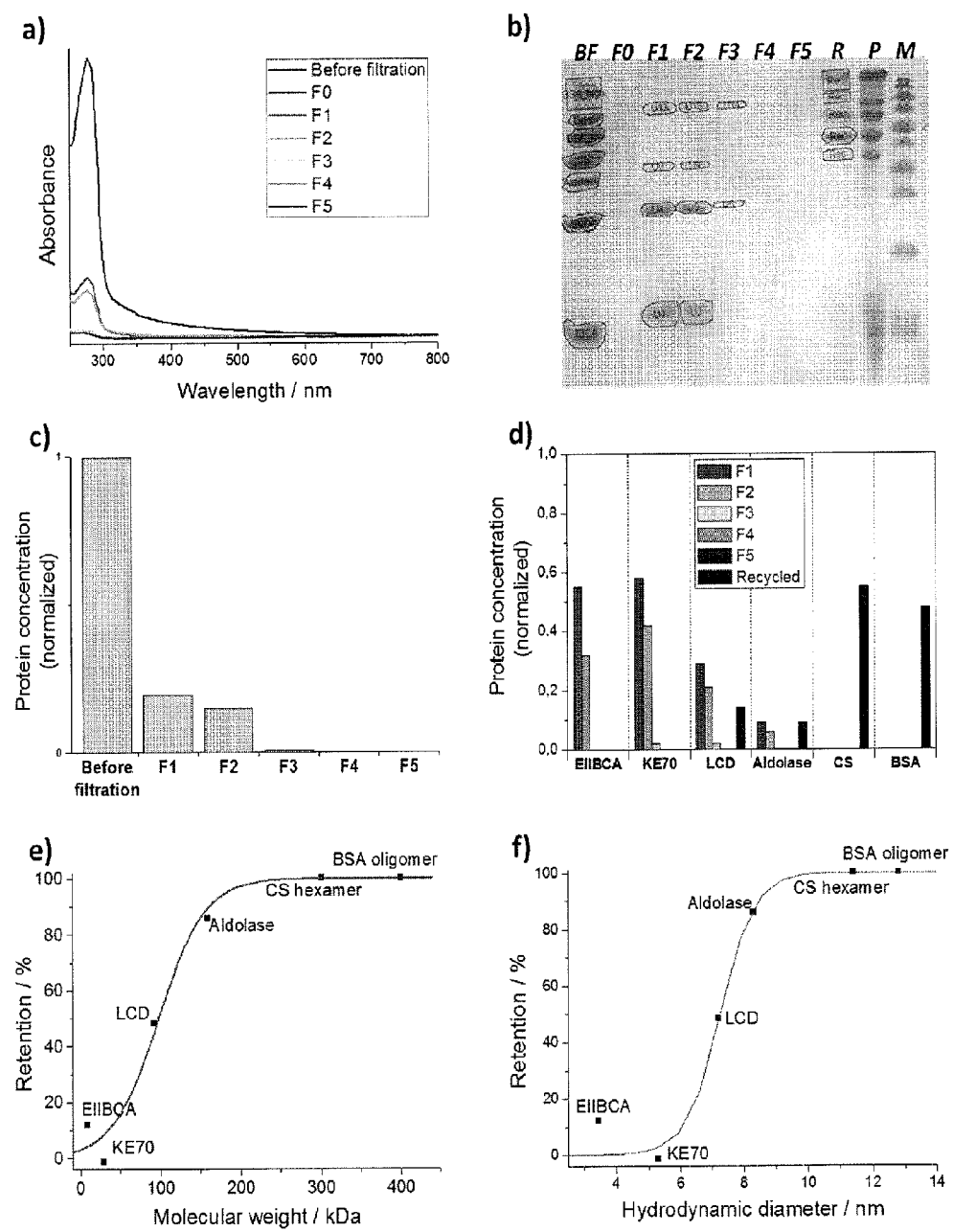

FIG. 35 depicts filtration of proteins over a supramolecular membrane fabricated from recycled Perylene V. FIG. 35A depicts UV/Vis spectra of the protein mixture before filtration, and filtered fractions. FIG. 35B depicts SDS-PAGE of the filtration experiment. BF=Before filtration, M=Molecular weight marker (170, 130, 95, 72, 55, 43, 34, 26, 17, 11 kDa), R=Recycled, P=Pellet (highly concentrated). Selected areas for densitometric protein quantification are marked. FIG. 35C depicts total protein concentration in the filtrate fractions F1-F5 as compared to the feed solution. FIG. 35D depicts protein concentrations (normalized with respect to the non-filtered solution) of fractions F1-F5, and recycled proteins. FIG. 35E depicts a plot of protein retention against molecular weight (data points) and sigmoid fit (curve). FIG. 35F depicts a plot of protein retention against hydrodynamic diameter (data points) and sigmoid fit (curve).

Figure 36:
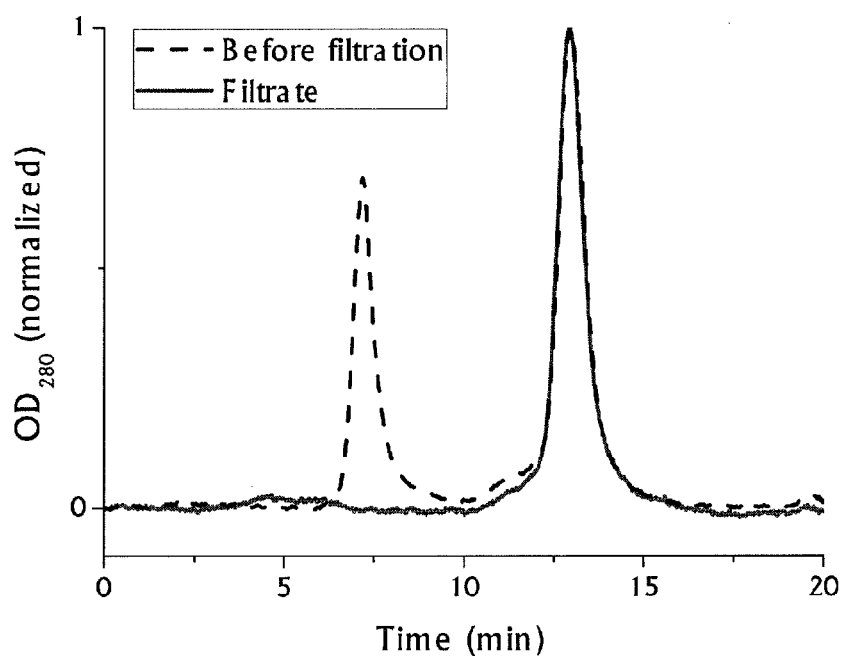

FIG. 36 presents gel filtration chromatogram of a mixture of BSA oligomers and monomers before filtration (dashed line), and its filtrate (black line). Filtration quantitatively removes BSA oligomers (≥400 kDa, retention time: 7 min) from the mixture. Smaller BSA aggregates (retention time:

11-12 min) are removed as well. The filtrate contains pure monomeric proteins (~67 kDa, retention time: 13 min).

Figure 37:
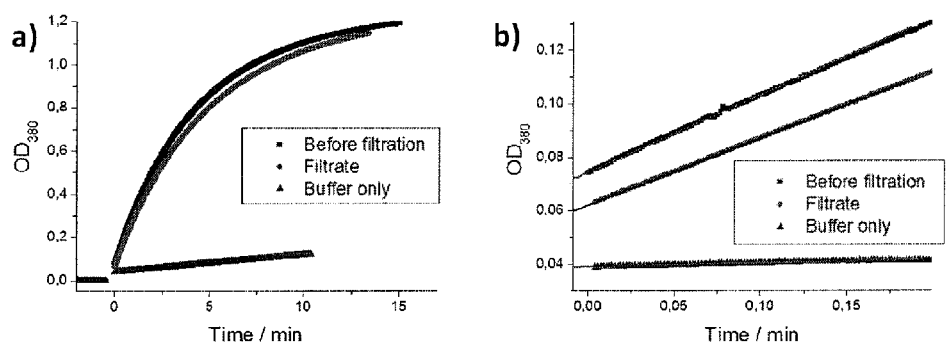

FIG. 37 presents kinetics of the KE70 activity before filtration, after filtration, and of neat buffer solution, as revealed by the change in absorbance at 380 nm, following addition of 5-Nitrobezisoxazole (at t=0 min). FIG. 37A: Full experiment. FIG. 37B: Linear range of enzyme kinetics and regression lines.

Figure 38:
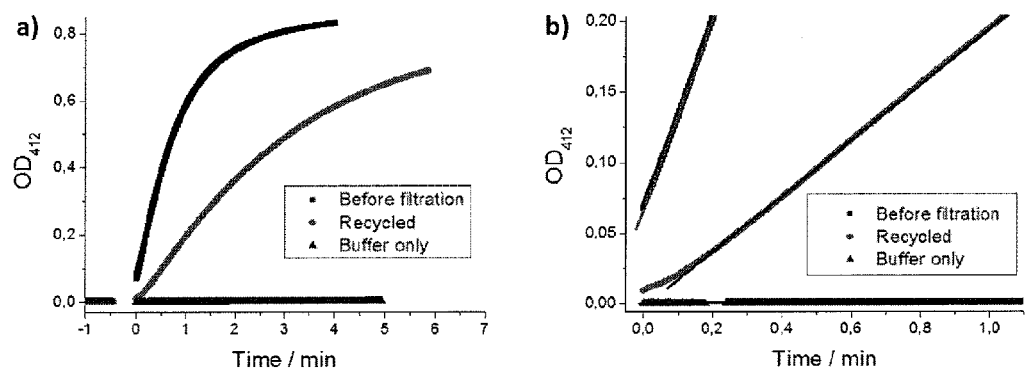

FIG. 38 presents kinetics of the CS activity before filtration, after filtration and recycling from the membrane, and of neat buffer solution, as revealed by the change in absorbance at 412 nm, following addition of Oxaloacetate (at t=0 min). FIG. 38A: Full experiment. FIG. 38B: Linear range of enzyme kinetics and regression lines.

Figure 39:
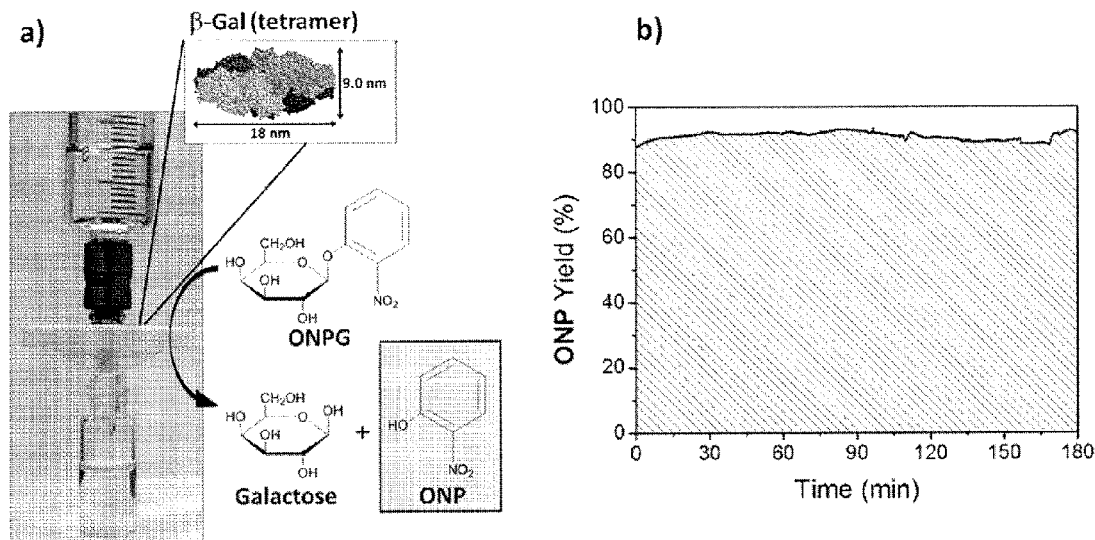

FIG. 39 depicts heterogeneous biocatalysis in the supramolecular membrane using immobilized-Gal. FIG. 39A presents hydrolysis of ONPG into Galactose and ONP. FIG. 39B presents the yield of ONP as a function of time during several hours of continuous flux of substrate.

Figure 40:
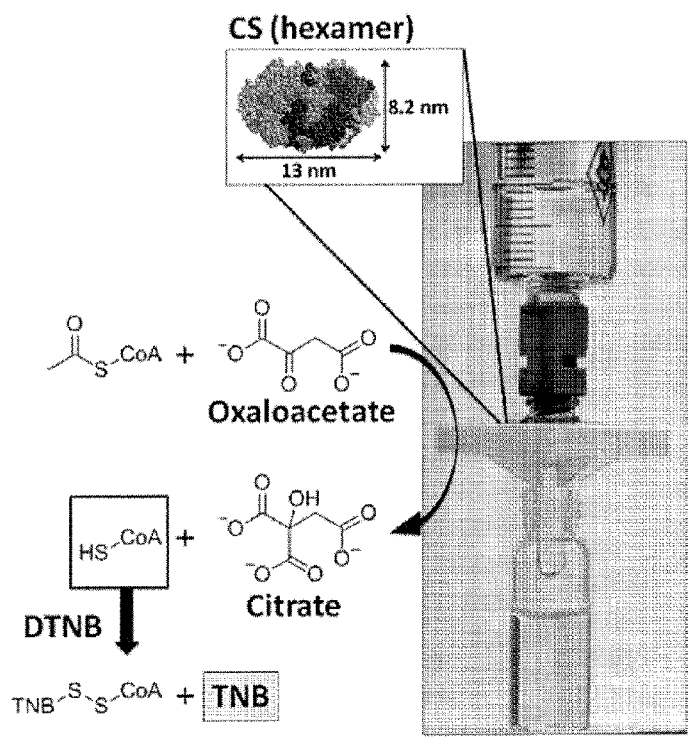

FIG. 40 presents conversion of Oxaloacetate and Acetyl-CoA into Citrate and HS-CoA over CS immobilized in a Perylene V supramolecular membrane. HS-CoA reacts with DTNB in the assay solution to release the indicator of the reaction, TNB ($\lambda_{max}$=412 nm). The color change from clear reactant feed solution to yellow filtrate indicates biocatalytic activity of the immobilized enzymes.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention is directed to (i) a noncovalent self-assembled porous membrane comprising a perylene diimide supramolecular structure; (ii) a noncovalent self-assembled porous membrane comprising a perylene diimide supramolecular structure; providing chromatography medium for size-selective separation; (iii) a noncovalent self-assembled porous chiral membrane comprising a chiral perylene diimide supramolecular structure providing a chiral separation for chiral molecules (nanometer and subnanometer size) (iv) a method of filtration, purification, optimization and/or separation of nano-materials (nanoparticles, biomolecules) using the noncovalent self-assembly perylene based porous membrane of this invention; (v) a method of chiral separation using chiral membrane comprising a chiral perylene diimide supramolecular structure; (v) a method of preparing the noncovalent self-assembly perylene based porous membrane; (vi) a method of recycling the membrane of this invention; (vii) a biocatalytic membrane comprising the membrane of this invention and an enzyme wherein the enzyme is immobilized within the membrane; and (viii) a method of heterogenous biocatalysis using the biocatalytic membrane of this invention; comprising perylene diimide monomeric unit of formula I-XIV.

In one embodiment, this invention is directed to noncovalent self-assembled porous membrane and methods of use thereof comprising a supramolecular structure of perylenes, perylene diimide, pyrenes, or other extended aromatics wherein said supramolecular structure is formed by self assembly of the perylenes, pyrenes, or other extended aromatics. In one embodiment, this invention is directed to noncovalent self-assembled porous membrane and methods of use thereof comprising a supramolecular structure of perylene diimide compounds of this invention. The self assembled supramolecular structure is formed by noncovalent interactions such as hydrogen bonds, π-π interactions and/or hydrophoboic interactions between the perylene groups or the pyrene groups. In another embodiment, the monomer unit of the supramolecular structure comprises between one to five covalently attached perylene groups or pyrene groups. In another embodiment, the monomer unit of the supramolecular polymer structures comprises of between one to five covalently attached perylene diimide groups or pyrene groups comprising a PEG (polyethylene glycol) side chains linked by an unsaturated bridge. In another embodiment, the PEG side chains comprise between 17-21 repeating units. In another embodiment, the PEG side chains comprise between 18-22 repeating units. In another embodiment, the perylenes or pyrenes comprise different lengths of PEG size chains, wherein the average lengths is of the side chains is between 17-22 or 18-22 repeating units.

Figure 5A:
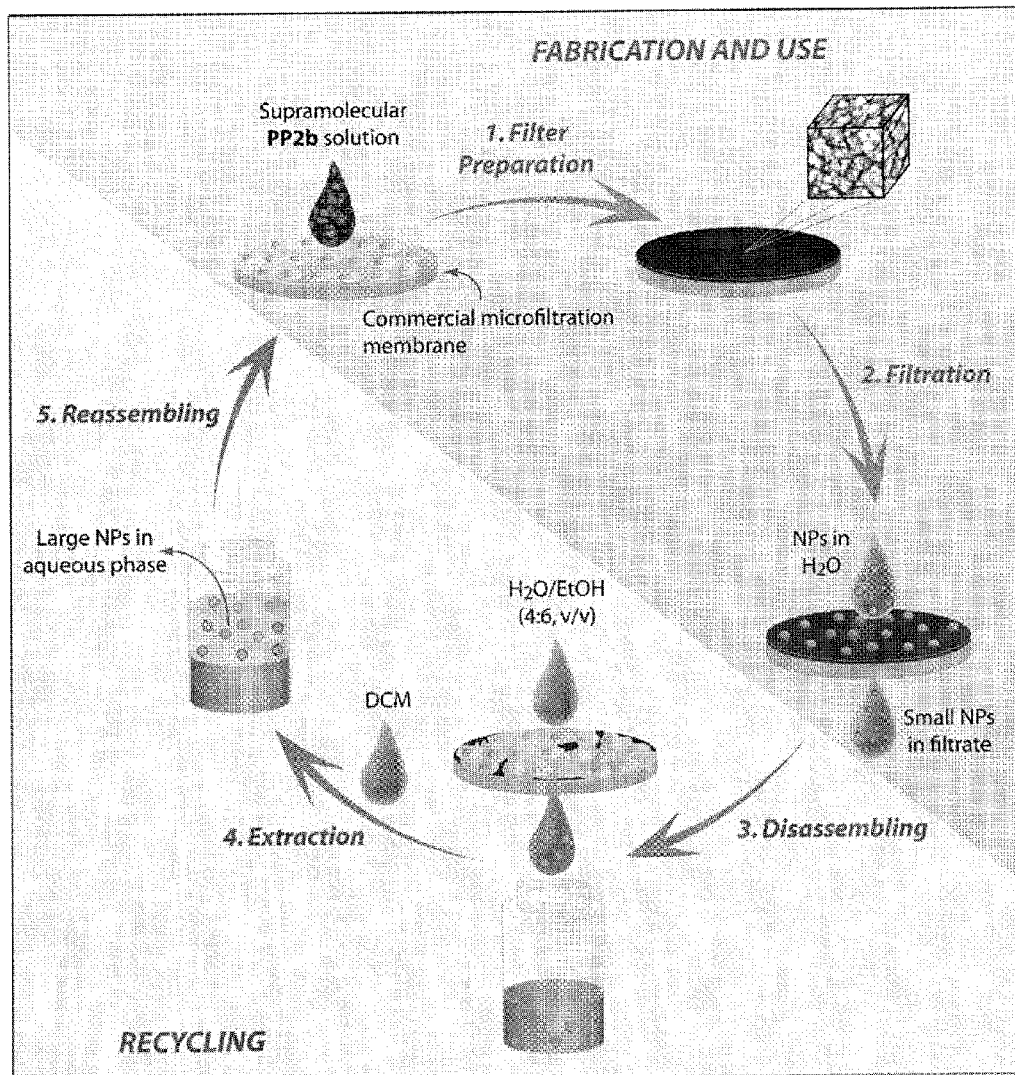
FIGS. 5A-5B depict schemes of fabrication, use, and recycling of the supramolecular membrane of this invention.
Figure 5B:
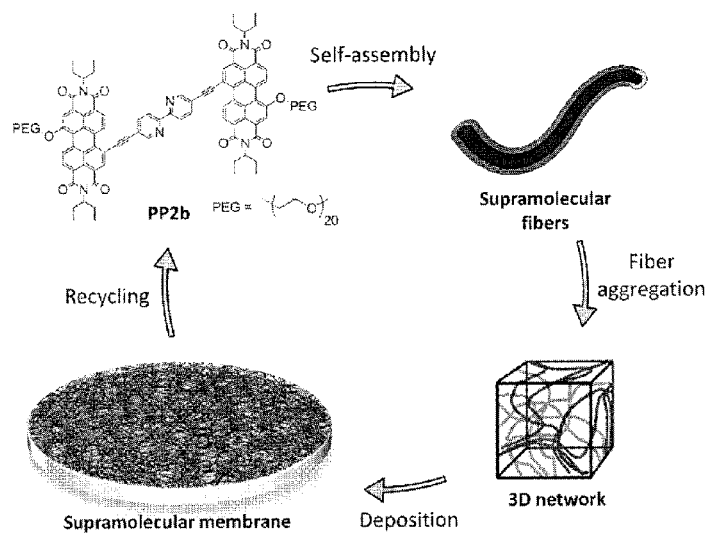

Hydrophobic interactions between large nonpolar groups of amphiphilic molecules in aqueous solution can be remarkably strong, driving self-assembly towards very stable supramolecular systems. The monomer unit of the supramolecular structure of this invention includes two perylene-3,4,9,10-tetracarboxylic acid diimide (PDI) units. The PDI monomeric unit self-assembles in aqueous media into a robust three dimensional (3D) fibrous network, resulting in a stable and multiple-stimuli-responsive material (FIG. 5A-5B).

In another embodiment, the membrane of this invention is based on very strong hydrophobic interactions, preventing exposure of the hydrophobic moieties to bulk water. It is also enclosed by a shell of polyethylene glycol (PEG) groups (Error! Reference source not found.), which are known to preserve the native structure of proteins and resist undesired biomolecule adsorption. Thus, in water, the membrane of this invention is robust and potentially biocompatible.

In one embodiment, this invention is directed to noncovalent self-assembled porous membrane and methods of use thereof comprising a supramolecular structure comprising perylene, a salt thereof or a metal complex thereof as a monomeric unit wherein said perylene is represented by the structure of formula I:

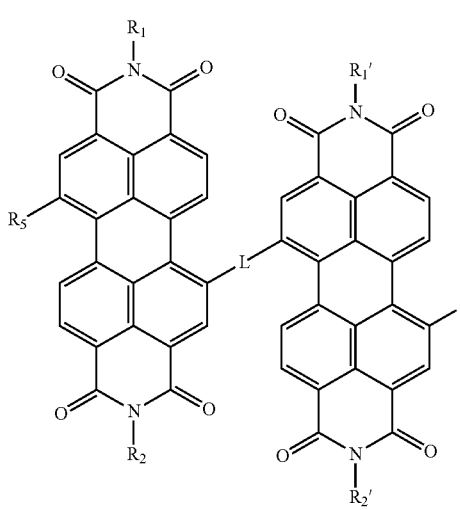

wherein $R_1$ and $R_1'$ are independently $[(CH_2)_nO]_oCH_3$, $[(CH_2)_nC(O)O]_oCH_3$, $[(CH_2)_nC(O)NH]_oCH_3$, $[(CH_2)_nCH_2\!=\!CH_2]_oCH_3$, $[(CH_2)_nCH\!=\!CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2\!=\!CH_2]_oCH_3$, $[(alkylene)_nCH\!=\!CH]_oCH_3$, $[(alkylene)_nNH]_oCH_3$, $(C_1\text{-}C_{32})$alkyl, $(C_3\text{-}C_8)$cycloalkyl, aryl, heteroaryl, chiral group, $(C_1\text{-}C_{32})$alkyl-COOH, $(C_1\text{-}C_{32})$alkyl-Si-A, or $[C(O)NHR_3NH]_pH$ wherein said aryl or heteroaryl groups are optionally substituted by 1-3 groups comprising halide, CN, $CO_2H$, OH, SH, $NH_2$, $CO_2$—$(C_1\text{-}C_6$ alkyl) or O—$(C_1\text{-}C_6$ alkyl); wherein A comprises three same or different of the following substituents Cl, Br, I, $O(C_1\text{-}C_8)$alkyl or $(C_1\text{-}C_8)$alkyl; and wherein $R_3$ in said $[C(O)NHR_3NH]_pH$ is an alkyl, haloalkyl, hydroxyalkyl, hydroxyl, aryl, phenyl, alkylphenyl, alkylamino and independently the same or different when p is larger than 1;

$R_2$ and $R_2'$ are independently $[(CH_2)_qO]_rCH_3$, $[(CH_2)_qC(O)O]_rCH_3$, $[(CH_2)_qC(O)NH]_rCH_3$, $[(CH_2)_qCH_2\!=\!CH_2]_rCH_3$, $[(CH_2)_qCH\!=\!CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2\!=\!CH_2]_rCH_3$, $[(alkylene)_qCH\!=\!CH]_rCH_3$, $[(alkylene)_qNH]_rCH_3$, $(C_1\text{-}C_{32})$alkyl, $(C_3\text{-}C_8)$cycloalkyl, aryl, heteroaryl, chiral group, $(C_1\text{-}C_{32})$alkyl-COOH, $(C_1\text{-}C_{32})$alkyl-Si-A, or $[C(O)NHR_4NH]_sH$ wherein said aryl or heteroaryl groups are optionally substituted by 1-3 groups comprising halide, CN, $CO_2H$, OH, SH, $NH_2$, $CO_2$—$(C_1\text{-}C_6$ alkyl) or O—$(C_1\text{-}C_6$ alkyl); wherein A comprises three same or different of the following substituents Cl, Br, I, $O(C_1\text{-}C_8)$alkyl or $(C_1\text{-}C_8)$alkyl; and wherein $R_4$ in said $[C(O)NHR_4NH]_sH$ is an alkyl, haloalkyl, hydroxyalkyl, hydroxyl, aryl, phenyl, alkylphenyl, alkylamino and independently the same or different when s is larger than 1;

$R_5$ and $R_5'$ are independently H, —$OR_x$ where $R_x$ is $C_1\text{-}C_6$ alkyl or $[(CH_2)_qO]_rCH_3$, $[(CH_2)_qC(O)O]_rCH_3$, $[(CH_2)_qC(O)NH]_rCH_3$, $[(CH_2)_qCH_2\!=\!CH_2]_rCH_3$, $[(CH_2)_qCH\!=\!CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2\!=\!CH_2]_rCH_3$, $[(alkylene)_qCH\!=\!CH]_rCH_3$, $[(alkylene)_qNH]_rCH_3$, aryl, heteroaryl, $C\!\equiv\!C\!-\!R_7$, $CH\!=\!CR_8R_9$, $NR_{10}R_{11}$, chiral group, amino acid, peptide or a saturated carbocyclic or heterocyclic ring wherein said saturated heterocyclic ring or heteroaryl contains at least one nitrogen atom and $R_5$ or $R_5'$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1\text{-}C_6$ alkyl) or O—$(C_1\text{-}C_6$ alkyl);

$R_7$ is H, halo, $(C_1\text{-}C_{32})$alkyl, aryl, $NH_2$, alkyl-amino, COOH, C(O)H, alkyl-COOH heteroaryl, $Si(H)_3$ or $Si[(C_1\text{-}C_8)alkyl]_3$ wherein said aryl or heteroaryl groups are optionally substituted by 1-3 groups comprising halide, aryl, heteroaryl, CN, $CO_2H$, OH, SH, $NH_2$, $CO_2$—$(C_1\text{-}C_6$ alkyl) or O—$(C_1\text{-}C_6$ alkyl);

$R_8$, $R_9$, $R_{10}$ and $R_{11}$ are independently H, $(C_1\text{-}C_{32})$alkyl, aryl, $NH_2$, alkyl-amino, COOH, C(O)H, alkyl-COOH or heteroaryl wherein said aryl or heteroaryl groups are optionally substituted by 1-3 groups comprising halide, CN, $CO_2H$, OH, SH, $NH_2$, $CO_2$—$(C_1\text{-}C_6$ alkyl) or O—$(C_1\text{-}C_6$ alkyl);

L is a linker;

n is an integer from 1-5;

o is an integer from 1-100;

p is an integer from 1-100;

q is an integer from 1-5;

r is an integer from 1-100; and s is an integer from 1-100;

wherein if $R_5$ and $R_5'$ independently are chiral groups, amino acid or peptide; said membrane will form a chiral membrane.

In one embodiment, this invention is directed to noncovalent self-assembled porous membrane and methods of use thereof comprising a supramolecular structure comprising perylene, a salt thereof or a metal complex thereof as a monomeric unit wherein said perylene is represented by the structure of formula II:

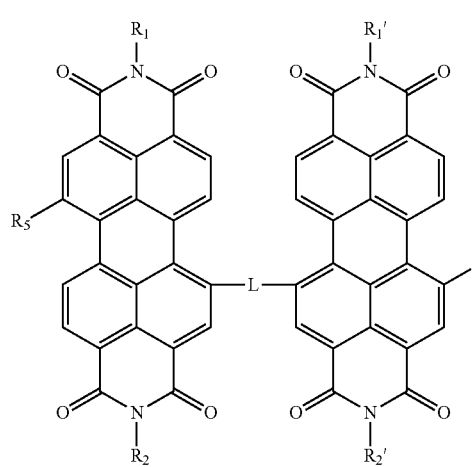

wherein $R_1$, $R_2$, $R_1'$, $R_2'$, $R_5$, $R_5'$ and L are as described in formula I.

In one embodiment, the noncovalent self-assembled porous membrane of this invention and methods of use thereof comprise a supramolecular structure comprising perylene, a salt thereof or a metal complex thereof as a monomeric unit wherein said perylene is represented by the structure of formula III:

Perylene III

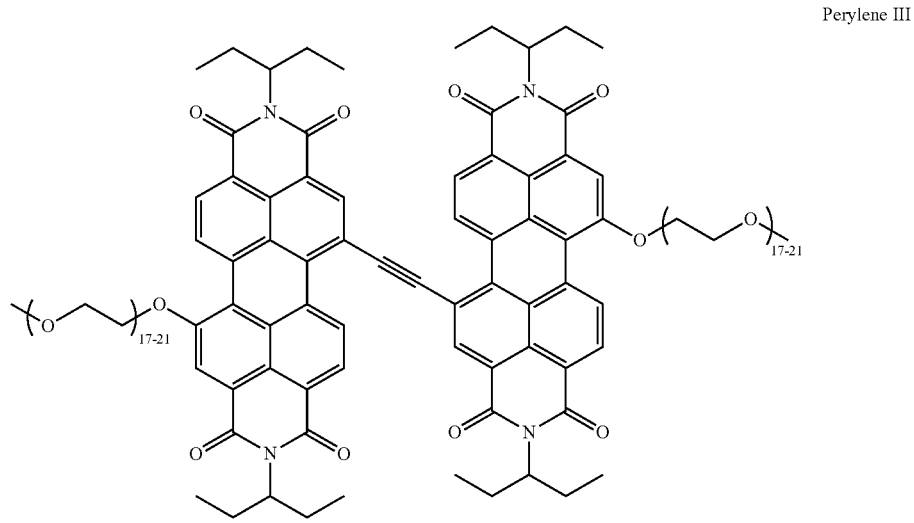

In one embodiment, the noncovalent self-assembled porous membrane of this invention and methods of use thereof comprise a supramolecular structure comprising perylene, a salt thereof or a metal complex thereof as a monomeric unit wherein said perylene is represented by the structure of formula IV:

Perylene IV

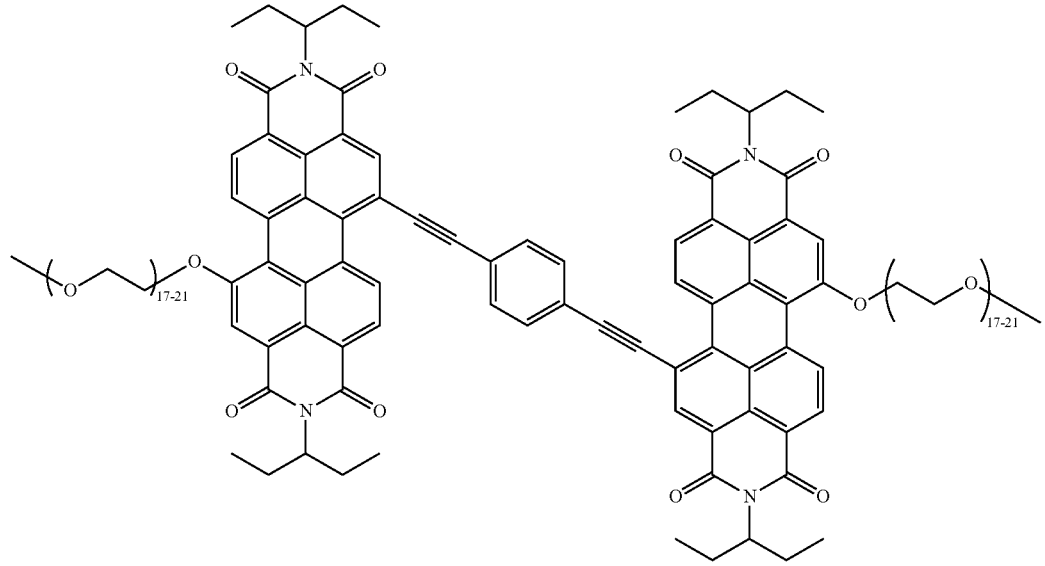

In one embodiment, the noncovalent self-assembled porous membrane of this invention and methods of use thereof comprise a supramolecular structure comprising perylene, a salt thereof or a metal complex thereof as a monomeric unit wherein said perylene is represented by the structure of formula V:

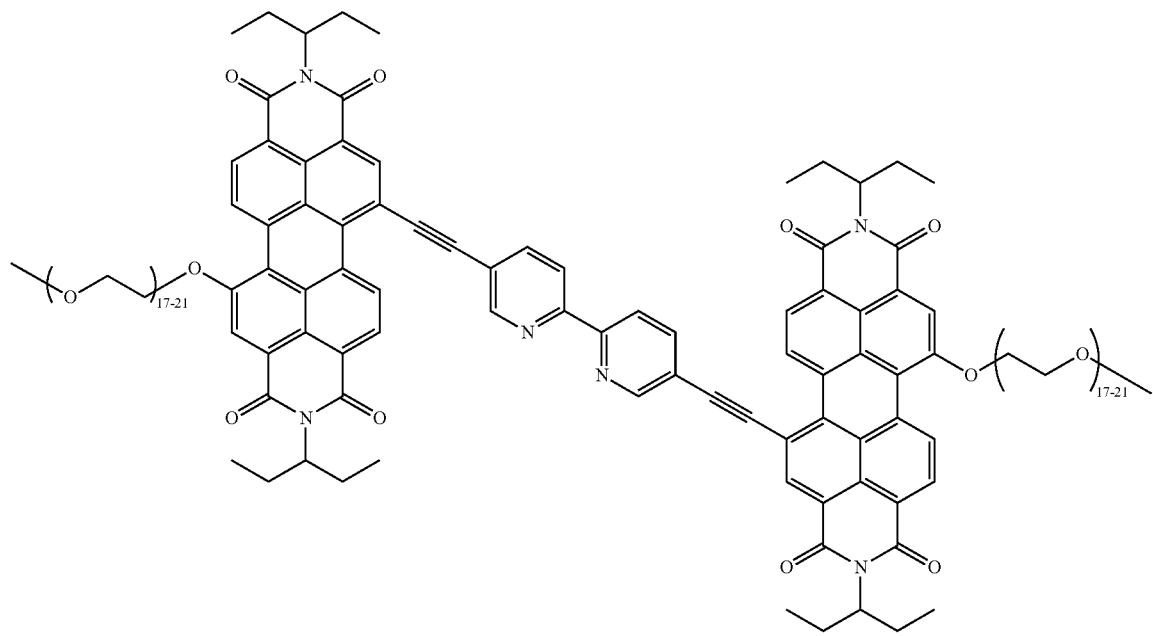

Perylene V

In one embodiment, the noncovalent self-assembled porous membrane of this invention and methods of use thereof comprise a supramolecular structure comprising perylene, a salt thereof as a monomeric unit wherein said perylene is represented by the structure of formula Perylene V-Pt complex:

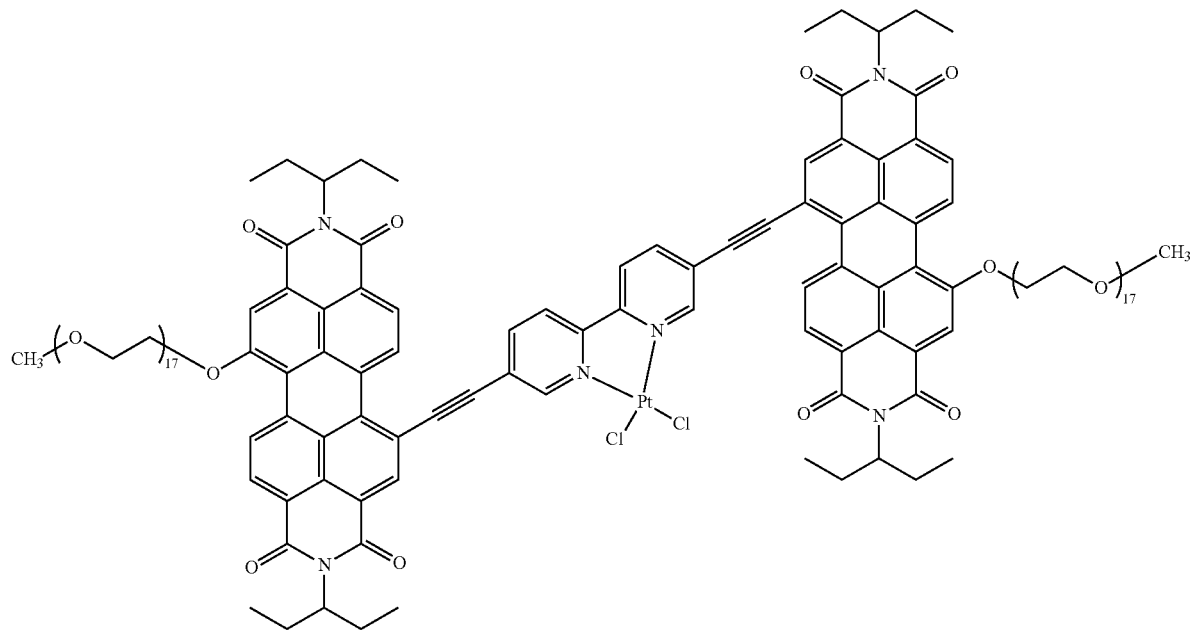

Perylene V-Pt complex

In one embodiment, this invention is directed to noncovalent self-assembled porous membrane and methods of use thereof comprising a supramolecular structure comprising perylene, a salt thereof or a metal complex thereof as a monomeric unit wherein said perylene is represented by the structure of formula VI:

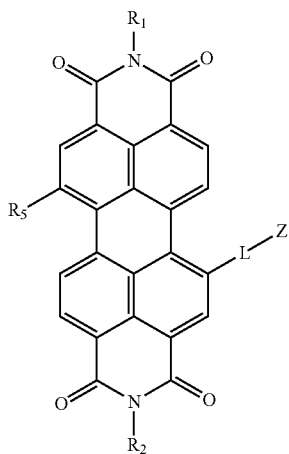

VI wherein $R_1$ is $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$, $(C_1-C_{32})$alkyl, $(C_3-C_8)$cycloalkyl, aryl, heteroaryl, chiral group, $(C_1-C_{32})$alkyl-COOH, $(C_1-C_{32})$alkyl-Si-A, or $[C(O)NHR_3NH]_pH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$alkyl; and wherein $R_3$ in said $[C(O)NHR_3NH]_pH$ is an alkyl, haloalkyl, hydroxyalkyl, hydroxyl, aryl, phenyl, alkylphenyl, alkylamino and independently the same or different when p is larger than 1;

$R_2$ is $[(CH_2)_q O]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, $(C_1-C_{32})$alkyl, $(C_3-C_8)$cycloalkyl, aryl, heteroaryl, chiral group, $(C_1-C_{32})$alkyl-COOH, $(C_1-C_{32})$alkyl-Si-A, or $[C(O)NHR_4NH]_sH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)NHR_4NH]_sH$ is an alkyl, haloalkyl, hydroxyalkyl, hydroxyl, aryl, phenyl, alkylphenyl, alkylamino and independently the same or different when s is larger than 1;

$R_5$ is H, —$OR_x$ where $R_x$ is $C_1-C_6$ alkyl or $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, aryl, heteroaryl, chiral group, $C\equiv C$—$R_7$, $CH=CR_8R_9$, $NR_{10}R_{11}$ or a saturated carbocyclic or heterocyclic ring wherein said saturated heterocyclic ring or heteroaryl contains at least one nitrogen atom and $R_5$ is connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);

Z is —$OR_x$ where $R_x$ is $C_1-C_6$ alkyl or $[(CH_2)_qO]_rCH_3$, peptide, amino-acid, chiral group, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, aryl, heteroaryl, $C\equiv C$—$R_7$, $CH=CR_8R_9$, $NR_{10}R_{11}$ or a saturated carbocyclic or heterocyclic ring wherein said saturated heterocyclic ring or heteroaryl contains at least one nitrogen atom and Z is connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);

$R_7$ is H, halo, $(C_1-C_{32})$alkyl, aryl, $NH_2$, alkyl-amino, COOH, C(O)H, alkyl-COOH heteroaryl, $Si(H)_3$ or $Si[(C_1-C_8)alkyl]_3$ wherein said aryl or heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);

$R_8$, $R_9$, $R_{10}$ and $R_{11}$ are independently H, $(C_1-C_{32})$alkyl, aryl, $NH_2$, alkyl-amino, COOH, C(O)H, alkyl-COOH or heteroaryl wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);

L is a linker or a bond;

n is an integer from 1-5;

o is an integer from 1-100;

p is an integer from 1-100;

q is an integer from 1-5;

r is an integer from 1-100; and s is an integer from 1-100;

wherein if Z is a chiral group, amino acid or peptide; said membrane will form a chiral membrane.

In one embodiment, the noncovalent self-assembled porous membrane of this invention and methods of use thereof comprise a supramolecular structure comprising perylene, a salt thereof or a metal complex thereof as a monomeric unit wherein said perylene is represented by the structure of formula VII:

Perylene VII

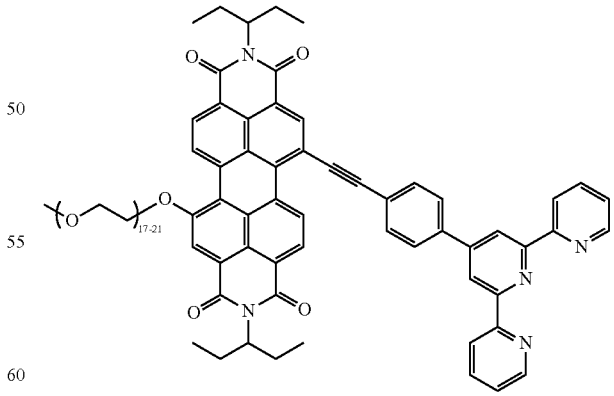

In one embodiment, the noncovalent self-assembled porous membrane of this invention and methods of use thereof comprise a supramolecular structure comprising perylene or a salt thereof as a monomeric unit wherein said perylene is represented by the structure of formula VII-Pd Complex:

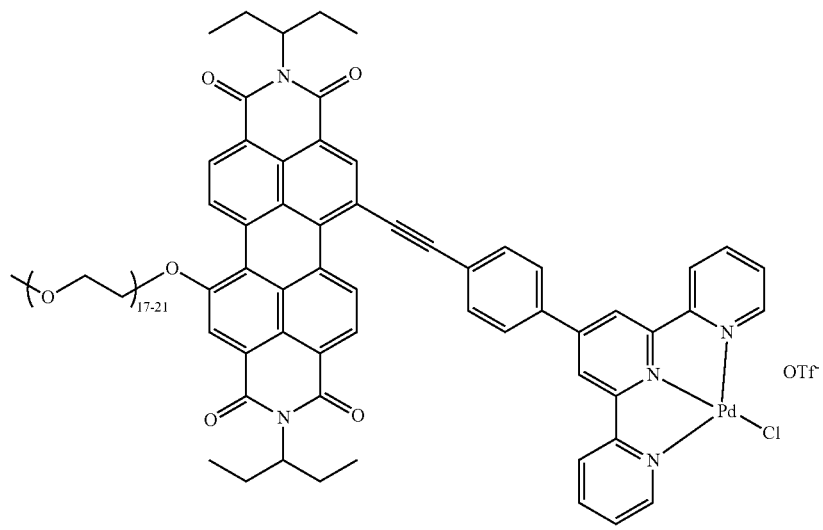

Perylene VII-Pd Complex

In one embodiment, the noncovalent self-assembled porous membrane of this invention and methods of use thereof comprise a supramolecular structure comprising perylene or a salt thereof as a monomeric unit wherein said perylene is represented by the structure of formula VII-Pt Complex:

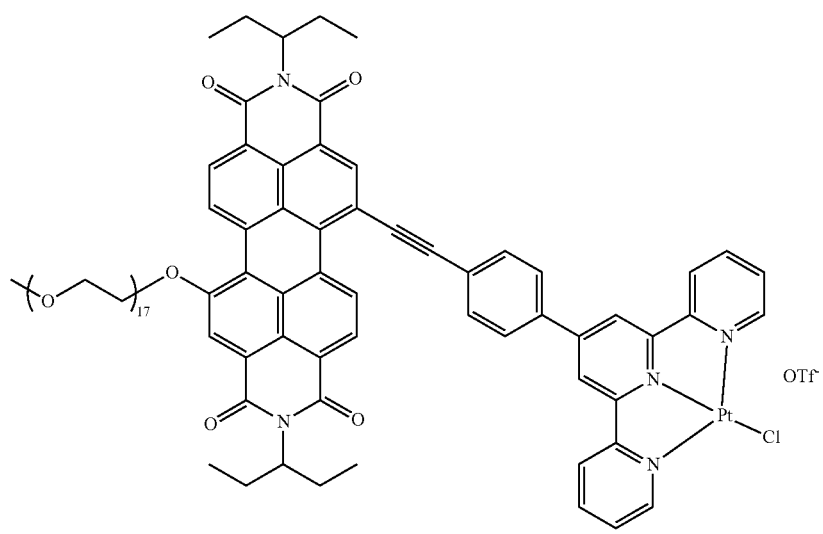

Perylene VII-Pt Complex

In one embodiment, the noncovalent self-assembled porous membrane of this invention and methods of use thereof comprise a supramolecular structure comprising perylene, or a salt thereof as a monomeric unit wherein said perylene is represented by the structure of formula VII-Ag Complex:

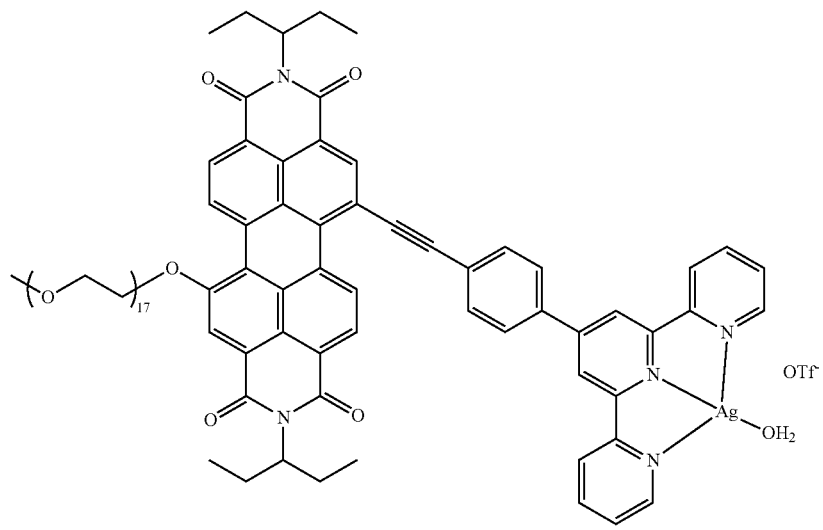

Perylene VII-Ag Complex

In one embodiment, this invention is directed to noncovalent self-assembled porous and chiral membrane and methods of use thereof comprising a supramolecular structure comprising a chiral perylene, a salt thereof or a metal complex thereof as a monomeric unit wherein said perylene is represented by the structure of formula I wherein $R_5$ or $R_5'$ are independently a chiral group, an amino acid or a peptide. In another embodiment, said perylene is represented by the structure of formula VI wherein Z is a chiral group, an amino acid or a peptide. In another embodiment, said perylene is represented by the structure of formula VI wherein Z is a chiral group, an amino acid or a peptide and $R_5$ is a PEG substituted by a chiral group.

In one embodiment, the noncovalent self-assembled porous and chiral membrane of this invention comprising a supramolecular structure comprising a chiral perylene, a salt thereof or a metal complex thereof as a monomeric unit wherein said perylene is represented by the following structures:

Perylene VIII

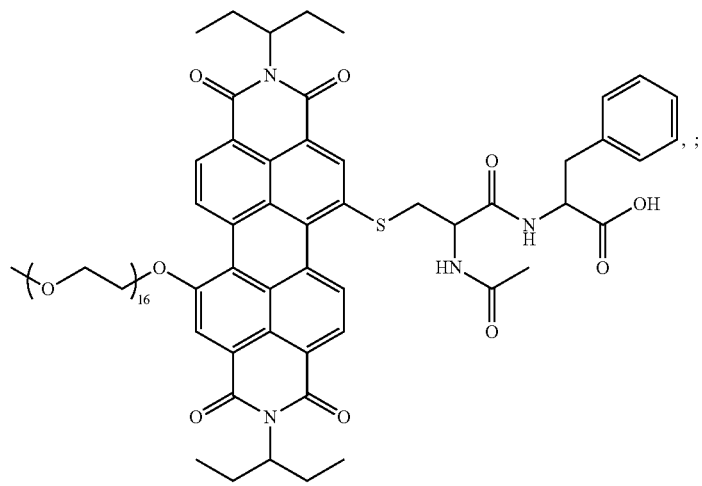

-continued
Perylene IX
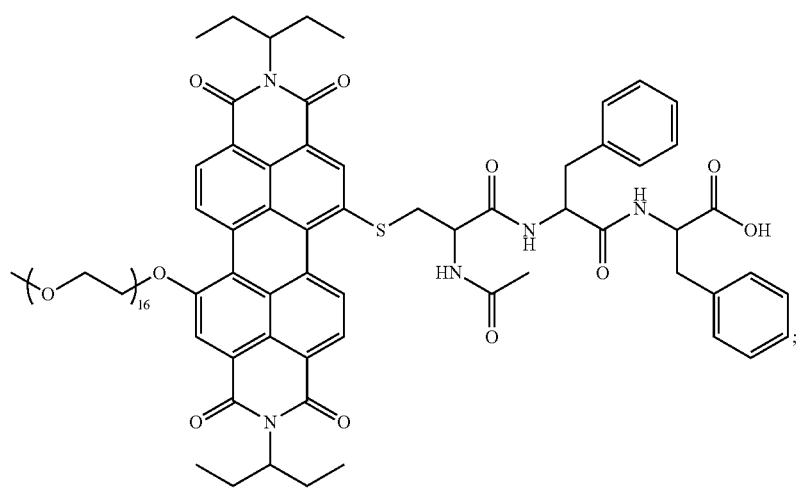
Perylene X
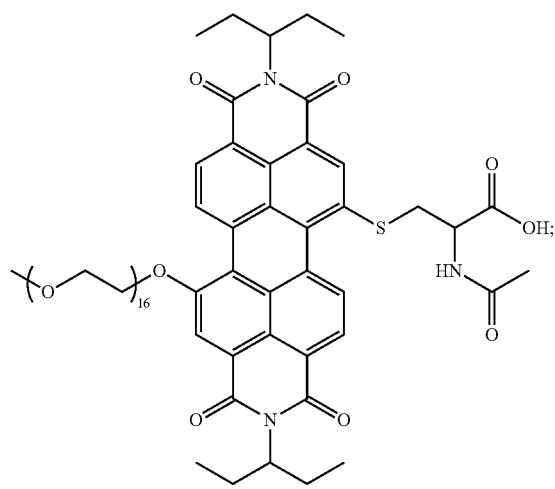
Perylene XI
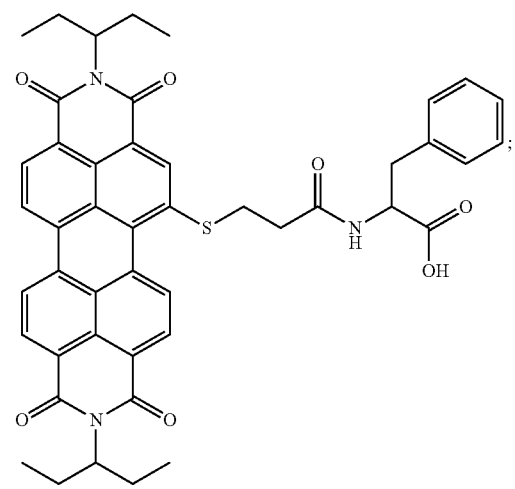
Perylene XII
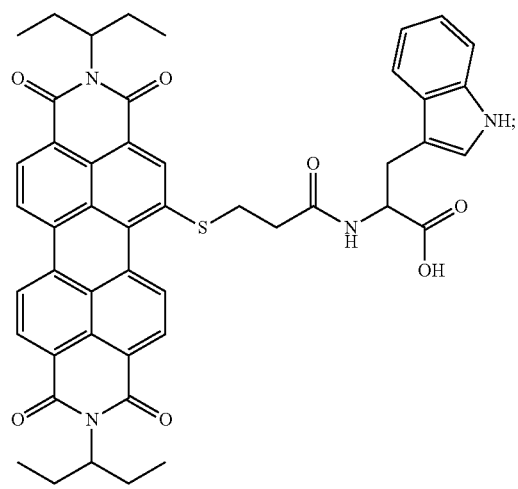
Perylene XIII
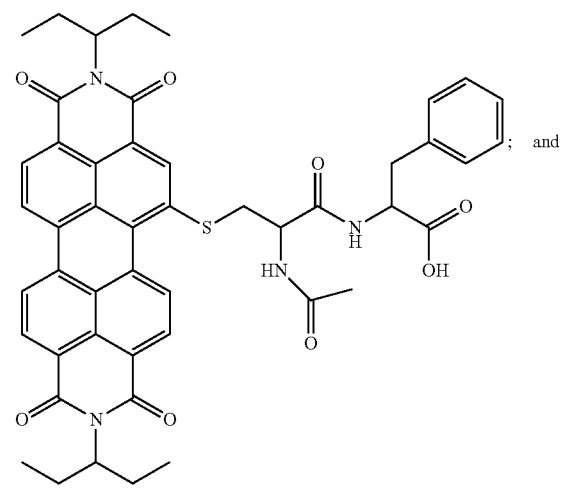
; and Perylene XIV

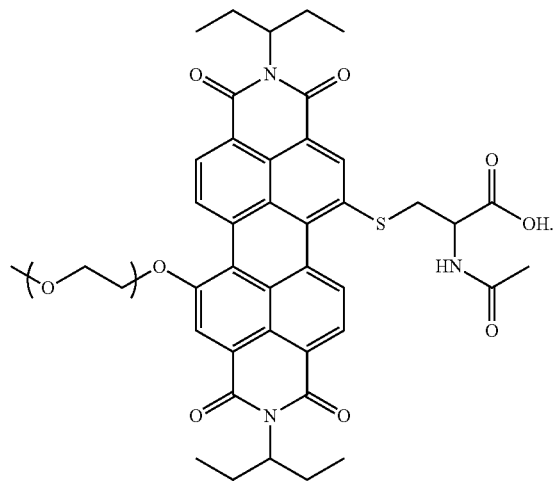

In one embodiment L of formula I, II or VI is an unsaturated bridge. In another embodiment, L of formula VI is saturated or unsaturated bridge. In one embodiment an unsaturated bridge of this invention is acetylene. In one embodiment an unsaturated bridge of this invention is phenylacetylene. In another embodiment an unsaturated bridge of this invention comprises an acetylene. In another embodiment an unsaturated bridge of this invention comprises a pyridyl. In another embodiment an unsaturated bridge of this invention comprises a bipyridyl. In another embodiment an unsaturated bridge of this comprises a terpyridyl. In another embodiment an unsaturated bridge of this invention comprises a phenyl. In another embodiment an unsaturated bridge of this comprises a dibenzene. In another embodiment an unsaturated bridge of this invention comprises diethynylbenzene. In another embodiment an unsaturated bridge of this invention comprises aryl. In another embodiment an unsaturated bridge of this invention comprises diethynyl-bipyridyl. In one embodiment an unsaturated bridge of this invention comprises bis-acetylene. In another embodiment an unsaturated bridge of this invention is a pyridyl group. In another embodiment an unsaturated bridge of this invention is a bipyridyl group. In another embodiment an unsaturated bridge of this invention is a terpyridyl group. In one embodiment L of formula I and II is a saturated bridge. In another embodiment a saturated bridge of this invention comprises an alkyl, cycloalkyl, heterocycle, ether, polyether, or haloalkyl. In one embodiment L of formula I and II is a combination of a saturated and unsaturated groups as defined hereinabove. In another embodiment, L of formula VI is an unsaturated bridge. In another embodiment, L of formula VI is an unsaturated bridge including —S—(CH$_2$)$_t$—C(O)—; —S—(CH$_2$)$_t$—O—; —O—(CH$_2$)$_t$—O—, —NH—(CH$_2$)$_t$—C(O)—; —C(O)—(CH$_2$)$_t$—CO—; —C(O)—(CH$_2$)$_t$—NH— wherein t is between 1 to 6.

In another embodiment L of formula I, II or VI is:

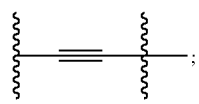

a

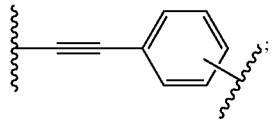

b

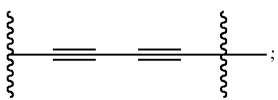

c

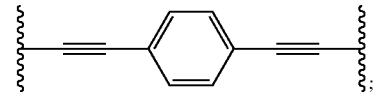

d

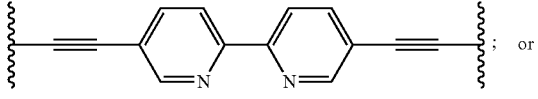

e; or

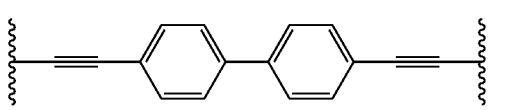

f

In one embodiment R$_5$ and R$_5$' of formula I, II and VI is a hydrophilic side chain. In another embodiment R$_5$ and R$_5$' of formula I and II and VI are independently a PEG (polyethylene glycol). In another embodiment the PEG of this invention comprises between 15-20 units. In another embodiment the PEG comprises between 17-21 repeating units. In another embodiment the PEG comprises between 18-22 repeating units. In another embodiment the PEG comprises about 19 repeating units. In another embodiment the PEG comprises between 15 to 25 repeating units. In another embodiment the PEG comprises between 18 to 24 repeating units. In another embodiment the PEG comprises between 10 to 30 repeating units. In one embodiment, R$_5$ and R$_5$' of formula I, II and VI (or the side chains of the perylene monomers) is —OR$^x$ where R$^x$ is C$_1$-C$_6$ alkyl or [(CH$_2$)$_n$O]$_o$CH$_3$. In another embodiment, R$_5$ and R$_5$' of formula I, II and VI are independently —OR$^x$ where R$^x$ is [(CH$_2$)$_n$O]$_o$CH$_3$, and n is 2 or 3. In another embodiment, R$_5$ and R$_5$' are —OR$^x$ where R$^x$ is [(CH$_2$)$_n$O]$_o$CH$_3$, n is 2 and o is 19. In another embodiment, the perylenes comprise different lengths of PEG size chains, wherein the average lengths is of the side chains is between 17-22 or 18-22 repeating units.

In one embodiment $R_1$, $R_1'$, $R_2$ and $R_2$ are the same. In another embodiment, $R_1$, $R_1'$, $R_2$ and $R_2$ are different. In another embodiment, $R_1$, $R_1'$, $R_2$ and $R_2$ are independently an alkyl. In another embodiment, $R_1$, $R_1'$, $R_2$ and $R_2$ are independently $-CH(CH_2CH_3)_2$. In another embodiment, $R_1$, $R_1'$, $R_2$ and $R_2$ are independently a phenyl. In another embodiment, $R_1$, $R_1'$, $R_2$ and $R_2$ are independently a $CH_2$-phenyl. In another embodiment, $R_1$, $R_1'$, $R_2$ and $R_2$ are independently a PEG. In another embodiment, $R_1$, $R_1'$, $R_2$ and $R_2$ are independently a chiral group.

In one embodiment, "o" of $R_1$ and $R_1'$ of formula I, II and VI in the following substituents $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$, is between 1-100. In another embodiment "o" is between 15-20. In another embodiment "o" is between 10-20. In another embodiment "o" is between 17-22. In another embodiment "o" is about 19. In another embodiment "o" is between 10-30. In another embodiment "o" is between 20-40. In another embodiment "o" is between 20-50.

In one embodiment, "r" of $R_2$, $R_2'$, $R_5$ and $R_5'$ formula I, II and VI in the following substituents $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$ is between 1-100. In another embodiment r is between 15-20. In another embodiment "r" is between 10-20. In another embodiment "r" is between 17-22. In another embodiment "r" is about 19. In another embodiment "r" is between 10-30. In another embodiment "r" is between 20-40. In another embodiment "r" is between 20-50.

In one embodiment "p" of $R_1$ and $R_1'$ formula I, II and VI in the following substituent $[C(O)NHR_3NH]_pH$ is between 1-100. In another embodiment "p" is between 15-20. In another embodiment "p" is between 10-20. In another embodiment "p" is between 17-22. In another embodiment "p" is about 19. In another embodiment "p" is between 10-30. In another embodiment "p" is between 20-40. In another embodiment "p" is between 20-50.

In one embodiment "n" of $R_1$ and $R_1'$ formula I, II and VI in the following substituent $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$ is between 1-5. In another embodiment "n" is 1. In another embodiment "n" is 2. In another embodiment "n" is 3. In another embodiment "n" is 4. In another embodiment "n" is 5.

In one embodiment "q" of $R_2$ and $R_2'$ formula I, II and VI in the following substituent independently $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, is between 1-5. In another embodiment "q" is 1. In another embodiment "q" is 2. In another embodiment "q" is 3. In another embodiment "q" is 4. In another embodiment "q" is 5.

In one embodiment "s" of $R_2$ and $R_2'$ formula I, II and VI in the following substituent $[C(O)NHR_4NH]_sH$ is between 1-100. In another embodiment "s" is between 15-20. In another embodiment "s" is between 10-20. In another embodiment "s" is between 17-22. In another embodiment "s" is about 19. In another embodiment "s" is between 10-30. In another embodiment "s" is between 20-40. In another embodiment "s" is between 20-50.

In one embodiment, Z of formula VI is $-OR_x$ where $R_x$ is $C_1$-$C_6$ alkyl or $[(CH_2)_qO]_rCH_3$.

In one embodiment, Z of formula VI is a peptide. In another embodiment, Z is a peptide including between 2-4 amino acids. In another embodiment, Z is a peptide including between 2-6 amino acids. In another embodiment, Z is a peptide including between 2-10 amino acids. In another embodiment, the amino acids are protected amino acids. In another embodiment, Z of formula VI is a peptide wherein the peptide is attached to the linker (L) via one of the side chains of the amino acid. In another embodiment, Z of formula VI is a peptide wherein the peptide is attached to the linker (L) via the amino end. In another embodiment, Z of formula VI is a peptide wherein the peptide is attached to the linker (L) via the carboxylic end. In another embodiment, Z of formula VI is a peptide, L is a bond and the peptide is attached the perylene directly via one of the side chains of the amino acid. In another embodiment, Z of formula VI is a peptide, L is a bond and the peptide is attached the perylene directly via the amino end. In another embodiment, Z of formula VI is a peptide, L is a bond and the peptide is attached the perylene directly via the carboxylic acid end. In another embodiment, the peptide is -Cys-Phe, In another embodiment, the peptide is -Cys-Phe-Phe. In another embodiment, the peptide is chiral.

In one embodiment, Z of formula VI is an amino acid. In another embodiment, the amino acid is Phe. In another embodiment, the amino acid is Trp. In another embodiment, the amino acid is Cys. In another embodiment, the amino acid is Tyr. In another embodiment the amino acid is not an enantiomeric mixture. In another embodiment, the amino acid is a pure enantiomer.

In one embodiment, Z of formula VI is a chiral group. In another embodiment, $R_1$, $R_1'$, $R_2$, $R_2'$, $R_5$ and $R_5'$ of formula I, II, and VI are a chiral group. In another embodiment, "chiral group" refers to any group that lack symmetry. Non limiting examples of chiral group include an amino acid, an artificial amino acid, a peptide, a protein, a sugar, DNA, RNA, a nucleic acid, chiral drug, chiral molecule or combination thereof.

In one embodiment, Z of formula VI is $[(CH_2)_qC(O)O]_rCH_3$. In another embodiment, Z of formula VI is $[(CH_2)_qC(O)NH]_rCH_3$. In another embodiment, Z of formula VI is $[(CH_2)_qCH_2=CH_2]_rCH_3$. In another embodiment, Z of formula VI is $[(CH_2)_qCH=CH]_rCH_3$. In another embodiment, Z of formula VI is $[(CH_2)_qNH]_rCH_3$. In another embodiment, Z of formula VI is $[(alkylene)_qO]_rCH_3$. In another embodiment, Z of formula VI is $[(alkylene)_qC(O)O]_rCH_3$. In another embodiment, Z of formula VI is $[(alkylene)_qC(O)NH]_rCH_3$. In another embodiment, Z of formula VI is $[(alkylene)_qCH_2=CH_2]_rCH_3$. In another embodiment, Z of formula VI is $[(alkylene)_qCH=CH]_rCH_3$. In another embodiment, Z of formula VI is $[(alkylene)_qNH]_rCH_3$. In another embodiment, Z of formula VI is aryl. In another embodiment, Z of formula VI is heteroaryl. In another embodiment, Z of formula VI is $C\equiv C-R_7$. In another embodiment, Z of formula VI is $CH=CR_8R_9$. In another embodiment, Z of formula VI is $NR_{10}R_{11}$. In another embodiment, Z of formula VI is saturated carbocyclic or heterocyclic ring. In another embodiment, Z of formula VI is bipyridyl, terpyridyl or metal complex thereof.

In one embodiment, the self-assembled membrane, and methods of filtration/separation or purification comprise the use of perylene diimide of this invention or a salt thereof which may be produced, by reaction of a compound of this invention with an acid or base. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

In one embodiment, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the self-assembled membrane, and methods of filtration/separation or purification comprise perylene diimide of this invention or its metal complex. In another embodiment the metal complex is a Pd (IV), Pt(II), Ag(I) or any other transitioncomplex of pyridyls, bipyridyls, terpyridyl or any other chelating linkers known in the art.

An "alkyl" or "alkylene" group refers, in one embodiment, to a saturated aliphatic hydrocarbon, including straight-chain and branched-chain groups. In one embodiment, the alkyl group has 1-12 carbons. In another embodiment, the alkyl group has 1-8 carbons. In another embodiment, the alkyl group has 1-6 carbons. In another embodiment, the alkyl group has 1-4 carbons. The alkyl group may be unsubstituted or substituted by one or more groups selected from halogen, cyano, hydroxy, alkoxy carbonyl, amido, alkylamido, dialkylamido, nitro, amino, alkylamino, dialkylamino, carboxyl, thio and thioalkyl. In one embodiment, the alkyl group is —$CH_3$, —$CH(CH_3)_2$, —$CH_2CH(CH_3)_2$, —$CH(CH_3)CH_2CH_3$, and the like A "cycloalkyl" group refers, in one embodiment, to a saturated aliphatic cyclic hydrocarbon group. In one embodiment, the cycloalkyl group has 3-12 carbons. In another embodiment, the cycloalkyl group has 3-8 carbons. In another embodiment, the cycloalkyl group has 3-6 carbons. In another embodiment, the cycloalkyl group has 3 carbons. The cycloalkyl group may be unsubstituted or substituted by one or more groups selected from halogen, cyano, hydroxy, alkoxy carbonyl, amido, alkylamido, dialkylamido, nitro, amino, alkylamino, dialkylamino, carboxyl, thio and thioalkyl. In one embodiment, the cycloalkyl group is cyclopropyl, cyclobutyl, cyclopentyl, cyclohexyl, and the like. In another embodiment, the cycloalkyl comprises of between 1-4 rings.

The term "carbocyclic ring" refers to a saturated or unsaturated ring composed exclusively of carbon atoms. In one embodiment, the carbocyclic ring is a 3-12 membered ring. In another embodiment, the carbocyclic ring is a 3-8 membered ring. In one embodiment, the carbocyclic ring is a five membered ring. In one embodiment, the carbocyclic ring is a six membered ring. In one embodiment the carbocyclic ring may be unsubstituted or substituted by one or more groups selected from halogen, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of carbocyclic ring are benzene, cyclohexane, and the like. In another embodiment, the carbocyclic ring comprises of between 1-4 rings.

The term "aryl" refers to an aromatic group having at least one carbocyclic aromatic ring, which may be unsubstituted or substituted by one or more groups selected from halogen, cyano, aryl, heteroaryl, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, and the like. In one embodiment, the aryl group is a 5-12 membered ring. In another embodiment, the aryl group is a 5-8 membered ring. In one embodiment, the aryl group is a five membered ring. In one embodiment, the aryl group is a six membered ring. In another embodiment, the aryl group comprises of 1-4 fused rings.

The term "arylalkyl" refers to an alkyl group as defined above substituted by an aryl group as defined above. Examples of arylalkyl, but not limited to are —$CH_2Ph$ or —$CH_2CH_2Ph$.

The term "heteroaryl" refers to an aromatic group having at least one heterocyclic aromatic ring. In one embodiment, the heteroaryl comprises at least one heteroatom such as sulfur, oxygen, nitrogen, silicon, phosphorous or any combination thereof, as part of the ring. In another embodiment, the heteroaryl may be unsubstituted or substituted by one or more groups selected from halogen, aryl, heteroaryl, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of heteroaryl rings are pyranyl, pyrrolyl, pyrazinyl, pyrimidinyl, pyrazolyl, pyridinyl, furanyl, thiophenyl, thiazolyl, indolyl, imidazolyl, isoxazolyl, and the like. In one embodiment, the heteroaryl group is a 5-12 membered ring. In one embodiment, the heteroaryl group is a five membered ring. In one embodiment, the heteroaryl group is a six membered ring. In another embodiment, the heteroaryl group is a 5-8 membered ring. In another embodiment, the heteroaryl group comprises of 1-4 fused rings. In one embodiment, the heteroaryl group is 1,2,3-triazole. In one embodiment the heteroaryl is a pyridyl. In one embodiment the heteroaryl is a bipyridyl. In one embodiment the heteroaryl is a terpyridyl.

The terms "halide" and "halogen" refer to in one embodiment to F, in another embodiment to Cl, in another embodiment to Br, in another embodiment to I.

A "heterocyclic" group refers to a heterocycle. In one embodiment, said heterocycle refers to a ring structure comprising in addition to carbon atoms, sulfur, oxygen, nitrogen, silicon or phosphorous or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the heterocycle group may be unsubstituted or substituted by a halide, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring.

The term "hydroxylalkyl" refers to an alkyl as described above substituted by hydroxyl group. Nonlimiting examples of hydroxyalkyl are $—CH_2OH$, $—CH_2CH_2OH$ and the like.

The term "alkylamino" refers to an alkyl as described above substituted by an amine group. Nonlimiting examples of alkylamono are $—CH_2NH_2$, $—CH_2CH_2N(CH_3)_2$, $—(CH_2)_5NH_2$ and the like.

In one embodiment, this invention is directed to noncovalent self-assembled porous membrane comprising a perylene diimide supramolecular structure, having a cutoff size of ultrafiltration of between 2-100 nm and provides a chromatography medium for size-selective separation of nano-materials of between 1-5 nm particle sizes. In another embodiment, the perylene diimide supramolecular structure (membrane) provides a chromatography medium for size-selective separation of nano-materials of between 7-10 nm particle sizes. In another embodiment, the perylene diimide supramolecular structure (membrane) provides a chromatography medium for size-selective separation of nano-materials of between 5-10 nm particle sizes. In another embodiment, the perylene diimide supramolecular structure (membrane) provides a chromatography medium for size-selective separation of nano-materials of between 5-20 nm particle sizes. In another embodiment, the perylene diimide supramolecular structure (membrane) provides a chromatography medium for size-selective separation of nano-materials of between 2-10 nm particle sizes. In another embodiment, the nano-materials are nanoparticles or biomolecules. In another embodiment, size-selective separation of nanoparticles is performed through a membrane having pores size with a cutoff size of between 1-5 nm. In another embodiment, size-selective separation of biomolecules is performed through a membrane having pores size with a cutoff size of between 7-10 nm.

In another embodiment, membrane cutoff values are known to depend on shape and deformability of the filtered particles. In another embodiment, the membrane pores depend on the thickness of the membrane. In another embodiment, enlargement of the pores can be obtained by heating the membrane. In another embodiment, enlargement of the pores can be obtained by increasing the temperature of the membrane to a temperature between 30-60° C. In another embodiment, enlargement of the pores can be obtained by increasing the temperature of the membrane to a temperature between 30-100° C.

In one embodiment, this invention is directed to noncovalent self-assembled porous chiral membrane comprising a chiral perylene diimide supramolecular structure, having a cutoff size of ultrafiltration of between 2-100 nm; providing a chromatography medium for size-selective separation of nano-materials and providing chiral separation for chiral nano-materials. In another embodiment, the chiral membrane of this invention provides chiral separation between chiral biomolecules. In another embodiment, the chiral membrane of this invention provides chiral separation between chiral nanoparticles, biomolecules or chiral nano-materials. In another embodiment, chiral nano-materials include any chiral material/molecule having a chiral center, an amino acid, an artificial amino acid, a peptide, a protein, a sugar, DNA, RNA, a nucleic acid, chiral drug, chiral molecule or any combination thereof.

In one embodiment, this invention is directed to noncovalent self-assembled porous membrane comprising a perylene diimide supramolecular structure, having a cutoff size of ultrafiltration of between 2-100 nm and provides a chromatography medium for size-selective separation of nanoparticles of between 1-5 nm particle sizes.

In one embodiment, this invention is directed to noncovalent self-assembled porous membrane comprising a perylene diimide supramolecular structure, having a cutoff size of ultrafiltration of between 2-100 nm and provides a chromatography medium for size-selective separation of biomolecules of between 7-10 nm particle sizes or a biomolecule of about 150 kDa.

In one embodiment, the membrane of this invention has a cutoff size of between 2 nm to 4 nm. In another embodiment, the membrane of this invention has a cutoff size of between 2 nm to 5 nm. In another embodiment, the membrane of this invention has a cutoff size of between 3 nm to 10 nm. In another embodiment, the membrane of this invention has a cutoff size of between 2 nm to 15 nm. In another embodiment, the membrane of this invention has a cutoff size of between 5 nm to 10 nm. In another embodiment, the membrane of this invention has a cutoff size of between 5 nm to 20 nm. In another embodiment, the membrane of this invention has a cutoff size of between 5 nm to 50 nm. In another embodiment, the membrane of this invention has a cutoff size of between 5 nm to 15 nm. In another embodiment, the membrane of this invention has a cutoff size of between 20 nm to 50 nm.

In one embodiment, this invention is directed to porous membrane wherein the cutoff size of the pores is between 2-100 nm. In another embodiment, the cutoff size depends on the thickness of the membrane. In another embodiment, the thickness of the membrane is between 5-100 µm. In another embodiment, the thickness of the membrane is between 10-50 µm. In another embodiment, the thickness of the membrane is between 10-20 µm. In another embodiment, the thickness of the membrane is between 15-30 µm. In another embodiment, the thickness of the membrane is between 10-40 µm. In another embodiment, the thickness of the membrane is between 30-40 µm. In another embodiment, the thickness of the membrane is between 10-20 µm.

In one embodiment, a membrane thickness of between 10-15 µm provides a cutoff size of 5 nm. In another embodiment, a membrane thickness of between 40-50 µm provides a cutoff size of between 2-4 nm. In another embodiment, this invention is directed to a membrane providing a chromatography medium for size-selective separation of nano-materials of between 1-5 nm particle size comprising self assembled perylene of this invention. In another embodiment, a thicker layer of self assembled perylene diimide of this invention provide better separation between the nano-materials. (i.e smaller nano-materials will pass faster through the membrane than larger nano-materials, and thereby provide size separation between the nano-materials.)

In one embodiment, the term "nano-materials" refer to mixture of materials (same or different) having different particle sizes wherein one of the materials has particle size of between 1-200 nm. The term "nano-materials" refer to same materials having different particle size or to different materials having different particle size. In another embodiment, the term "nano-materials" refer to nanoparticles. In another embodiment, the term "nano-material" refer to sub nanometer size materials including small molecules. In another embodiment, the nano-materials refer to biomolecules. In another embodiment, the term "chiral nano-materials" refer to chiral compounds in the nanometer and sub nanometer size material.

In one embodiment, this invention provides a method for separation/filtration, purification and optimization of nanoparticles. In another embodiment, this invention provides a method for separation/filtration, purification and optimization of nanoparticles in a size domain of sub 5 nm. In another embodiment, applications in separation/filtration, purification and optimization of nanoparticles in a size domain is highly relevant to optical, catalytic, and biological applications. In another embodiment, the nanoparticles refer to gold nanoparticles, metal nanoparticles, metal oxide nanoparticles, nanoparticles which are soluble in water, quantum dots (CdS nanoparticles, CdSe nanoparticles, CdTe nanoparticles), polymers, biomacromolecules, such as peptides, DNA, RNA, viruses, and proteins.

In one embodiment, this invention provides a method for separation/filtration, purification and optimization of biomolecules. In another embodiment, this invention provides a method for separation/filtration, purification and optimization of nanoparticles. In another embodiment, applications in separation/filtration, purification and optimization of biomolecules in a size domain is highly relevant for medical and biological systems. In another embodiment, the biomolecules refer to peptides, DNA, RNA, proteins and separation of viruses. In another embodiment separation of proteins is disclosed in Examples 13 and 16.

The cutoff value of the supramolecular membrane is in the upper range of commonly used ultrafiltration membranes in biotechnology, allowing the retention of large proteins, nucleic acids, lipids and other large lysate components.

In one embodiment, this invention provides a method of rapid separation of protein monomers from protein aggregates using the perylene diimide membrane of this invention. In another embodiment, this invention provides a method of separation of protein monomers from protein aggregates as described in Example 18.

In one embodiment, this invention provides a biocatalytic membrane comprising a noncovalent self-assembled porous membrane comprising a perylene diimide supramolecular structure of this invention and an enzyme; wherein said enzyme is immobilized within said membrane; wherein said noncovalent self-assembled perylene diimide supramolecular structure comprises a perylene, a salt thereof or a metal thereof of formula I-XIV as a monomeric unit. In another embodiment, noncovalent self-assembled perylene diimide supramolecular structure comprises a perylene, a salt thereof or a metal thereof of formula I as a monomeric unit. In another embodiment, noncovalent self-assembled perylene diimide supramolecular structure comprises a perylene, a salt thereof or a metal thereof of formula II as a monomeric unit. In another embodiment, noncovalent self-assembled perylene diimide supramolecular structure comprises a perylene, a salt thereof or a metal thereof of formula III as a monomeric unit. In another embodiment, noncovalent self-assembled perylene diimide supramolecular structure comprises a perylene, a salt thereof or a metal thereof of formula IV as a monomeric unit. In another embodiment, noncovalent self-assembled perylene diimide supramolecular structure comprises a perylene, a salt thereof or a metal thereof of formula V as a monomeric unit. In another embodiment, noncovalent self-assembled perylene diimide supramolecular structure comprises a perylene, a salt thereof or a metal thereof of formula VI-XIV as a monomeric unit.

In one embodiment, this invention provides a method of heterogenous catalysis comprising (a) transferring an aqueous solution or emulsion comprising a perylene diimide supramolecular structure of this invention through porous solid support, thereby forming a noncovalent self-assembly perylene based membrane layer on said porous solid support; (b) transferring a biocatalyst through said membrane layer; wherein said biocatalyst is immobilized within said membrane; and (c) passing through said immobilized biocatalyst a substrate wherein a catalytic reaction occurs between said biocatalyst and said substrate. In another embodiment, the biocatalyst is an enzyme.

Immobilization on the supramolecular membranes is versatile and applicable to various enzymes provided that they are large enough to be retained. In order to extend the method to smaller enzymes, one can use standard procedures to enlarge the enzyme without affecting its activity, either by fusing the enzyme to a large inactive protein, or by formation of cross-linked enzyme aggregates (CLEAs) prior to filtration. Effective immobilization techniques has been described as one of the main obstacles for industrial-scale biocatalysis. This invention provides enzyme entrapment in a supramolecular membrane is accomplished in a simple filtration step within 20 minutes. The reactant conversion can be controlled by adjusting the amount of enzyme deposited on the supramolecular membrane. Having a substantial thickness of ~6 μm the noncovalent matrix functions as a depth filter, allowing very high enzyme loading (e.g. 0.4 g enzyme/1 g perylene diimide membrane) without membrane clogging.

Biocatalysis in membrane reactors takes place within the short time of the substrate's passing through the membrane layer. Thus, high enzyme loading is important in order to achieve satisfying reaction yields.

In another embodiment, heterogeneous biocatalysis facilitates more complex cascade reactions, wherein two or more enzymes are immobilized in a sequential manner. As membrane fabrication and enzyme immobilization are carried out by simple deposition steps, preparation of complex layered structures with alternating membrane/enzyme arrays.

In another embodiment, the advantages of the biocatalytic membrane and methods of heterogeneous catalysis include: (i) no synthetic modification or covalent attachment of the enzyme to a stationary phase is necessary. (ii) Enzymes/biocatalysts can be easily retrieved from the membrane by disassembly of the noncovalent membrane material, which is important considering the high cost of enzyme synthesis.

In one embodiment, this invention provides a method for separation/filtration, purification and optimization of chiral nano-materials. In another embodiment, the chiral nano-materials refer nano-sized materials and subnanometer size possessing a chiral center. Non limiting examples include an amino acid, an artificial amino acid, a peptide, a protein, a sugar, DNA, RNA, a nucleic acid, chiral drug, chiral molecule or combination thereof.

In one embodiment, this invention is directed to a method of separation/filtration or purification of nanoparticles comprising (a) transferring an aqueous solution or emulsion comprising a perylene diimide supramolecular structure of this invention through porous solid support, thereby forming a noncovalent self-assembly perylene based membrane on said porous solid support; (b) transferring nanoparticles through said noncovalent self-assembly perylene based membrane of step (a); wherein the particles which are larger than the pores of said membrane remain on said membrane. In another embodiment, the method includes further chiral separation/filtration or purification of chiral nanoparticles.

In one embodiment, this invention is directed to a method of separation/filtration or purification of biomolecules comprising (a) transferring an aqueous solution or emulsion comprising a perylene diimide supramolecular structure of this invention through porous solid support, thereby forming a noncovalent self-assembly perylene based membrane on said porous solid support; (b) transferring a solution of biomolecules through said noncovalent self-assembly perylene based membrane of step (a); wherein the particles which are larger than the pores of said membrane remain on said membrane. In another embodiment, the method includes further chiral separation/filtration or purification of chiral biomolecules.

In one embodiment, this invention is directed to a method of separation/filtration or purification of chiral nano-materials comprising (a) transferring an aqueous solution or emulsion comprising a chiral perylene diimide supramolecular structure of this invention through porous solid support, thereby forming a noncovalent self-assembly chiral perylene based membrane on said porous solid support; (b) transferring chiral nano-materials through said noncovalent self-assembly perylene based membrane of step (a); wherein the chiral-nano-materials are separated/filtered or purified.

In one embodiment, the methods of this invention provide separation between nanoparticles or separation between biomolecules at a size range of between 3-40 nm. In one embodiment, the methods of this invention provide separation between nanoparticles or separation between biomolecules at a size range of between 1-5 nm. In one embodiment, the methods of this invention provide separation between nanoparticles or separation between biomolecules at a size range of between 5-10 nm. In one embodiment, the methods of this invention provide separation between nanoparticles or separation between biomolecules at a size range of between 7-10 nm.

In one embodiment, the methods of this invention fractionate nanoparticles or fractionate biomolecules between 5 and 40 nm. In another embodiment this invention is directed to fractionates nanoparticles or fractionate biomolecules between 3 and 10 nm. In another embodiment this invention is directed to fractionates nanoparticles or fractionate biomolecules between 1 and 5 nm. In another embodiment this invention is directed to fractionates nanoparticles or fractionate biomolecules between 5 and 10 nm. In another embodiment this invention is directed to fractionates nanoparticles or fractionate biomolecules between 7 and 10 nm.

In one embodiment, this invention provides a method for separation/filtration, purification and optimization of nanoparticles or biomolecules in a size domain. In another embodiment, the separation/filtration or purification is based on the thickness of the membrane. In another embodiment particles with a cap off of 5 nm are separated on a membrane of between 10-15 μm thickness. In another embodiment quantum dots of a size between 1-5 nm, are separated on a membrane of between 40-50 μm thickness. In another embodiment, this invention provides a chromatography medium for size-selective separation of nanoparticles or biomolecules.

In one embodiment the separated and/or fractionate nanoparticles do not aggregate or fuse using the methods of this invention.

In one embodiment the separated and/or fractionate biomolecules do not aggregate or fuse using the methods of this invention.

In one embodiment, the membrane of this invention is deposited on a solid support. In another embodiment, the solid support is a microfiltration filter. In another embodiment, the microfiltration filter comprises cellulose acetate (CA). In another embodiment, the microfiltration filter comprises Teflon (PTFE). In another embodiment, the microfiltration filter comprises polycarbonate. In another embodiment, the microfiltration filter is commercially available having a pore size smaller or equal to 0.45 microns and larger than 5 nm. In another embodiment, the microfiltration filter has a pore size which is larger than 5 nm. In another embodiment, the microfiltration filter has a pore size smaller or equal to 0.45 microns.

Figure 1:
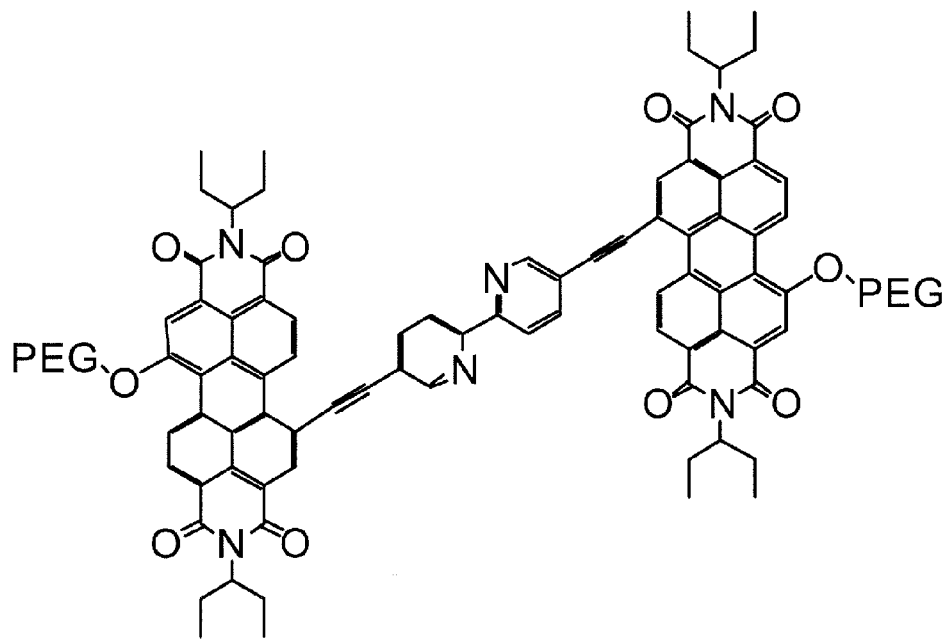
FIG. 1 depicts a Perylene of this invention, wherein the PEG has between 17-21 repeating units.
Figure 2:
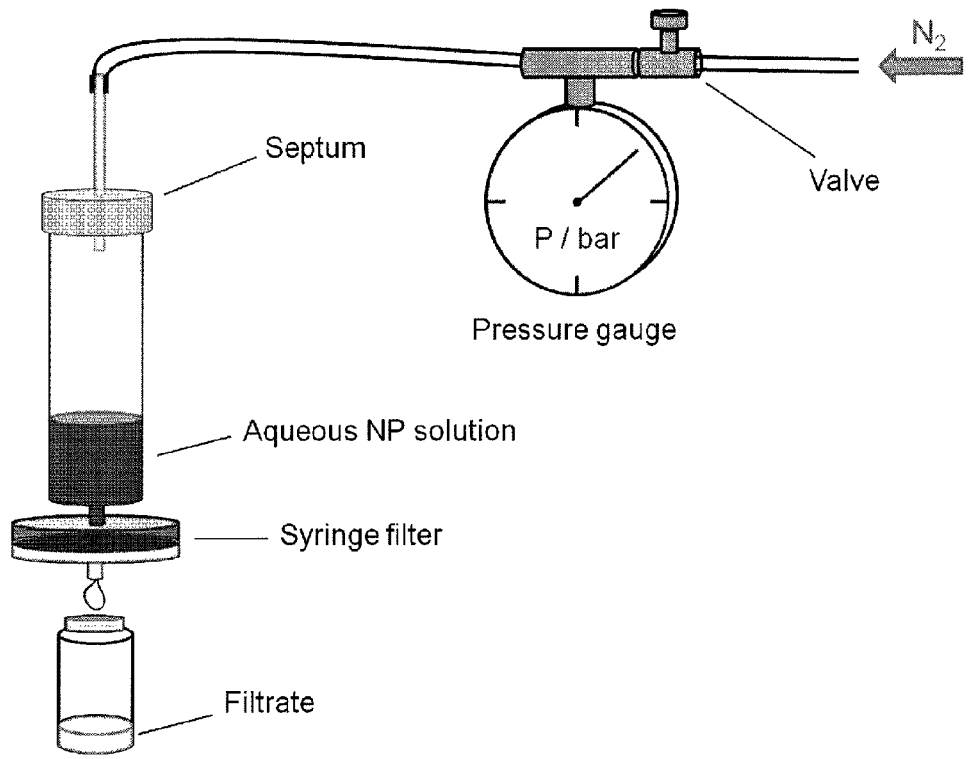
FIG. 2 provides a schematic setup for filter preparation and filtration experiments. Nitrogen entering the system produces the pressure that can be adjusted using a valve and a pressure gauge. Aqueous solution of perylene of this invention, nanomaterial solutions and rinsing water are injected into the system through the septum.

In one embodiment, the method of separation/filtration or purification of nanoparticles is depicted in FIG. 5A-5B and FIG. 2.

In one embodiment, the method of separation/filtration or purification of nanoparticles comprises transferring nanoparticles through the noncovalent self-assembled perylene based membrane. In another embodiment, the transfer of nanoparticles through the membrane is done under pressure. In another embodiment, ultrafiltration is a pressure-driven separation process in which porous membranes retain particles larger than the membrane cut-off (ranging from 2 to 100 nm).

In one embodiment, the method of separation/filtration or purification of biomolecules comprises transferring biomolecules through the noncovalent self-assembled perylene based membrane. In one embodiment, the method of separation/filtration or purification of biomolecules comprises transferring a solution of biomolecules through the noncovalent self-assembled perylene based membrane. In another embodiment, the transfer of biomolecules through the membrane is done under pressure. In another embodiment, ultrafiltration is a pressure-driven separation process in which porous membranes retain particles larger than the membrane cut-off (ranging from 2 to 100 nm).

In one embodiment, the biomolecules solution is an aqueous solution. In another embodiment, the biomolecules solution is a buffered solution. In another embodiment, the biomolecules solution is a solution under physiological conditions.

In one embodiment, the method of separation/filtration or purification of chiral nano-materials comprises transferring nano-materials through the noncovalent self-assembled chiral perylene based membrane. In one embodiment, the method of separation/filtration or purification of chiral nano-materials comprises transferring a solution of nano-materials through the noncovalent self-assembled chiral perylene based membrane. In another embodiment, the transfer of nano-materials through the membrane is done under pressure. In another embodiment, ultrafiltration is a pressure-driven separation process in which porous membranes retain particles larger than the membrane cut-off (ranging from 2 to 100 nm), and/or separate particles having different chirality.

In one embodiment the flow rate of water through 12 μm membrane can be adjusted via the trans-membrane pressure, and stable flow rates are observed at pressures up to 0.7 bar over several hours (FIG. 9). The flow rate at 0.4 bar is 0.4 ml/min, corresponding to permeance (pressure normalized flux) of $1.1 \cdot 10^2$ l h$^{-1}$ m$^{-2}$ bar$^{-1}$ (Example 9).

In one embodiment, the membranes of this invention are readily prepared via one-step deposition of an aggregated perylene diimide of formula I-XIV solution on a microfiltration support. Owing to its noncovalent nature, the material is easily disassembled by organic solvent (e.g. ethanol), the retained particles are released, and the membrane material itself can be recycled and reused multiple times In one embodiment, this invention provides a method of recycling the noncovalent self-assembled perylene based membrane comprising; (a) washing said microfiltration filter with the membrane of this invention and the retenate with a mixture of alcohol and water; (b) extracting said perylene structure with an organic solvent; and (c) isolating said perylene from said organic solvent which can be further used to form a noncovalent self-assembled perylene based membrane in aqueous conditions. In another embodiment the perylene is isolated from said organic solvent by evaporation of the organic solvent. In another embodiment the perylene is isolated from said organic solvent by precipitation of the perylene from said organic solvent.

In one embodiment, a retenate is any material retained on the membrane of this invention during the separation/purification process. In another embodiment the retenate refers to nanoparticles. In another embodiment, the retenate refers to biomolecules. In another embodiment the retenate refers to chiral compounds.

In another embodiment, the supramolecular membrane material is disassembled by organic solvent, cleaned, and can be reassembled, and reused in aqueous conditions, maintaining the same performance. In another embodiment, the perylene maintained its performance as described in Example 10 and FIGS. 10 and 5.

In one embodiment, this invention provides a method of isolating the retenate on the membrane of this invention comprising (a) washing said microfiltration filter with said membrane of this invention and said retenate with a mixture of alcohol and water; (b) extraction of said perylene structure with an organic solvent, and said retenate remain in the aqueous phase. In another embodiment, the retenate refers to nanoparticles. In another embodiment, the retenate refers to biomolecules. In another embodiment, the retenate refers to chiral compounds.

In one embodiment, this invention provides a method of recycling the noncovalent self-assembled perylene based membrane and isolating the retenate on the membrane comprising washing said microfiltration filter with the membrane of this invention and the retenate with a mixture of alcohol and water. In another embodiment, the ratio of said water and alcohol mixture is between about 5:5 to 3:7 v/v. In another embodiment, the ratio of said water and alcohol mixture is about 4:6 v/v. In another embodiment, the alcohol is ethanol, methanol or isopropanol. In another embodiment, the retenate refers to nanoparticles. In another embodiment, the retenate refers to biomolecules.

In one embodiment, this invention provides a method of recycling the noncovalent self-assembly perylene based membrane and isolating the retenate on the membrane comprising; (a) washing the microfiltration filter with the membrane of this invention and the retenate with a mixture of alcohol and water and (b) extracting said perylene structure with an organic solvent, wherein the retenate are in the aqueous phase. In another embodiment the organic solvent is methylene chloride, chloroform, ethyl acetate, ether, benzene toluene or any organic solvent that is immiscible in water.

In one embodiment, this invention is directed to a method of preparing a noncovalent self-assembled perylene based membrane of this invention comprising (a) prepare an organic solution of perylene of this invention, wherein said organic solvent is miscible in water; (b) adding excess of water to said solution of (a); wherein the ratio between said organic solvent to water is between about 3:97 to 8:92 v/v; (c) evaporating said organic solvent; and (d) transferring said aqueous solution or emulsion of (c) through a solid support to obtain a noncovalent self-assembly perylene based membrane.

In another embodiment, this invention is directed to a method of preparing a noncovalent self-assembled perylene based membrane comprising dissolving the perylene in a mixture of an organic solvent which is miscible in water and water wherein the ratio between said organic solvent to water is between about 10:90 to 3:97 v/v. In another embodiment the ratio between the organic solvent and the water is about 5:95 v/v. In another embodiment the ratio between the organic solvent and the water is about 3:97 to 8:92 v/v.

In another embodiment, the miscible organic solvent is THF, acetonitrile, acetone, methanol, ethanol or DMF, or any other miscible organic solvent known in the art.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, and preferably up to 10% of a given value; such as within 7.5%, within 5%, within 2%, within 1%, within 0.5% of a given value.

The following examples are presented in order to more fully illustrate the preferred embodiments of the invention. They should in no way be construed, however, as limiting the broad scope of the invention.

EXAMPLES

Materials and Methods

Solvents and reagents were purchased from commercial sources and used as received, unless otherwise specified. PEG-SH(CH$_3$—(OCH$_2$CH$_2$)$_n$—SH, M$_p$=840 Da, PD=1.04) was purchased from Rapp Polymere. For all aqueous mixtures double-distilled water was used (Barnstead NANO pure Diamond™ water system). Organic solvents for spectroscopic studies were of spectroscopic or HPLC grade, dried over molecular sieves (3 Å), and filtered over 0.2 μm PTFE syringe filters prior to use. All procedures with air-sensitive compounds were performed under inert gas atmosphere (dried N$_2$ or Argon) using a glovebox (MBRAUN, Labmaster) or standard Schlenk techniques. Organic solvents used for these procedures were degassed with Argon and stored over molecular sieves (3 Å) in the glovebox. Water used for air-sensitive samples was degassed by the freeze-pump-thaw technique and kept in the glovebox as well. Cellulose acetate (CA) syringe filters were purchased from Whatman (Puradisc FP 30/0.45 CA-S). PTFE syringe filters were purchased from Pall (Valuprep 25 mm Syringe Filter, 0.45 μm pore size) and from MS (SFPTFE025022NB, 25 mm syringe filter, 0.22 μm pore size). Polycarbonate membranes were purchased from SPI (Black Membrane, 25 mm, 0.4 μm pore size). CA membranes for size-selective chromatography experiments were purchased from Advantec (C045A025A, 25 mm, 0.45 μm pore size). The filter holder for these membranes was purchased from Pall (25 mm Easy Pressure Syringe Filter Holder).

$^1$H NMR spectra were recorded at room temperature on a 300 MHz spectrometer (Bruker).

UV/Vis absorption and luminescence measurements were carried out on a Cary-5000 spectrometer (Varian) and a Cary Eclipse fluorimeter (Varian), respectively.

MALDI-TOF mass spectrometry was carried out using a REFLEX™ reflector time-of-flight instrument with SCOUT™ multiprobe (384) inlet. ESI mass spectrometry was performed using a Micromass Platform instrument. Chloroform was the solvent for all samples analyzed by mass spectrometry.

TEM was performed on a Philips T12 transmission electron microscope operated at 120 kV and equipped with a TVIPS F224HD CCD digital camera. 5 μl of the sample were applied to a 300-mesh copper grid (SPI supplies) coated with nitrocellulose and carbon. Samples were blotted after one minute and dried in air. The images of nanoparticles were analyzed using ImageJ 1.41o (Wayne Rasband, NIH, USA). For creation of particle size histograms, an area containing >100 particles was chosen and diameters of all particles were measured.

Cryo-TEM was performed using a Tecnai F20 transmission electron microscope operating at 200 kV and using a Gatan 626 cooling holder and transfer station with a Gatan US4000 CCD digital camera. For sample-preparation, 8 μl of the sample was applied to a 300-mesh copper grid coated with holey carbon (Pacific Grid-Tech). Samples were blotted in $N_2$-enriched environment at 25° C. and 100% relative humidity, and subsequently plunged into liquid ethane using a CEVS plunger (2). Specimens were equilibrated at −178° C. in the microscope prior to imaging. The images were analyzed using AnalySIS 5.0 (2004, Soft Imaging System GmbH).

Cryo-SEM sample preparation involved the high pressure freezing (HPF) technique. For this purpose, ~1×1 mm small rectangle was cut out from the membrane and placed inside the inner cavity of an aluminium planchette (size=3.0×0.5 mm, inner cavity=2.0×0.15 mm). The vacant space in the cavity was filled with hexadecene and it was capped with the flat side of another aluminium planchette. HPF was carried out using a Bal-Tec HPM 010 high pressure freezing machine. Subsequently, the sandwich was transferred into a Bal-Tech BAF 060 freeze fracture system where it was opened with a pre-cooled razorblade and solvent was allowed to sublime (−105° C., 60 min). Subsequently, it was coated with Ta/W or Pt employing double axis rotary shadowing (DARS). Images were taken in a Zeiss Ultra 55 cryogenic scanning electron microscope operated at 2-5 kV with an aperture size set to 10 μm, utilizing in-lens secondary or backscattered electrons detectors. Importantly, as the preparation of the cryo-SEM samples may slightly affect the supramolecular network (enlargement of the pores due to ice crystals formation), we employed the cryogenic methodology based on HPF that is designed to minimize ice formation.

Example 1

Synthesis of 1,2-bis(N,N'-bis(1-ethylpropyl)-3,4,9,10-tetracarboxylic diimide-7-(polyethylene glycol)-perylen-1-yl)ethyne (Compound III)

A mixture of PEG-PDI-Br (50 mg, 0.036 mmol) and Bis-(tributylstannyl)acetylene (11 mg, 0.018 mmol) was dissolved in toluene (1 ml) and stirred for 10 min. Di-Palladium-tri-Dibenzylideneacetone (1.65 mg, 1.8 μmol) and tri-(t-Butyl)phosphine (0.727 mg, 3.6 μmol) were dissolved in toluene (1 ml) and stirred for 10 min in a separate vial. Then the mixtures were combined and stirred at r.t. for 6 h. accompanied by color change from red to deep purple. Then the reaction mixture was washed with brine and purified by column chromatography (silica 60-200 micron, eluted with acetone/methanol (1:1)) to afford 43 mg of Compound III (Perylene III) as a dark purple solid. Yield 90%.

GPC showed polydispersity of 1.06. $^1$H NMR (CDCl$_3$): δ=10.12 (d, 2H, JHH=8.4, perylene-H), 9.76 (d, 2H, JHH=8.4 Hz, perylene-H), 8.97 (s, 2H, perylene-H), 8.72 (d, 2H, perylene-H), 8.54 (d, 2H, JHH=8.0 Hz, perylene-H), 8.52 (s, 2H, perylene-H), 5.07 (m, 4H, N(CH(CH2CH3)2), 4.69 (m, 4H, PEG), 4.13 (m, 4H, PEG), 3.88 (m, 4H, PEG), 3.80 (m, 4H, PEG), 3.64 (bs, 88H, PEG), 3.37 (m, 6H, PEG-OCH3), 2.27 (m, 8H, N(CH(CH2CH3)2), 1.93 (m, 8H, N(CH(CH2CH3)2), 0.93 (m, 24H, N(CH(CH2CH3)$_2$). $^{13}$C NMR (CDCl$_3$): 157.6, 135.62, 133.39, 129.21, 128.92, 128.4, 128.16, 127.62, 124.09, 120.8, 117.81, 97.69 (PDI-C≡C-PDI), 71.93, 71.08, 70.87, 70.74, 70.57, 69.48, 69.42, 59.04, 57.71, 25.02, 11.39, 11.35.

MS-MALDI-TOF calcd for C140H198N4O44: 2639.34. found 2639 [M+]. UV/vis (CHCl$_3$): λmax/nm (ϵ/M-1 cm-1)= 412.4 (12704), 461.25 (13798), 537.9 (29425), 573.5 (28482), Fluorescence: λmax=693 nm, quantum yield Φf=0.06.

Example 2

Synthesis of Diethynylbenzene-Bridged Perylene Dimmers (Compound IV)

2 eq. of PEG-PDIBr (obtained in a reaction of equimolar amounts of 1,7-PDIBr$_2$, PEGOH and NaH in THF, purified by

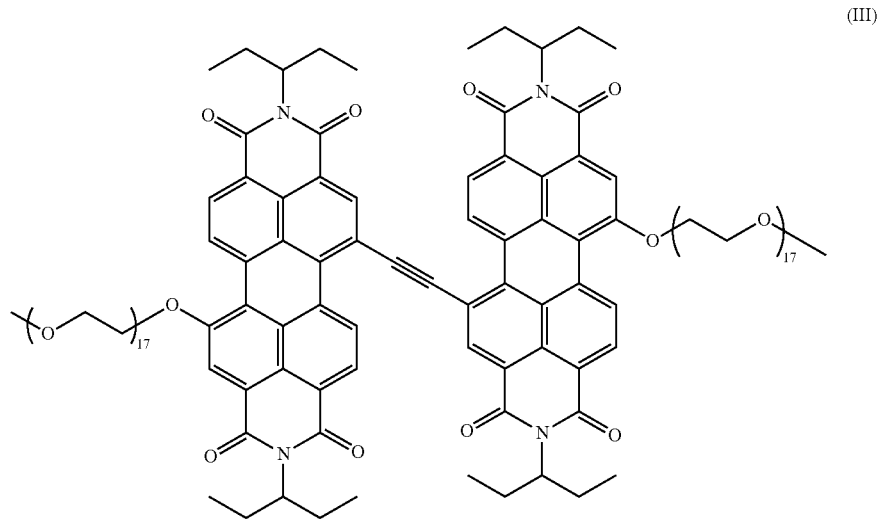

(III)

SiO₂ column, yield 79%) was mixed with 1 eq. of diethynyl benzene in diisopropyl amine at room temperature overnight in the presence of Pd catalyst. The product was separated using column chromatography (SiO₂, chloroform/MeOH as an eluent). Yield 90%.

Example 3

Synthesis of 5,5'-Bis(1-PEG-PDI-7-ethynyl)-2,2'-bipyridine (Compound V)

Synthesis of 5,5'-dibromo-2,2'-bipyridine (3)

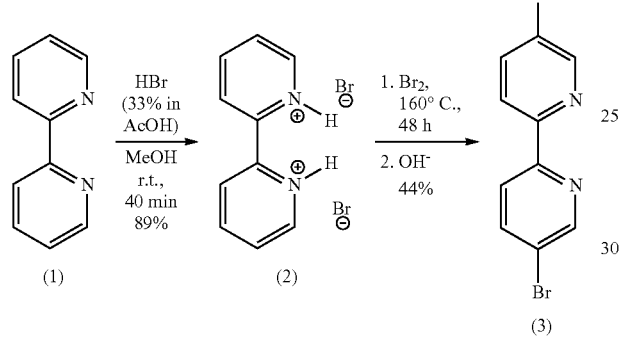

A solution of HBr in acetic acid (5 ml, 33 wt %) was added dropwise to a solution of 1 (0.992 g, 6.35 mmol) in MeOH (2 ml). The instantly forming precipitate was filtered and dried to yield 1.80 g (5.66 mmol, 89%) of 2 as a crude salt. Subsequently, a mixture of 2 (0.975 g, 3.07 mmol) and bromine (981 mg, 6.14 mmol) was heated in a pressure flask to 160° C. for 48 hours with stirring. The reaction was stopped and the hard solid was powdered using mortar and pestle. In order to remove unreacted bromine, a concentrated aqueous solution of Na₂S₂O₃ (60 ml) was added to the brown powder and the mixture was stirred for 10 minutes. Subsequently, it was treated with 1 N NaOH (10 ml) and the product was extracted with CH₂Cl₂ (6×40 ml). The combined organic phases were concentrated under reduced pressure. This lead to partial precipitation of 3 together with unreacted 1. The precipitate was filtered and the two compounds were separated by flash column chromatography on silica gel, using CH₂Cl₂ as an eluent. The mother liquor contained 3, mono-brominated bipyridine, and other products of bromination. 3 was separated from the side products by silica flash column chromatography of the mother liquor using CH₂Cl₂ as an eluent. A total amount of 420 mg (1.34 mmol, 44%) of pure 3 as a white solid was obtained. ¹H NMR (CDCl₃, 250 MHz): δ=8.70 (dd, 2H, $J_{HH}$=0.6 Hz, 2.4 Hz), 8.28 (dd, 2H, $J_{HH}$=0.6 Hz, 8.5 Hz), 7.93 (dd, 2H, $J_{HH}$=2.3 Hz, 8.5 Hz).

Synthesis of 5,5'-Bis((trimethylsilyl)ethynyl)-2,2'-bipyridine (4)

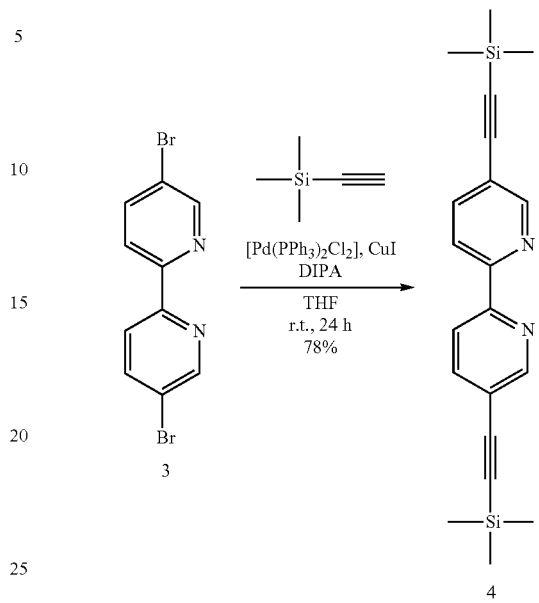

Under dry nitrogen atmosphere, successively trimethylsilyl-acetylene (619 mg, 6.30 mmol), [Pd(PPh₃)₂Cl₂] (112 mg, 159 mol), CuI (54.5 mg, 286 mol) and DIPA (4 ml) were added to a stirred suspension of 3 (500 mg, 1.59 mmol) in 30 ml THF. While the mixture was stirred for 24 hours at room temperature, its color turned black. It was stirred together with activated carbon for 20 minutes and filtered over celite. Then the solvent was removed under reduced pressure, the residue was resuspended in hexane, sonicated for 15 minutes and filtered over celite again yielding an orange solution. The solvent was removed under reduced pressure and the residue was purified by flash column chromatography on silica (eluent: CH₂Cl₂) to yield 430 mg (1.23 mmol, 78%) of pure 4 as an off-white solid. ¹H NMR (CDCl₃, 250 MHz): δ=8.71 (s, 2H, bpy-H), 8.33 (d, 2H, $J_{HH}$=8.3 Hz, bpy-H), 7.85 (d, 2H, $J_{HH}$=7.8 Hz, bpy-H), 0.27 (s, 18H, Si(CH₃)₃).

Synthesis of 5,5'-diethynyl-2,2'-bipyridine (5)

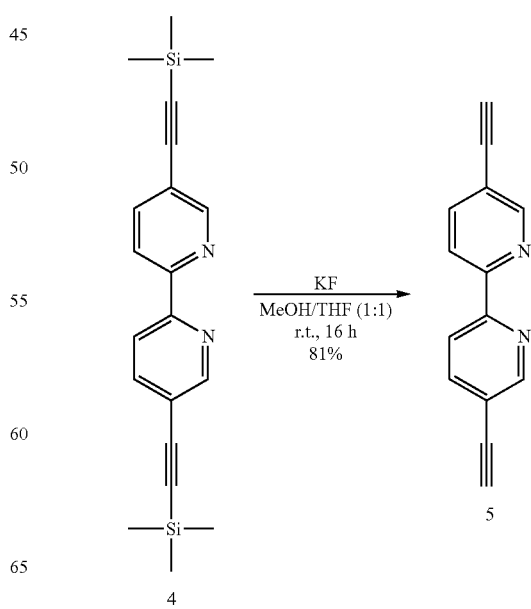

4 (390 mg, 1.12 mmol) was dissolved in a mixture of 40 ml MeOH and 10 ml THF; then KF powder (400 mg, 6.88 mmol) was added and the solution was stirred at room temperature overnight. Subsequently, the solvents were removed under reduced pressure. The residue was redissolved in 200 ml $CH_2Cl_2$ and washed four times with 100 ml $H_2O$ each, in order to remove inorganic salts. The organic phase was dried over $Na_2SO_4$, concentrated under reduced pressure and purified by silica flash column chromatography (eluent: $CH_2Cl_2$) to yield a colorless powder of 204 mg (1.0 mmol, 81%) pure 5. $^1$H NMR (CDCl$_3$, 250 MHz): δ=8.76 (d, 2H, $J_{HH}$=1.0 Hz, bpy-H), 8.39 (d, 2H, $J_{HH}$=6.0 Hz, bpy-H), 7.90 (dd, 2H, $J_{HH}$=1.1 Hz, 5.1 Hz, bpy-H), 3.31 (s, 2H, bpy-CCH).

Synthesis of 1-Br-7-PEG-N,N'-Bis(ethylpropyl) perylene-3,4:9,10-tetracarboxylic diimide (7)

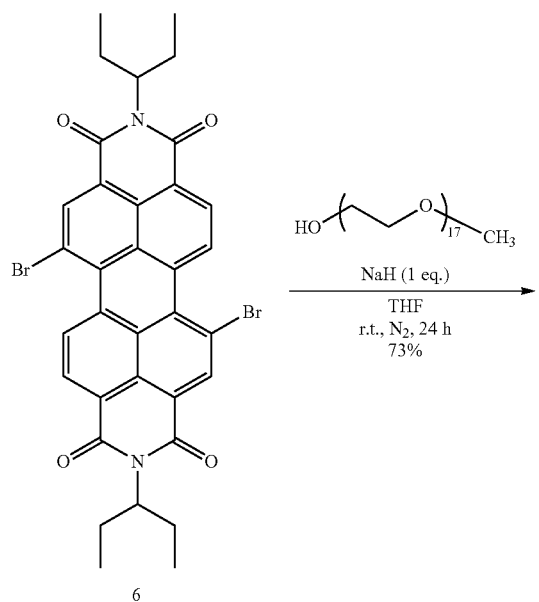

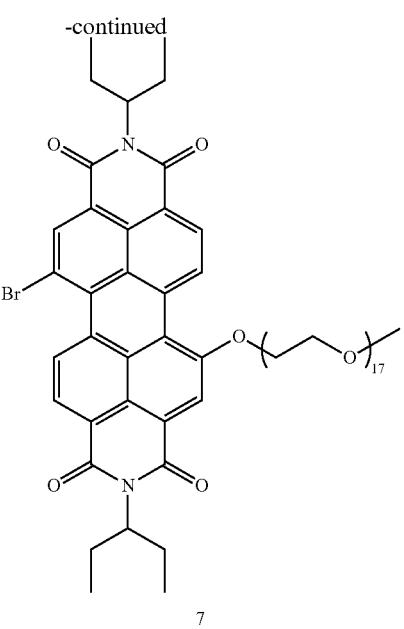

Under dry nitrogen atmosphere, 6 (255.7 mg, 372.7 mol) was dissolved in 30 ml THF in a 100 ml round bottom flask equipped with a magnetic stirrer. Subsequently, dry PEG (371.2 mg, ~485 μmol) was added to the stirring solution, followed by NaH (60 wt %, 20 mg, 500 μmol). Instantly, the color turned darker and after a short time a dark red precipitate formed. The reaction was stopped after 24 hours and the solvent was evaporated under reduced pressure. In order to remove inorganic salts and an excess of PEG, the mixture was treated with 30 ml of water, a few drops of HCl (1N), and 7 was extracted with $CH_2Cl_2$ (3×30 ml). The combined organic extracts were washed with brine (3×30 ml). The solvent was removed under reduced pressure and the resulting dark purple solid was purified by silica gel flash column chromatography. Initially, CHCl$_3$ was used as an eluent, followed by CHCl$_3$/methanol mixtures with a content of methanol rising gradually from 1 to 6 percent. The second band collected contained a red solid yielding 370 mg (269 μmol, 73%) of pure 7. $^1$H NMR (CDCl$_3$, 250 MHz): δ=9.58 (d, 2H, $J_{HH}$=8.3 Hz, perylene-H), 8.91 (s, 1H, perylene-H), 8.65 (d, 1H, $J_{HH}$=8.5 Hz, perylene-H), 8.57 (d, 1H, $J_{HH}$=8.0, perylene-H), 8.45 (s, 1H, perylene-H), 5.05 (m, 2H, N(CH(CH$_2$CH$_3$)$_2$). 4.63 (m, 2H, PEG), 4.07 (m, 2H, PEG), 3.82 (m, 2H, PEG), 3.78 (m, 2H, PEG) 3.70-3.50 (m, 56H, PEG), 3.37 (s, 3H, PEG-OCH$_3$), 2.24 (m, 4H, N(CH(CH$_2$CH$_3$)$_2$), 1.92 (m, 4H, N(CH(CH$_2$CH$_3$)$_2$), 0.90 (m, 12H, N(CH(CH$_2$CH$_3$)$_2$).

Synthesis of 5,5'-Bis(1-PEG-PDI-7-ethynyl)-2,2'-bipyridine (Compound V)

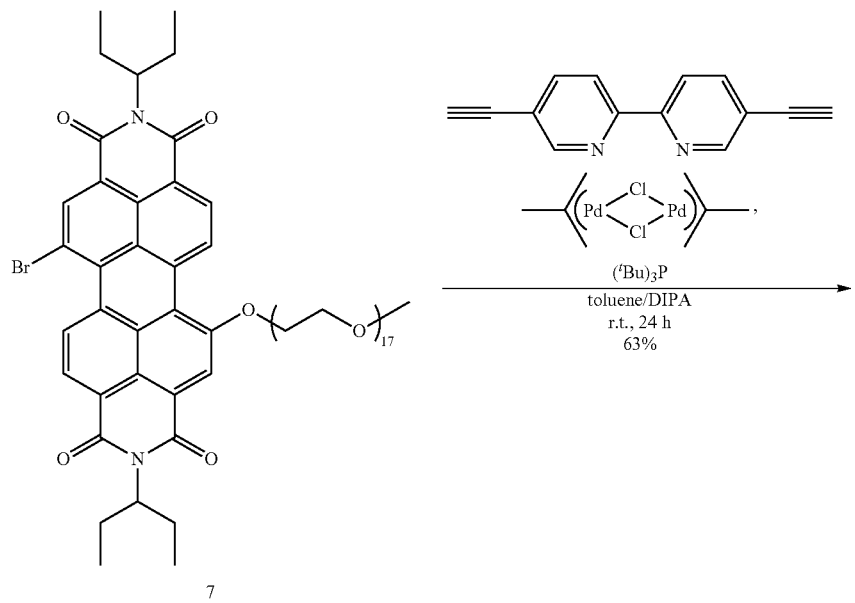

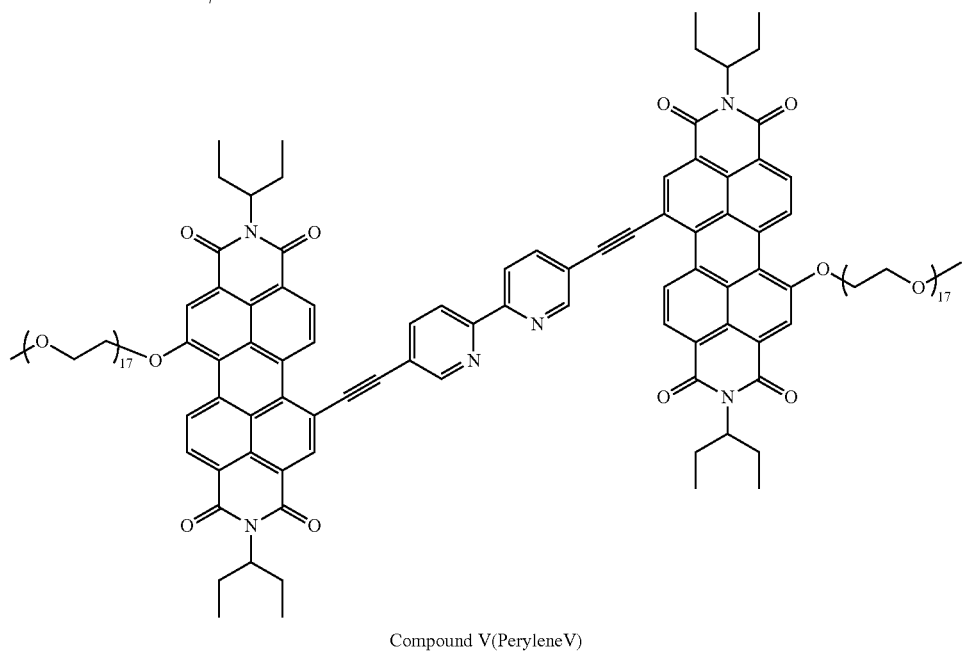

Compound V (Perylene V)

A modified Sonogashira cross-coupling reaction was carried out under nitrogen atmosphere. In contrast to typical Sonogashira reactions, no copper iodide was used as a co-catalyst, in order to prevent coordination of the bpy units to copper ions. To a stirred solution of 7 (315.3 mg, 227 µmol) in 50 ml of dry toluene was added successively a mixture of allyl palladium chloride (6.76 mg, 17.2 µmol) and tris(tert-butyl) phosphine (6.93 mg, 34.3 µmol) in 5 ml toluene, 5,5'-diethynyl-2,2'-bipyridine 5 (20.7 mg, 101 µmol), and 20 ml of DIPA. After stirring for 24 hours at room temperature, the solvents were evaporated and the crude product was dried in high vacuum for several hours. It was purified using silica gel flash column chromatography with $CHCl_3$/MeOH mixtures as an eluent, starting from pure $CHCl_3$, and subsequently raising the MeOH content to 6%. A red solid was obtained from the second band, yielding 179.2 mg (64 µmol, 63%) of pure Compound V.

$^1$H NMR ($CDCl_3$, 500 MHz): δ=10.08 (d, 2H, $J_{HH}$=8.5 Hz, perylene-H), 9.73 (d, 2H, $J_{HH}$=8.5 Hz, perylene-H), 8.97 (s, 2H, bpy-H), 8.94 (s, 2H, perylene-H), 8.68 (dd, 4H, $J_{HH}$=8.5 Hz, 8.0 Hz, perylene-H, bpy-H), 8.62 (d, 2H, $J_{HH}$=8.0 Hz, perylene-H), 8.51 (s, 2H, perylene-H), 8.10 (d, 2H, $J_{HH}$=8.0 Hz, bpy-H), 5.09 (m, 4H, N(CH($CH_2CH_3$)$_2$), 4.67 (m, 4H, PEG), 4.11 (m, 4H, PEG), 3.50-3.75 (m, 120H, PEG), 3.37 (s, 6H, PEG-O$CH_3$), 2.29 (m, 8H, N(CH($CH_2CH_3$)$_2$), 1.96 (m, 8H, N(CH($CH_2CH_3$)$_2$), 0.94 (m, 24H, N(CH($CH_2CH_3$)$_2$).
$^{13}$C {H}NMR ($CDCl_3$, 125 MHz): δ=164 (br., carbonyl), 157.65, 154.88, 152.05, 139.64, 137.57 (br.) 135.47, 134.34, 133.73, 132.11 (br. s), 129.30, 129.17, 128.5 (br.), 128.41, 128.22, 124.4 (br.), 124.21, 123.6 (br.), 122.1 (br.), 121.29, 121.01, 120.12, 118.24, 95.64 (ethynyl), 93.70 (ethynyl), 72.09 (PEG), 71.23 (PEG), 71.02-70.05 (PEG), 69.63 (PEG), 69.56 (PEG), 59.20 (PEG-O—$CH_3$), 57.98, 57.83 (N(CH($CH_2CH_3$)$_2$), 25.20 (N(CH($CH_2CH_3$)$_2$), 11.51 (N(CH($CH_2CH_3$)$_2$).

MALDI-TOF-MS m/z calc. for $C_{148}H_{196}N_6O_{42}$: 1730.3. found: 1754.7 [M+Na$^+$]. UV/Vis (CHCl$_3$): $\lambda_{max}$/nm ($\epsilon$/M$^{-1}$cm$^{-1}$) 577.8 (42,700), 539.3 (33,400), 386.4 (39800). Fluorescence (CHCl$_3$): $\lambda_{max}$/nm: 604.0, fluorescence quantum yield, $\Phi_f$) 0.58. GPC: Polydispersity 1.15, molecular weight≈3000 Da. Redox potentials (E vs. SCE): +1.49 V (M$^+$+e$^-$⇌M), −0.68 V (M+e$^-$⇌M$^-$), −0.88 V (M$^-$+e$^-$⇌M$^{2-}$).

The large and rigid aromatic core of Compounds III-V containing PDI, bipyridyl, and acetylene moieties, is highly hydrophobic, whereas the two PEG tails are hydrophilic. This amphiphilicity allows a bottom-up approach for the design of supramolecular structures. The hydrophobic moieties guarantee aggregation driven by π-π interactions and the hydrophobic effect, whereas the hydrophilic PEG tails are dissolved well in aqueous medium preventing precipitation.

Example 4A

Synthesis of Gold/MPA Nanoparticles (Au1-4)

Mercaptopropionic acid (MPA)-stabilized gold nanoparticles of different sizes were prepared according to a modified literature procedure [T. Yonezawa, T. Kunitake, Practical preparation of anionic mercapto ligand-stabilized gold nanoparticles and their immobilization. *Colloids Surf, A* 149, 193 (1999)] which is incorporated herein by reference.

Round bottom flasks and magnetic stirrers were washed carefully with aqua regia, Piranha ($H_2SO_4$/$H_2O_2$, 7:1), and double distilled water (Nanopure system). MPA-Na was prepared by neutralizing MPA with NaOH.

A solution of HAuCl$_4$·3H$_2$O (57 mg, 0.145 mmol) in 25 ml water was added to 250 ml of refluxing water. Then 25 ml of a mixed solution of MPA-Na (see Table 1) and trisodium citrate. 2H$_2$O (500 mg, 1.70 mmol) was added rapidly. The solutions were refluxed for 6 hours. For separation from the excess of salts, the dispersions were treated with HCl (2M) until aggregated particles precipitated. The precipitate was removed from the mother liquor by centrifugation. Then it was re-dispersed by adding 250 ml of water and adjusting the pH to 9 using NaOH (1M).

TABLE 1

MPA-Na used for synthesis of Au1-4.

| | Au1 | Au2 | Au3 | Au4 |
|---|---|---|---|---|
| MPA-Na (mmol) | 0.435 | 0.145 | 0.073 | 0.015 |
| Average particle diameter (nm) | 1.6 ± 0.6 | 2.8 ± 1.5 | 7.1 ± 5.9 | 17.5 ± 3.9 |

Example 4B

Synthesis of Gold/Citrate Nanoparticles (Au5)

Au5 was synthesized according to a literature procedure [R. Kaminker et al., Molecular Structure-Function Relations of the Optical Properties and Dimensions of Gold Nanoparticle Assemblies. *Angew. Chem. Int. Ed.* 49, 1218 (2010)] that employs a modified Turkevich method [J. Kimling et al., Turkevich Method for Gold Nanoparticle Synthesis Revisited. *J. Phys. Chem. B* 110, 15700 (2006); J. Turkevich, P. C. Stevenson, J. Hillier, A study of the nucleation and growth processes in the synthesis of colloidal gold. *Discuss. Faraday Soc.* 11, 55 (1951)] which are incorporated herein by reference.

Example 4C

Synthesis of Gold/CTAB Polydisperse Nanoparticles (Au6) and Nanorods (Au7)

Au6 was formed in water by addition of NaBH$_4$ (55 µl, 0.25 µM) into a growth solution containing previously recrystallized cetryl trimethyl ammonium bromide (CTAB) (10 ml, 0.2 M), HAuCl$_4$ (200 µl, 1 mM), AgNO$_3$ (40 µl, 0.2 mM) and ascorbic acid (400 µl, 2 mM). The color of the solution turned blue within a few minutes. The mixture was kept at r.t. overnight. The particles were purified by repetitive (3×) centrifugation and redispersion in water.

Au7 was synthesized according to the seed mediated procedure reported by Murphy et al. B. D. Busbee, S. O. Obare, C. J. Murphy, An Improved Synthesis of High-Aspect-Ratio Gold Nanorods. *Adv. Mater.* 15, 414 (2003); which is incorporated herein by reference.

Example 5

Synthesis of Gold/PEG-SH Nanoparticles (Au8)

PEG-SH stabilized nanoparticles were prepared using a modified Brust-Schiffrin method [M. Brust, M. Walker, D. Bethell, D. J. Schiffrin, R. Whyman, Synthesis of thiol-derivatised gold nanoparticles in a two-phase Liquid-Liquid system. *J. Chem. Soc., Chem. Commun.,* 801 (1994); and W. P. Wuelfing, S. M. Gross, D. T. Miles, R. W. Murray, Nanometer Gold Clusters Protected by Surface-Bound Monolayers of Thiolated Poly(ethylene glycol) Polymer Electrolyte. *J. Am. Chem. Soc.* 120, 12696 (1998)] which are incorporated herein by reference. In the glovebox, tetraoctylammonium bromide (TOAB, 23 mg, 42 µmol) in toluene (6 ml) was added to HAuCl$_4$·3H$_2$O (10 mg, 25 µmol) in water (3 ml) and the mixture was stirred for 30 minutes transferring Au(III) ions to the organic phase. The aqueous phase was removed, then PEG-SH (2.0 mg, 2.4 µmol) in toluene (100 µl) was added and the mixture was taken out of the glove box. To this solution, a freshly prepared solution of NaBH$_4$ (11.2 mg, 0.30 mmol) in H$_2$O (3 ml) was added under vigorous stirring over a period of 15 seconds. During that time the organic phase became brown and within 1 min this color was transferred to the aqueous phase. The mixture was stirred for 90 minutes. Subsequently, the two phases were separated, dichloromethane (DCM) (6 ml) was added to the aqueous phase, and the nanoparticles were salted out into the organic phase with a minimal amount of NaCl. The organic phase was dried in high vacuum. Then acetonitrile (3 ml) was added to re-dissolve the nanoparticles, leaving behind a small amount of white precipitate. The solution was filtered over a 0.2 µm cellulose acetate (CA) filter and dried in high vacuum, yielding 5.5 mg nanoparticles, which were dissolved in water (20 ml). The nanoparticles were protected from light and aged for 6 months at room temperature prior to use.

Example 6

Synthesis of CdTe/MPA Quantum Dots (QD1, QD2)

Quantum dots QD1 and QD2 were synthesized according to a literature procedure [H. Zhang, Z. Zhou, B. Yang, M.

Gao, The Influence of Carboxyl Groups on the Photoluminescence of Mercaptocarboxylic Acid-Stabilized CdTe Nanoparticles. *J. Phys. Chem. B*107, 8 (2003)] which is incorporated herein by reference. The synthesis was carried out under argon atmosphere. Briefly, a solution of $CdCl_2 \cdot H_2O$ (114.5 mg, 1.25 mM) and MPA (105 µl, 3.0 mM) in water (400 ml) was adjusted to pH 9 using NaOH (1 M). Subsequently, a freshly prepared solution of NaHTe (250 µl, 1 M) (14) was added and the mixture was refluxed. QD2 was obtained after 240 min and QD1 was obtained after 24 h reaction time. The particles were purified as described in the literature Zhang et al. *J. Phys. Chem. B*107, 8 (2003).

Example 7

Self-Assembly of Compound V

In a typical experiment, Compound V (100 mg, ~36 µmol) was first dissolved in THF (3.6 ml). Then water was added in portions (3×22.5 ml), each addition was followed by vigorous mixing of the solution and sonication for 5 minutes. After adding the last portion, the mixture contained 5% THF and 95% water at a Compound V concentration of $5 \cdot 10^{-4}$ M. It was sonicated for 20 min. Subsequently, THF was removed by evaporating ~40 vol % of the solution at room temperature in the high vacuum and the reduced volume was refilled with water. Removal of THF was confirmed by $^1$H NMR spectroscopy of a THF/$D_2O$ solution of Compound V after applying this procedure (FIG. 28). The aggregated solution of Compound V in water was aged for one day and used as a stock solution for preparation of supramolecular filtration membranes.

Example 8

Preparation of Supramolecular Filtration Membranes

In a typical experiment, 0.5 ml of self-assembled Compound V in water ($5 \cdot 10^{-4}$ M) was filtered over a syringe filter (Whatman Puradisc FP 30, CA, effective filtration area=5.7 $cm^2$, pore size=0.45 µm). Care was taken to avoid the presence of air bubbles in the chamber, which would affect the formation of a homogeneous layer of supramolecular material. Subsequently, 3 ml rinsing water (containing 0.1 mM nanoparticle capping agent (e.g. MPA) adjusted to the pH of the nanoparticle solution) was filtered over the membrane at a constant trans-membrane pressure of 0.4 bar, in order to stabilize material packing and flow rate. The filter housing was kept filled with aqueous solvent and the supramolecular membrane was used directly for filtration experiments. (FIG. 2)

Cryogenic transmission electron microscopy (cryo-TEM) of the aqueous solution confirms the presence of interacting supramolecular fibers (FIG. 11)

Example 9

Filtration of Nanoparticles 3 ml of the nanoparticle solution was filtered over the supramolecular filtration membrane at a constant pressure of 0.4 bar using the setup depicted in FIG. 29. 3 ml of filtrate was collected after the dead volume of 1 ml solution passed through the filter housing. Subsequently, the filter was rinsed with 6 ml water (containing 0.1 mM nanoparticle capping agent at the pH of the nanoparticle solution).

Figure 3:
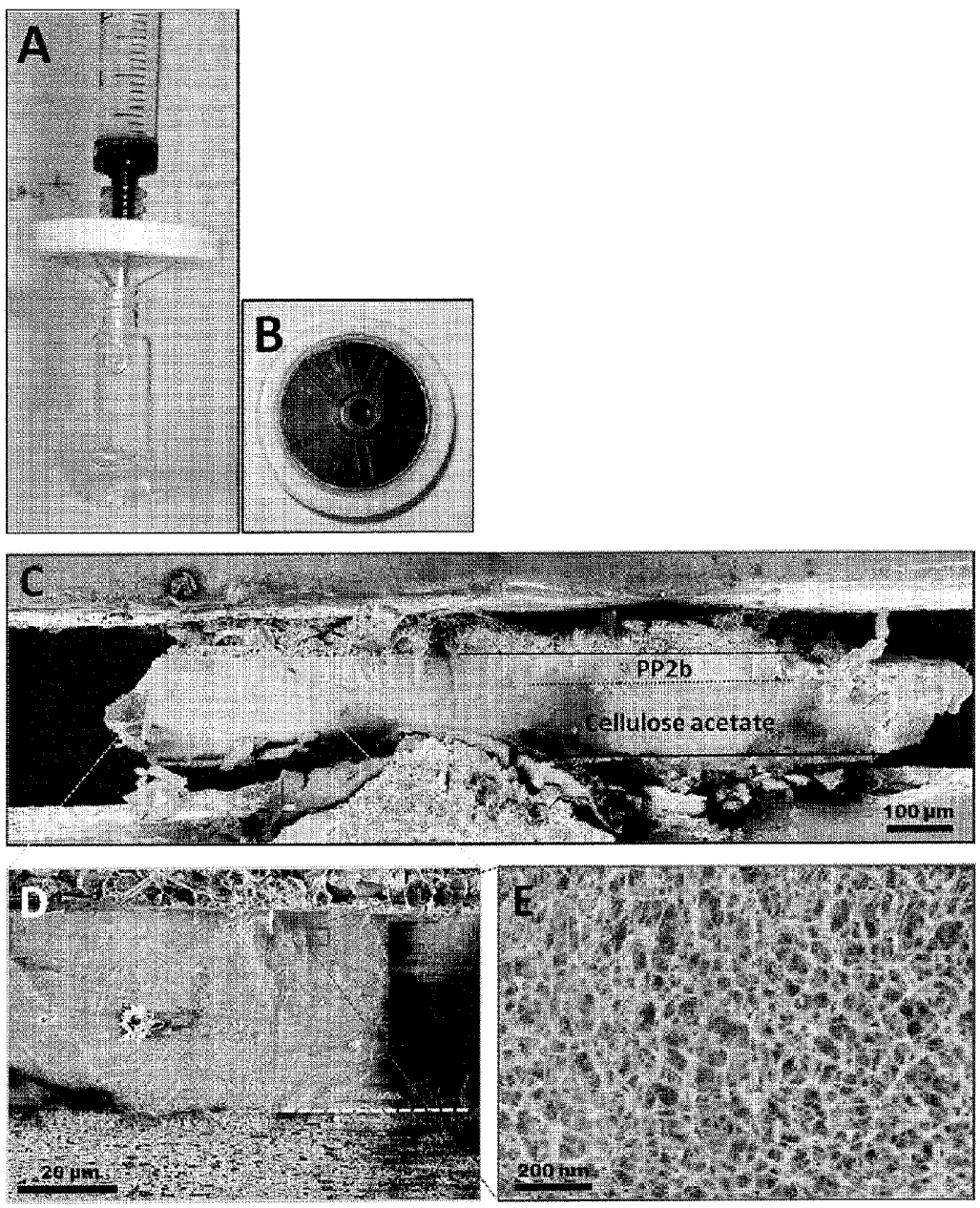
FIG. 3 (A) presents a photograph showing filtration of a supramolecular solution of Perylene V ($5 \cdot 10^{-4}$ M) in water over cellulose acetate (CA) filter (0.45 µm pore size). (B) Photograph of supramolecular material deposited on top of the cellulose acetate (CA) support in the commercial syringe filter. (C) Cryo-SEM image of the cross-section of a ~1×1 mm piece of the supramolecular membrane (0.65 mg Perylene V/cm$^2$) on CA support. (D) Magnified image showing the sharp border between coarse CA and smooth Perylene V layer (dashed line). (E) High magnification image of the supramolecular Perylene V layer. (PP2b in the figure refers to Perylene V)

Filtration of the supramolecular solution over commercial microfiltration syringe filters results in a colorless filtrate and quantitative deposition of Compound V on top of the microfiltration support (FIG. 3A, B). While this simple one-step deposition is feasible using various commercial microfiltration membranes (e.g. cellulose acetate (CA), teflon (PTFE) or polycarbonate; 0.22 or 0.45 µm pore size), in the further experiments, CA was chosen as support membrane, since it is inexpensive and allows high flow rates for water.

A deposited supramolecular layer prepared by filtration of 2.5 ml of aqueous perylene of formula V (Compound V) ($5 \cdot 10^{-4}$ M) over CA (0.45 µm pore size, 5.7 $cm^2$ surface area; 0.65 mg Perylene V/$cm^2$) was investigated using cryogenic scanning electron microscopy (cryo-SEM). Images of the filter cross-section show a homogeneous ~45 µm thick layer of the supramolecular material on top of the CA support (FIG. 3C).

A sharp border between the coarse CA and the smooth supramolecular layer suggests that Perylene V (Compound V) fibers do not penetrate notably into the pores of the CA (FIG. 3D). Higher magnifications reveal the three dimensional fibrous network in the supramolecular layer (FIG. 3E). Importantly, the deposited supramolecular system exhibits uniform nanostructured network, with voids that may play a role of nanopores during filtration.

The membrane thickness can be readily controlled by the ratio of PeryleneV solution volume to filter surface area. Thus, filtering only 0.5 ml Perylene V ($5 \cdot 10^{-4}$ M) over CA (0.13 mg Perylene V/$cm^2$) resulted in reduction of Perylene V layer thickness to ~12 µm (FIG. 12). The one-step fabrication of the supramolecular membrane is exceedingly simple and preparation from a stock solution of self-assembled Perylene V takes ~15 minutes.

The flow rate of water through the 12 µm membrane can be adjusted via the trans-membrane pressure, and stable flow rates are observed at pressures up to 0.7 bar over several hours (FIG. 9). The flow rate at 0.4 bar is 0.4 ml/min, corresponding to permeance (pressure normalized flux) of $1.1 \cdot 10^2$ l $h^{-1}$ $m^{-2}$ $bar^{-1}$, which is comparable to commercial ultrafiltration membranes with similar rejection properties. Importantly, no traces of Perylene V (Compound V) are detectable in the filtrate of the water solution (FIG. 10), revealing the robustness of the supramolecular membrane material under the solvent flow.

Example 10

Recycling of Filtration Membrane and Nanoparticles 5 ml of water/ethanol (4:6, v/v), containing nanoparticle capping agent (0.04 mM), was flown through the supramolecular membrane in order to wash Perylene V (Compound V) and retained NPs off the CA support. Subsequently, Perylene V was extracted with 12 ml DCM. The organic phase was partially evaporated in high vacuum; Perylene V was precipitated with hexane and dried in high vacuum.

Aunts in the aqueous phase were purified by successive addition of 3 ml EtOH and 12 ml DCM, leading to removal of traces of Perylene V. The aqueous phase was washed with DCM and partially evaporated in high vacuum in order to remove traces of organic solvent. Then it was refilled to 3 ml with an aqueous solution containing NP capping agent (0.1 mM).

Thus, rinsing the supramolecular filter with a water/ethanol mixture (4:6, v/v) results in disassembly of Perylene V and its complete removal from the CA support (FIG. 20). The Perylene V can be dried, reassembled in water, and reused as a membrane.

Figure 4:
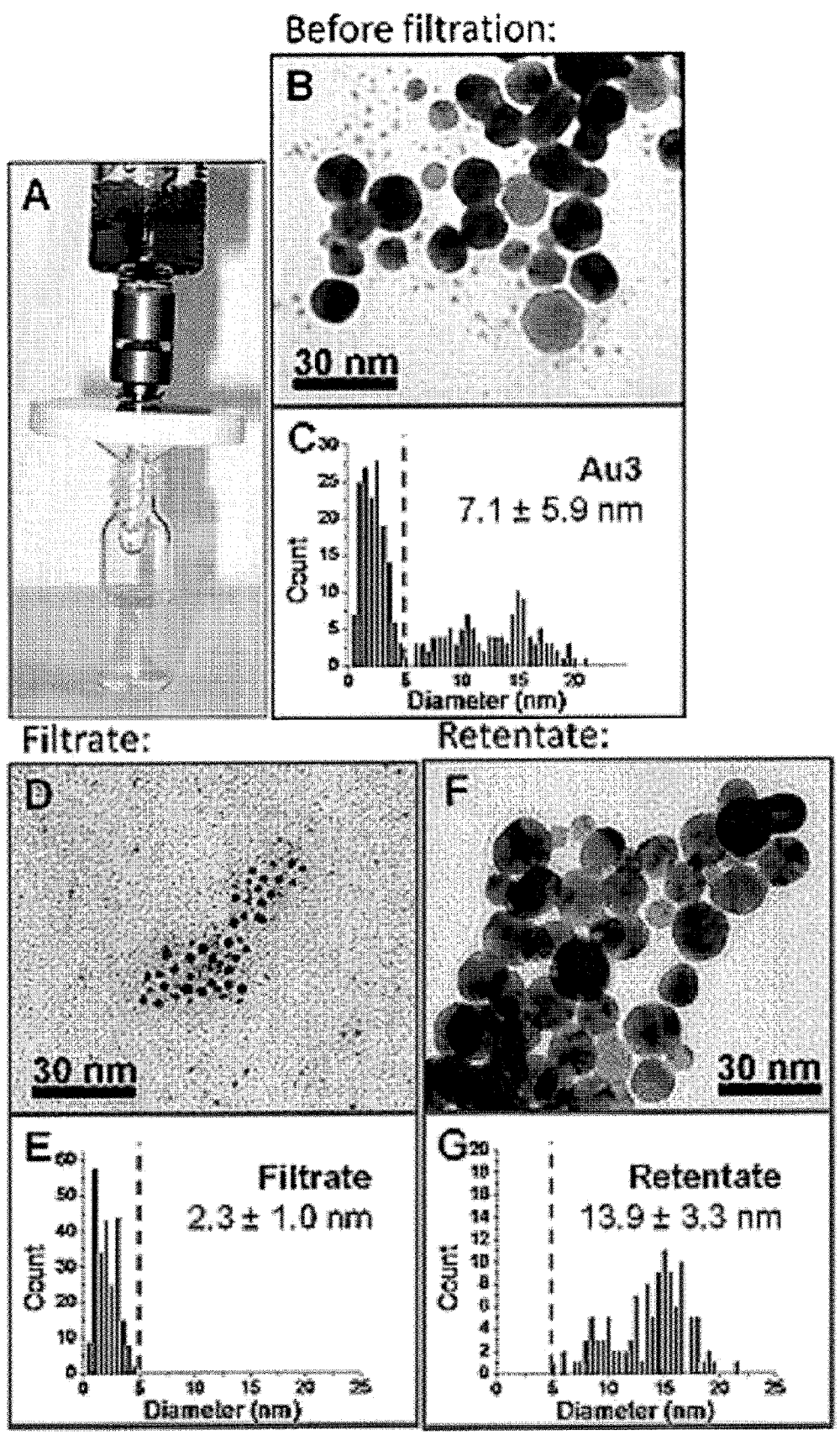
FIG. 4 (A) presents photograph of the filtration experiment of Au3. (B) Representative TEM image of Au3 before filtration and (C) corresponding particle size histogram. (D) TEM image of the filtrate and (E) corresponding histogram. (F) TEM image of the retentate and (G) corresponding histogram; dashed lines in the histograms indicate the cut-off of the filter. Representative TEM images of larger areas are provided in FIG. 21-23. (H) UV/Vis spectra of a Au3 solution before filtration (solid line), retentate (dashed line), and filtrate (dotted line). (I) Photographs showing the retrieval of Perylene V and AuNPs from the water/ethanol mixture. (PP2b in the figure refers to Perylene V).
Figure 4:
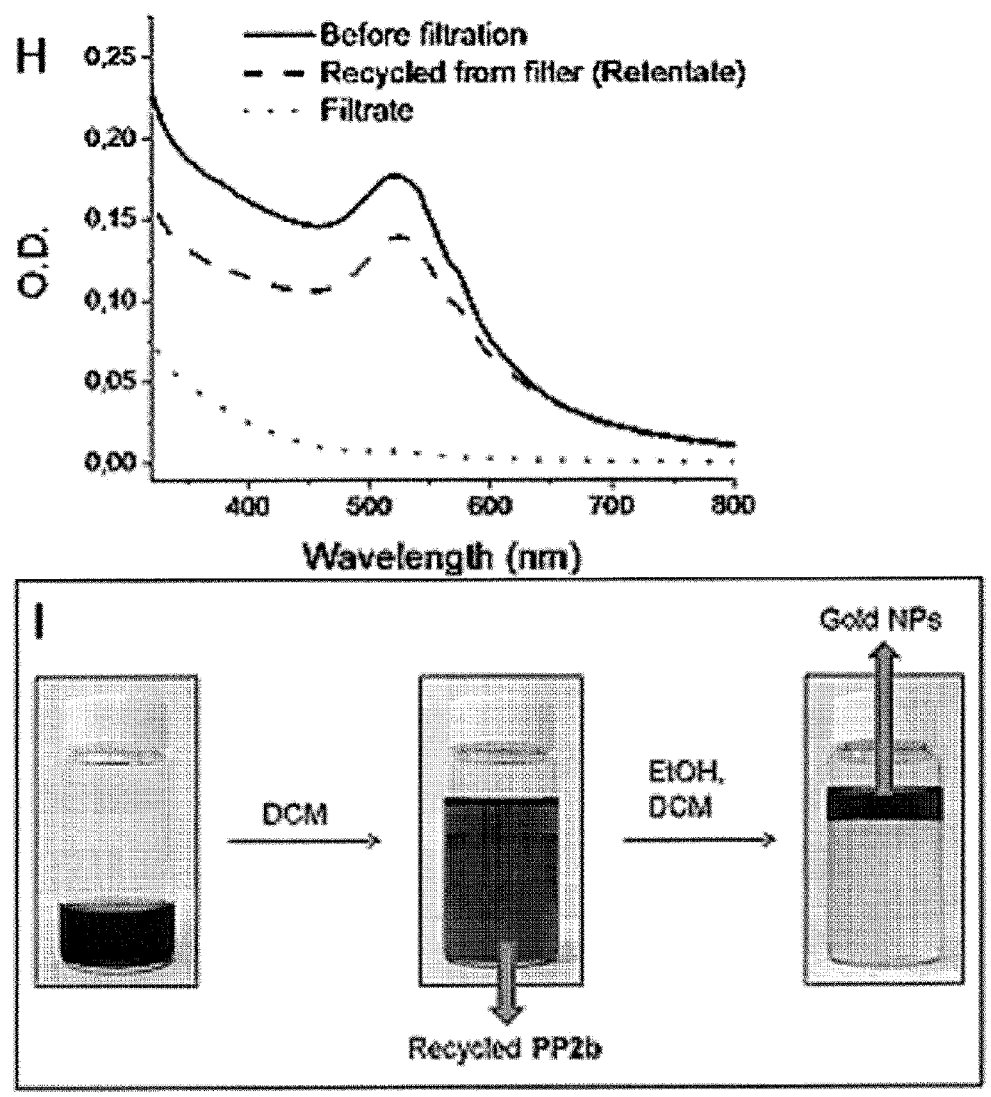

Through this procedure, both Perylene V and retained NPs (retentate) could be recycled (FIG. 4I). As revealed by TEM, the retentate contains particles larger than 5 nm, matching well with the fraction of particles that are missing in the filtrate (FIG. 4F, G). In agreement with this observation, the UV/Vis spectrum of the retentate solution shows a strong Plasmon resonance band SPB at 524 nm, characteristic of the larger AuNPs in Au3 (FIG. 4H). The absence of Perylene V absorption peaks ($\lambda_{max,1}$=394 nm, $\lambda_{max,2}$=540 nm) in the isolated retentate solution shows that the extraction of the strongly absorbing amphiphile with DCM is quantitative.

$^1$H-NMR spectra measured before and after the recycling procedure do not indicate any decomposition or contamination of Perylene V (FIG. 29), which is important for its multiple recycling and reproducible use as supramolecular membrane.

The Perylene V material was recycled and reused 3 times, showing consistent performance. The experiments demonstrate that reversible bonding in Perylene V supramolecular structures allows facile recycling of both the membrane material and retained NPs. The CA support can be recycled as well. A scheme depicting membrane fabrication, use, and recycling is shown in FIG. 5A-5B.

Example 11

Size-Selective Chromatography

In order to study applicability for ultrafiltration, gold nanoparticles (AuNPs) of various sizes were filtered over a ~12 μm thick Perylene V (Compound V) supramolecular membrane (0.13 mg Perylene V/cm$^2$, FIG. 12). Filtration experiments were preformed in a setup (FIG. 2) that allows filtration under a constant trans-membrane pressure (0.4 bar was used in all filtration experiments). AuNP solutions were characterized before and after filtration using transmission electron microscopy (TEM). In addition, UV/Vis was used for qualitative corroboration of TEM image analysis, since a surface plasmon band (SPB) is dependent on the particle size.

Mercaptopropionic acid (MPA)-stabilized AuNPs Au3 (7.1±5.9 nm) have a bimodal, highly polydisperse particle size distribution with particles ranging from 0.5 to ~20 nm in diameter (FIG. 4B, C). Filtration of the red solution over the supramolecular Perylene V membrane results a pale yellow filtrate (FIG. 4A). The UV-Vis spectrum shows the absence of a SPB in the filtrate (FIG. 4H), suggesting the removal of particles larger than ~5 nm. TEM images of the filtrate show size-selective removal of large particles (~5 nm cutoff size) and reduction of average particle size from 7.1 to 2.3 nm (FIG. 4D, E).

Figure 6:
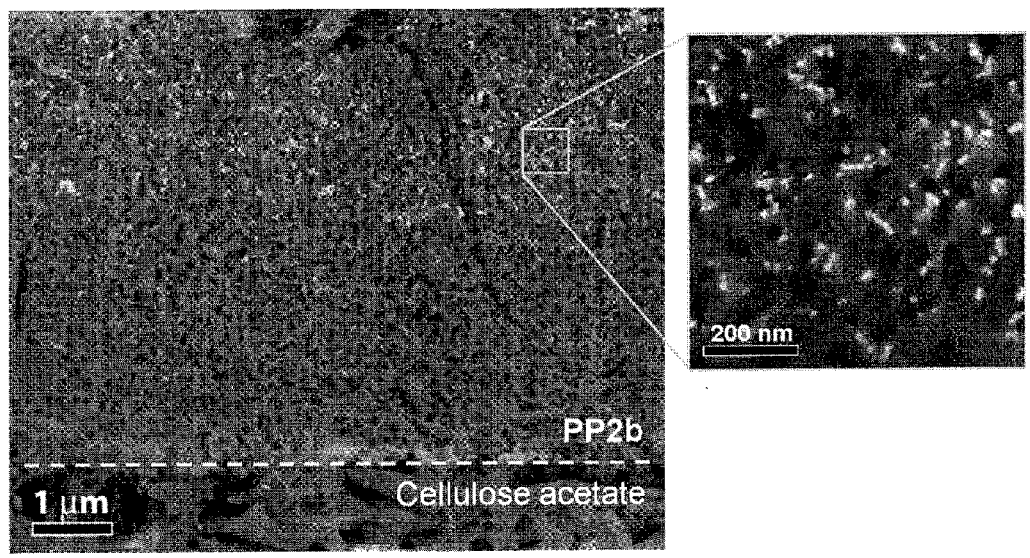
FIG. 6 depicts a cryo-SEM image (back-scattered electron analysis) of the supramolecular membrane that was used for filtration of Au3 solution. AuNPs (appearing as bright spots) have sizes of 10-20 nm. (PP2b in the figure refers to Perylene V).

In order to visualize filtered nanoparticles embedded in the supramolecular membrane, filtration of Au3 was investigated using cryo-SEM. When detecting back-scattered electrons, AuNPs appear as a band of bright spots that penetrated into the filtration membrane rather than being retained on its surface and forming a filter cake (FIG. 6). The magnified area shows individual particles with diameters corresponding to the larger particle fraction in the Au3 size distribution. The particles appear to be neither fused nor aggregated.

Figure 7:
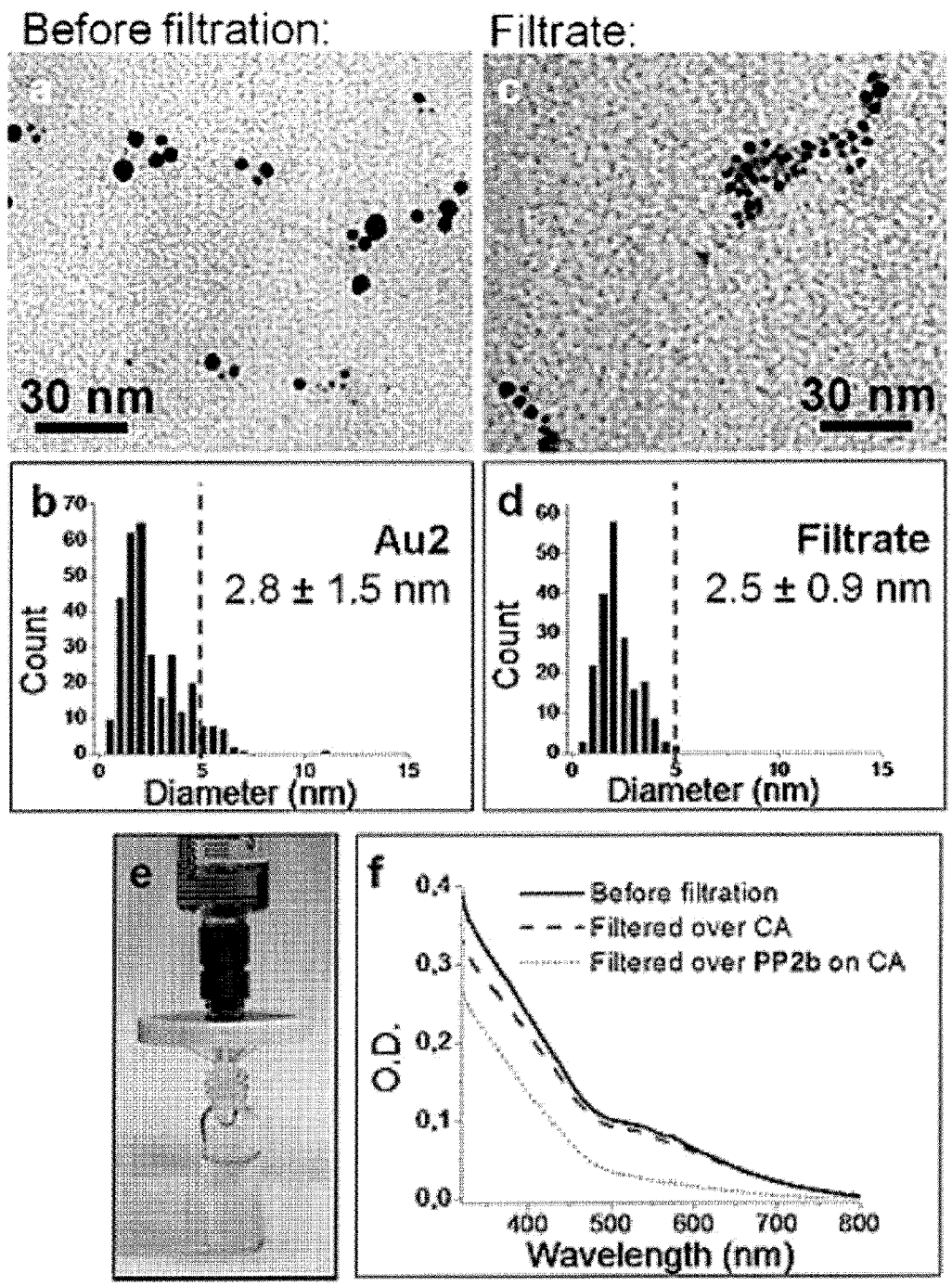
FIG. 7(A)-(F) Filtration experiment of Au2. (A) Representative TEM image of particles before filtration, and (B) particle size histogram. (C) Representative TEM image of particles in the filtrate, and (D) particle size histogram. (E) Photograph of filtration. (F) UV/Vis spectra of an Au2 solution before filtration (solid line), after filtration over CA (control measurement, dashed line), and after filtration over the Perylene V supramolecular membrane (dotted line). Filtration of Au2 over CA does not change any spectral features and the SPB (surface plasmon band) at ~520 nm remains unchanged, indicating that all particles pass CA. In contrast, no SPB is visible in the sample filtered over the supramolecular Perylene V membrane, indicating removal of particles larger than 5 nm.
Figure 7:
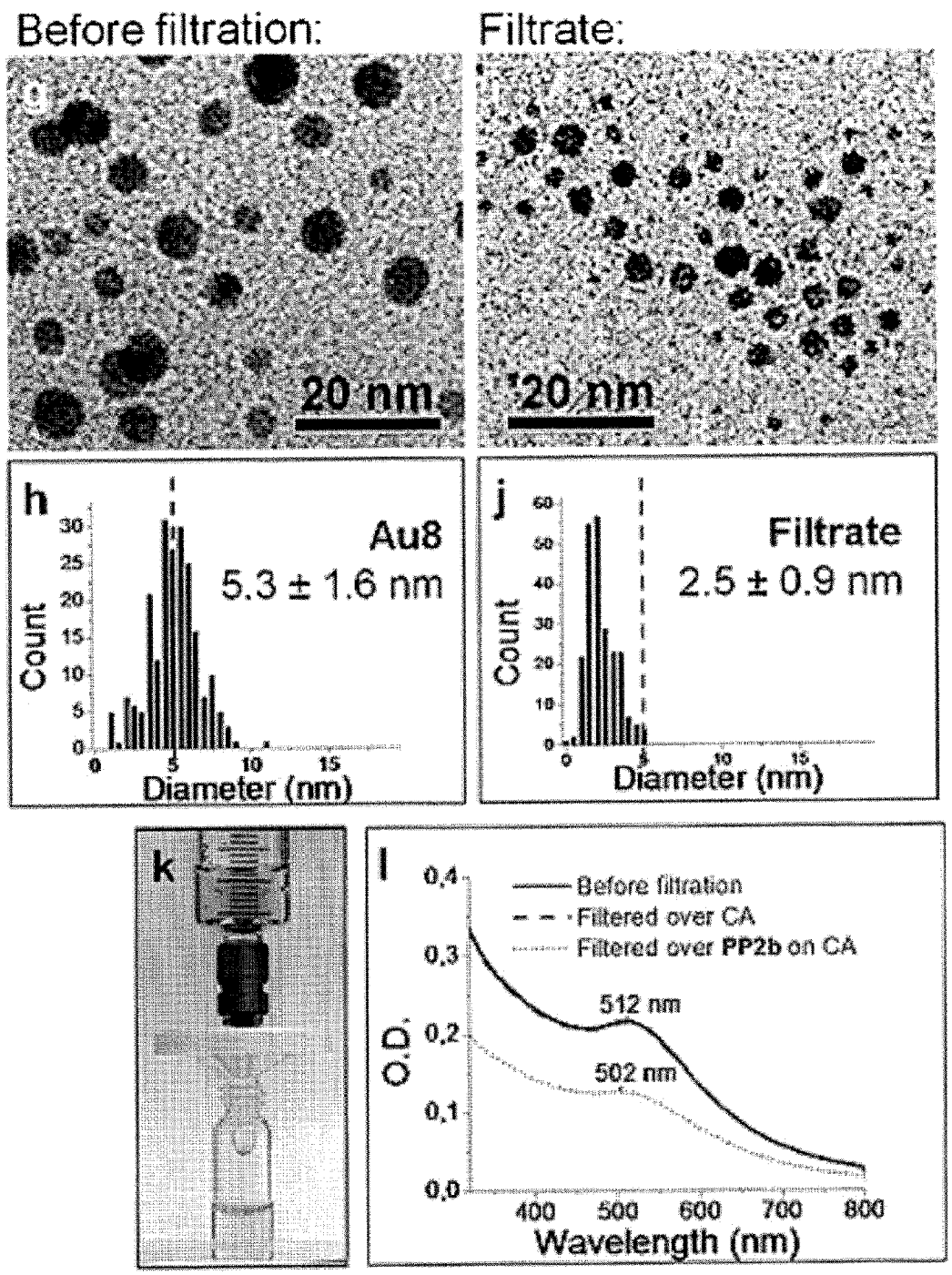

Filtration experiments with other MPA-stabilized AuNPs are in agreement with the filter's ~5 nm cutoff size: small Au1 (1.6±0.6 nm) pass the supramolecular membrane (FIG. 13, 14), while large Au4 (17.5±3.9 nm) are filtered off quantitatively (FIG. 15 and FIG. 16). Filtration of polydisperse Au2 (2.8±1.5 nm) resulted in removal of particles larger than 5 nm and improved monodispersity of the nanoparticles (FIG. 7 A-F).

The supramolecular membrane maintains similar rejection properties when AuNPs are stabilized by other capping layers: Filtration of PEG-5H-stabilized Au8 (5.3±1.6 nm) leads to removal of particles larger than 5 nm (FIG. 7G-L). Large citrate-stabilized Au5 (17±5 nm), very polydisperse CTAB-stabilized Au6 (51±17 nm), and CTAB-stabilized nanorods Au7 (41±10 nm in length) are filtered off quantitatively (FIGS. 17, 18 and 19). Thus, the outcome of our filtration experiments did not depend on the capping layer of the filtered NPs but on particle size as demonstrated in Table 2:

TABLE 2

Filtration of various water-soluble AuNPs.

|  | Diameter (nm) | Capping layer | Filtration result |
| --- | --- | --- | --- |
| Au1 | 1.6 ± 0.6 | MPA | complete passing |
| Au2 | 2.8 ± 1.5 | MPA | separation |
| Au3 | 7.1 ± 5.9 | MPA | separation |
| Au4 | 17.5 ± 3.9 | MPA | complete removal |
| Au5 | 17.0 ± 5.0 | Citrate | complete removal |
| Au6 | 51 ± 17 | CTAB | complete removal |
| Au7 | 41 ± 10 (length) | CTAB | complete removal |
| Au8 | 5.3 ± 1.6 | PEG-SH | separation |

Separation of Quantum Dots (QDs).

2 ml of QD1+2 mixture was run over a supramolecular layer (0.65 mg Perylene V/cm$^2$) on a CA support (Advantec C045A025A, effective filtration area=3.7 cm$^2$, pore size=0.45 μm) in a PallEasy Pressure Syringe Filter Holder at a trans-membrane pressure of 1.2 bar. An aqueous solution of capping agent (adjusted to the pH 9 with NaOH) was used as the eluent and 5 fractions (2 ml) were collected.

As shown above, a thin supramolecular membrane (0.13 mg Perylene V/cm$^2$) allows filtration and separation of NPs with ~5 nm cutoff size. While, MPA-capped quantum dots QD1 (~4 nm) quickly pass the filter, it was observed that if a significantly thicker membrane is fabricated, QD1 permeate after a notable delay. Based on this observation we expected that particles of different sizes might pass the filter within different times, thus allowing for chromatographic size-selective separation of sub-5 nm NPs. Accessing this size range bears great potential, in particular for post-synthetic purification of quantum dots, as NPs size range between 2 and 5 nm is typical for widely utilized CdS, CdSe and CdTe particles.

Quantum dot luminescence is a function of particle size. In order to investigate size selective chromatography, a mixture of MPA-capped CdTe quantum dots QD1 (~4.0 nm) and smaller QD2 (~2.5 nm) was prepared, such that emissions of both particles had equal intensities (FIG. 8A). The mixture (2 ml) was run over a thick (~45 μm; 0.65 mg Perylene V/cm$^2$) supramolecular membrane (eluting with aqueous MPA solution (0.1 M)) and 5 fractions (2 ml) were collected successively. A gradual color change of fractions 1 (green) through 5 (orange) was observed (FIG. 8C). The emission spectrum of the first fraction corresponds mainly to QD2, while the last fraction contains predominantly QD1 (FIG. 8B, and intermediate fractions 2 to 4 contain mixtures of both particle types, with gradually rising QD1:QD2 ratio. However, the results indicate that it is possible to achieve considerable size-selective separation of sub-5 nm semiconductor nanoparticles over a 45 μm thick supramolecular membrane. As opposed to size exclusion chromatography, only minute amounts of (recyclable) stationary phase and small elution volumes are required to separate preparative amounts of nanoparticles. Notably, small particles pass the membrane faster than large particles, demonstrating different separation mechanism in the 3D fibrous network, as opposed to porous polymer beads used in size exclusion chromatography.

Example 12

Stability at Solutions with High Ionic Strength

Biological systems are commonly kept in solutions with higher ionic strength (i.e. in the presence of buffer, with ion concentrations similar to physiological conditions). The stability of the supramolecular membranes of this invention at these conditions was determined. The flow rates of solutions of different compositions and ionic strength were monitored. Changes and instabilities in the flow rate would indicate that the membranes are not stable under biologically relevant conditions.

Filtration of solutions of a) buffer solution at pH=7 (3-(N-morpholino)propanesulfonic acid, MOPS (20 mM), KCl (70 mM), $MgCl_2$ (10 mM)) and b) NaCl(aq) (150 mM) over the supramolecular membranes of Perylene V (Compound V) for 30 minutes took place at essentially identical flow rates, compared to filtration of neat double distilled water (FIG. 30).

Thus, the presence of higher salt concentrations does neither destabilize/dissolve the membrane, nor critically alter the membrane's nanoscopic structure, and the membrane can perform under conditions relevant to biological systems.

Example 13

Purification of Biological Macromolecules

In order to study applicability for purification or filtration of biological supramolecules, two proteins bovine serum albumin (BSA) and Kemp eliminase (KE70) were filtered through the Perylene V (Compound V) based membrane. BSA has a molecular weight of ~67 kDa, and dimensions of ~5×9×9 nm. KE70 has a molecular weight of ~30 kDa, and dimensions of ~5×4×4 nm. Considering the membranes' 5 nm cut-off, KE70 was expected to pass the supramolecular membrane, whereas BSA, being significantly larger than the membrane's pores, was expected to be retained.

A mixture of BSA (0.1 mg/ml) and KE70 (0.1 mg/ml) in 2 ml 3-(N-morpholino)propanesulfonic acid (MOPS) buffer solution at pH=7 was filtered over a freshly prepared supramolecular membrane (~12 μm thick). After the filtrate solutions had passed the membrane, additional 5.5 ml of neat MOPS buffer solution was run over the membrane. The filtrate was collected in fractions (5×1.5 ml). In order to obtain retained proteins, the used supramolecular membrane was scratched off its cellulose acetate support, dispersed in MOPS buffer solution, and centrifuged. The supernate contained the retained proteins, whilst the precipitage contained the membrane material Perylene V.

As indicated by SDS-PAGE (sodium dodecyl sulfate polyacrylamide gel electrophoresis), fractions 1 and 2 contain pure KE70, fraction 3 contains very small traces of KE70, and the following two fractions are void of any detectable protein concentrations (FIG. 31). In contrast, the retentate isolated from the membrane contains almost pure BSA. The findings were confirmed by the optical density (OD) measurements of the respective solutions at 280 nm (Table 3). The separation of the two proteins is in agreement with the membranes' 5 nm cut-off observed for metal and semiconductor nanoparticles.

TABLE 3

Optical densities (at 280 nm) of fractions 1-5, the initial protein solution (not filtered), and the proteins isolated from the membrane after the filtration experiment (retentate).

| Fraction Membrane wash | $OD_{280}$ reference |
|---|---|
| 1 | 0.224 |
| 2 | 0.219 |
| 3 | 0.00 |
| 4 | 0.00 |
| 5 | 0.00 |
| Not filtered (diluted proteins) | 0.137 |
| Retentate | 2.04 |

Example 14

Synthesis of Perylene VIII

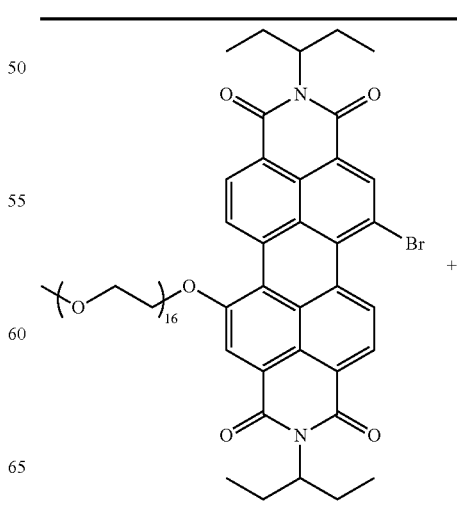

-continued

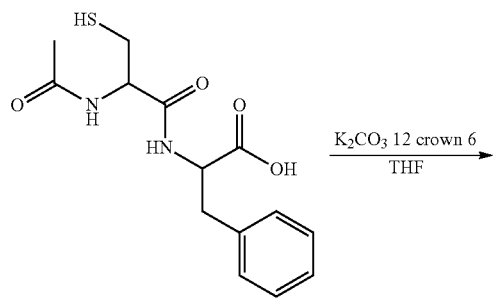 [SMILES: CC(=O)NC(CS)C(=O)NC(Cc1ccccc1)C(=O)O ; "THF"]

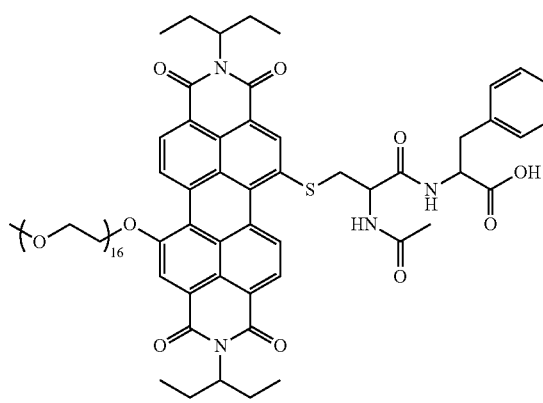

| Perylene VIII | gr/mol | gr | mol |
|---|---|---|---|
| mono bromo mono peg | 1388 | 0.024 | 1.73E−05 |
| K₂CO₃ | 138.2 | 9.56E−03 | 6.92E−05 |
| Crown 18C6 | 264.3 | 9.14E−03 | 3.46E−05 |
| Ac-Cys-Phe | 310 | 6.43E−03 | 2.07E−05 |

All the reactants were mixed in a vial under inert gas (inside the nitrogen field glove-box) box and dissolved in dry THF. The reaction mixture was stirred for 20 hr over which it changed color from translucent pink to opaque purple. The THF was removed by evaporation and the remaining solid was dissolved in DCM (dichloromethane) and a prep TLC (thin layer chromatography) was performed in the box, in a 10% MeOH in DCM solution. The product was extracted from the silica using a 1/1 DCM MeOH solution. The product was dried and dissolved in slightly basic water. The product was transferred to a separating funnel and the aqueous phase was washed with DCM. Then the aqueous phase was acidified to pH 2 using 0.1 M HCl and extracted to DCM. The organic phase was washed 3 times with KCl brine. This process was preformed twice in order to get rid of the crown ether. The extract was concentrated and precipitated from hexane and from diethyl-ether, the precipitant was filtered and re-dissolved in DCM.

Example 15

Synthesis of Perylene XIII

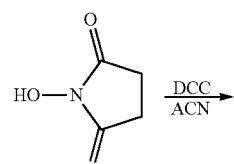

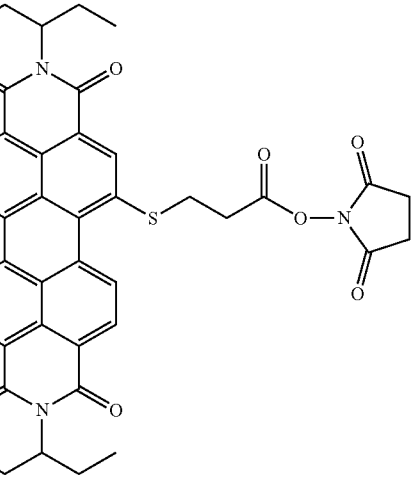

| Perylene XIII | gr/mol | gr | mol | ml | mol/L | gr/ml |
|---|---|---|---|---|---|---|
| PDI-MPA | 6.35E+02 | 8.00E−03 | 1.26E−05 | | | |
| Trp | 2.04E+02 | 5.15E−03 | 2.52E−05 | | | |
| DCC | | | 1.26E−05 | 1.26E−02 | 1.00E+00 | |
| NHS | 1.15E+02 | 2.90E−03 | 2.52E−05 | | | |
| NaHCO3 | 8.40E+01 | 1.06E−03 | 1.26E−05 | | | |

The first step included preparation of the NHS (N-hydroxysuccinimide) activated ester using DCC coupling. In a vile 8 mg PDI-MPA (PDI-3-mercaptopropionic acid) (1.26E-05 mol) were dissolved in 5 ml acetonitrile. 2.9 mg NHS (2.52E-05 mol 1:2 ratio) were added to the PDI (perylene diimide)

solution. 12.6 µl DCC 1N solution in NMP were added. The reaction was left to stir for 4 hr and was monitored by TLC. When no more change was detected the second part of the reaction was preformed.

In the second stage the ester was reacted with Tryptophan.

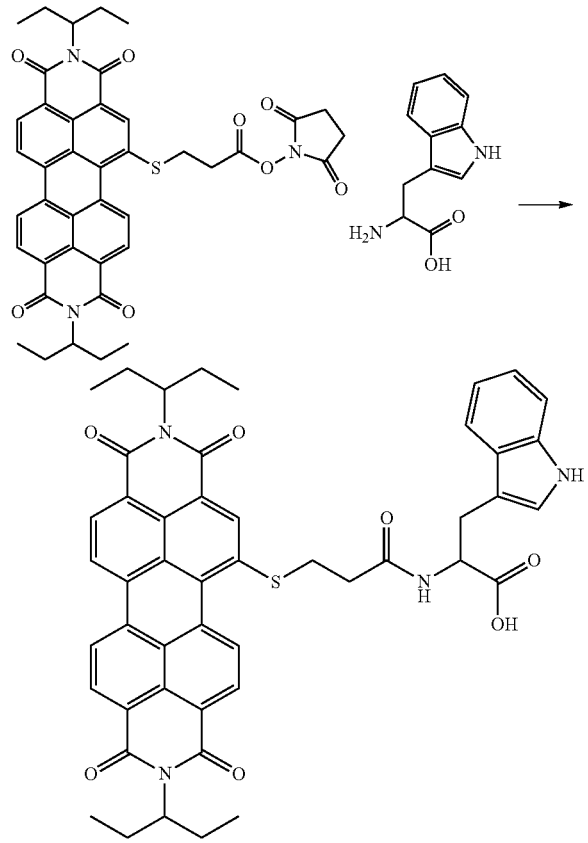

5.15 mg Trp were dissolved in a minimal amount of water by addition of a molar amount of NaCO$_3$ and sonication. The Trp solution was added to the PDI-NMP-NHS solution and was stirred over night. The compound was transferred to a separating funnel and the aqueous phase was washed with DCM. Then the aqueous phase was acidified to pH 2 using 0.1 M HCl and extracted to DCM. The organic phase was washed 3 times with KCl brine. The extract was concentrated and precipitated from hexane and from diethyl-ether, the precipitant was filtered and re-dissolved in DCM. NMR and mass were measured.

Example 16

Separation of Proteins Using the Membrane of this Invention

Methods

Fabrication of Supramolecular Membranes.

Perylene diimide supramolecular aqueous solution (0.5 mM, 1 ml) was diluted in water (2 ml) and the mixture was filtered over a syringe filter (WhatmanPuradisc FP 30, CA; effective filtration area: 5.7 cm$^2$; pore size: 0.45 µm). During filtration, perylene diimide (PDI) was deposited on the CA support, as seen by the color change from dark purple feed solution to colorless filtrate, and formation of a dark purple layer on the CA support. The transmembrane pressure was created by opening the gauge to a pressurized nitrogen gas cylinder. It was slowly increased to 0.8 bar during deposition of PDI. Care was taken to avoid air bubbles in the filter chamber, which would hamper the formation of a continuous supramolecular layer. Subsequently, water (2 ml) was filtered through the membrane. In order to adjust pH and ionic strength in the filter chamber to the pH and ionic strength of the protein solution that was to be filtered, neat buffer solution (3 ml) was run through the membrane. The filtrate of that buffer (F0, 1.5 ml) was collected as a reference for UV/Vis spectroscopy. The filter housing was kept filled with buffer solution and the supramolecular membrane was used directly for filtration experiments.

Filtration Experiments.

The protein mixture (1.5 ml) was filtered over a freshly prepared supramolecular membrane at a constant transmembrane pressure of 0.8 bar. Then, 6 ml of protein-free MOPS buffer solution was filtered in order to rinse out residual proteins from membrane and filter housing. Fractions were collected (5×1.5 ml, F1-F5). The fractions were analyzed by UV/Vis and SDS-PAGE.

Results

A mixture of six purified proteins was used to carry out filtration experiments using the membrane of this invention. The mixture included: (1) N-terminal domain of EIIBCA-Bgl residues 2-84(EIIBCA); (2) In silico designed Kemp eliminase (KE70); (3) L-carnitinedehydratase (LCD); (4) L-Fuculose-1-Phosphate Aldolase (Aldolase); (5) Citrate Synthase (CS) and (6) Bovine Serum Albumin (BSA).

This protein mixture presents a broad range of masses, making it suitable for characterization of the filtration cutoff. The proteins were dissolved in MOPS buffer solution (MOPS, 20 mM; KCl, 70 mM; MgCl$_2$, 10 mM; pH=7.0) with an overall protein concentration of 1.8 mg/ml (0.3 mg/ml for each protein). In order to evaluate the actual size of the individual proteins in solution, they were each analyzed by gel filtration chromatography (GFC) and their hydrodynamic diameters (D$_h$) were determined using dynamic light scattering (DLS). Not all proteins in the mixture were monomeric; CS exhibited a molecular weight of approximately 288 kDa (from GFC), corresponding to its well-known hexameric form (301 kDa), Aldolase was a tetramer, and the commercially obtained BSA was oligomeric (400 kDa, determined by GFC). These findings are consistent with DLS measurements, showing a size increase in the order EIIBCA<KE70<LCD<Aldolase<CS<BSA (Table 4).

TABLE 4

Size-related values of the proteins: Calculated molecular weight (MW), hydrodynamic diameter (D$_h$), and molecular dimensions estimated from X-ray structures.

| Protein | MW [kDa] | D$_h$ [nm] | Protein X-ray structure dimensions (PDB code) [nm] |
|---|---|---|---|
| EIIBCA | 8.7 | 3.4 | n.a. |
| KE70 | 29 | 5.4 | 5.0 × 4.1 × 3.8(3Q2D) |
| LCD | 92 | 7.2 | n.a. |
| Aldolase | 158 | 8.2 | 7.0 × 7.0 × 5.5(1DZU) |
| CS (hex.) | 301 | 11.4 | 13.1 × 12.3 × 8.2 (homologous to 1NXG) |
| BSA (olig.)$^a$ | ≥400 | 12.8, 57.8 | n.a. |

$^a$BSA had a bimodal size distribution.

Filtration experiments were performed employing a flow of the protein mixture (1.5 ml) in aqueous MOPS buffer solution through a freshly prepared supramolecular membrane at 0.8 bar transmembrane pressure. After the feed solution had passed the membrane, additional clean buffer solution (6 ml) was filtered to rinse out remaining proteins from the membrane. The filtrate was collected in fractions (5×1.5 ml, F1-F5) and UV/Vis spectra were recorded (FIG. 33). Relative protein concentrations for the collected fractions were quantified via absorbance at 280 nm. The fractions did not exhibit any absorption feature in the visible spectrum, showing that no detectable amount of Perylene V ($\lambda_{max,1}$=393 nm, $\lambda_{max,2}$=538 nm) was leaching out of the membrane during filtration. The first two filtrate fractions (F1 and F2) contained considerable amounts of protein; F3 contained only minor amounts, whereas F4 and F5 were virtually protein-free (FIG. 33C). Altogether, 38±4% of the proteins passed the membrane. In a control experiment, the protein mixture was also passed through the pristine CA membrane without the Perylene V layer. As confirmed by UV/Vis spectra of the filtrate, the CA membrane itself did not retain any proteins (FIG. 33A), showing that the retention is due to the supramolecular membrane only and not caused by adsorption on the support.

Proteins that were retained on the supramolecular membrane could be partially recycled by dispersing the used membrane in buffer solution (using a vortex mixer), followed by removing the Perylene V supramolecular material via centrifugation. The resulting supernatant contained retained proteins while the pellet contained Perylene V together with some proteins that could not be retrieved. The filtration experiment results were analyzed by sodium dodecyl sulfate polyacrylamide gel electrophoresis (SDS-PAGE) (FIG. 34A). Individual protein concentrations in filtrate and retentate were estimated densitometrically from the gel. Filtration experiments were repeated five times using independently deposited membranes, which showed consistent separation performance.

FIG. 34C shows the retention (the percentage of proteins filtered from the solution) as a function of the molecular weight. The retained particles in the Perylene V membrane are captured in the interior of the membrane rather than on the surface (depth filtration). The retention of proteins is clearly size-dependent and follows a typical sigmoid curve, indicating that size-selective capture (e.g. through mechanical sieving) plays a major role in the filtration process, rather than specific (e.g. electrostatic) protein adsorption. However, adsorption, which often takes place in depth filters, might play a minor role, for instance in the retention of small amounts (~10%) of EIIBCA. The molecular weight cutoff, defined as the theoretical weight of a molecule with 90% retention, was determined from the retention curve (FIG. 34C), as 150 kDa. In terms of hydrodynamic diameter, the membrane cutoff is 8 nm (FIG. 34D).

FIG. 34B presents the concentration of the proteins in each of the filtrate fractions and that of the retained proteins recycled from the membrane. Notably, permeation of the three smaller proteins EIIBCA, KE70, and LCD, showed a size-dependent trend: The smallest (EIIBCA) passed the membrane with a shorttime delay and was completely collected in F1 and F2, whereas the larger (KE70) exhibited a longer delay, and small amounts were detected in F3 as well. Finally, the largest of these three (LCD) was found in considerable amounts in F3, and its traces were detected in F4.

Example 17

Recycling of Proteins and Perylene V

After the filtration experiment, as described in Example 16, the filter chamber was opened and the Perylene V supramolecular layer was scratched off the cellulose acetate (CA) support and suspended in MOPS buffer solution (1.5 ml). It was vortexed for 1 h in order to disentangle the Perylene V supramolecular fibers, thus releasing retained proteins (R). In order to separate Perylene V from the retained proteins, the solution was centrifuged for 15 minutes at 20800 g (using a desktop centrifuge). The supernatant contained retained proteins while the pellet (P) contained Perylene V together with some retained proteins that could not be extracted. Both supernatant and pellet were analyzed separately by SDS-PAGE, whereby the pellet was highly concentrated due to its small volume. In order to purify Perylene V in the pellet from residual proteins and other organic and inorganic contaminations, ten such pellets were dissolved in 20 ml of a water/ethanol mixture (2:3, v/v). Subsequently, Perylene V was extracted with dichloromethane (40 ml). The colorless aqueous phase was discarded. The organic phase was dried in high vacuum. The solid was washed with hexane (3×50 ml), and with water (1×50 ml). Subsequently, it was purified by silica column chromatography, eluting successively with: 1) 200 ml $CHCl_3$, 2) 200 ml $CHCl_3$/MeOH (98:2, v/v), 3) 200 ml $CHCl_3$/MeOH (92:8, v/v). The product contained pure Perylene V, as revealed by $^1$H-NMR. Nearly quantitative recycling was achieved.

For the retained proteins, about 66% of CS was regained from the filter, whereas only 25% of retained Aldolase could be recycled, possibly due to aggregation or irreversible entrapment within the supramolecular fibers of the membrane material.

The membrane itself can be disassembled in water/ethanol (2:3, v/v), cleaned from contaminations via chromatography over a short silica column, re-assembled, and re-used. Importantly, the membranes prepared from recycled Perylene V had similar thickness and identical separation performance, as compared to the membranes prepared from non-recycled Perylene V (FIG. 35).

Facile recycling and reproducible separation performance after recycling can be regarded as a direct result of the non-covalent nature of the membrane material: its nanoscopic structure (i.e. the three dimensional network of supramolecular fibers) is encoded at the molecular level, allowing simple self-assembly and deposition procedures.

Example 18

Monomer/Aggregate Separation

In order to demonstrate monomer/aggregate separation, oligomeric BSA was mixed with specially prepared monomeric BSA and the mixture was filtered over the Perylene V supramolecular membrane. Due to their small size, the protein oligomers ($D_h$~12.8 nm) cannot be removed by a standard desktop centrifuge (20800 g). However, as revealed by GFC, the supramolecular membrane efficiently removed oligomeric BSA from the mixture, resulting in a filtrate of pure BSA monomer (FIG. 36).

Example 19

Activity of the Filtered and Recycled Proteins

Activity of Filtered KE70

A solution of KE70 (4 ml, 0.3 mg/ml) in HEPES buffer was filtered over a freshly prepared supramolecular membrane. Due to some dilution in the filter chamber, the filtrate contained KE70 at 89.6% of its original concentration, based on absorbance at 280 nm (Table 5)

TABLE 5

Absorbance at 280 nm ($OD_{280}$) for quantification of the relative enzyme concentrations, line slope of the linear range of the kinetics plot ($\Delta OD_{380}/\Delta t$), relative KE70 concentration and activity.

|  | $OD_{280}$ | $\Delta OD_{380}/\Delta t$ [$\min^{-1}$] | Relative Conc. [%] | Relative activity [%] |
|---|---|---|---|---|
| Before filtration | 0.1123 | 0.2704 | 100 | 100 |
| Filtrate | 0.1007 | 0.2391 | 89.6 | 88.1 |
| Buffer only | 0.0003 | 0.0080 | 0 | 0. |

The quantification of KE70 activity in the solution before filtration, in the filtrate, and in neat buffer solution (background reaction) was performed at 25° C. by measuring the kinetics of the enzyme-catalyzed isomerisation of 5-Nitrobezisoxazole via absorbance of the product at 380 nm ($OD_{380}$). For this, 15 μl of the test solution was diluted in 1.5 ml HEPES buffer in a UV/Vis cuvette, and $OD_{380}$ was recorded for several minutes. Then the reaction was started by addition of 1 μl 5-Nitrobezisoxazole from stock solution in acetonitrile (67 μM after dilution) and the kinetics measurement was continued for 10-15 minutes (FIG. 37A). The slope of $OD_{380}$ ($\Delta OD_{380}/\Delta t$) in the linear region of the kinetics plot (FIG. 37B) is proportional to the enzymatic activity under saturation condition. Thus, activity of the filtrate was determined to be 88.1% with respect to the original solution, whilst the concentration determined from OD at 280 nm was 89.6%. Therefore, taking into consideration dilution, the activity of filtered KE70 is ≥98%.

Activity of Recycled CS

In addition to KE70, the enzymatic activity of hexameric CS was tested after filtration. In contrast to KE70, CS was completely retained and recycled from the membrane. In case of retained enzymes, their structure and function might be affected by the extensive contact with the supramolecular material, and by the subsequent recycling procedure. CS activity before filtration and after recycling from the membrane was quantified at 25° C. according to an activity assay: measuring the kinetics of Citrate formation from Oxaloacetate and Acetyl Coenzyme A (Acetyl-CoA) by detecting the indicator of the reaction, 2-nitro-5-thiobenzoate (TNB) at 412 nm ($OD_{412}$).

CS (0.3 mg/ml) in HEPES buffer solution (1.5 ml) was filtered over a freshly prepared supramolecular membrane, followed by 6 ml neat buffer solution. The enzyme was recycled according to the regular procedure (see Example 17). Quantification of the protein concentration of recycled enzyme and of the enzyme solution before filtration was performed via Bradford test (Table 6). (Bradford et al. *Anal. Biochem.* 1976, 72, 248-254)

TABLE 6

Quantification of CS via Bradford test.

| | $OD_{600}$ | Conc. [mg/ml] | Relative Conc. [%] |
| --- | --- | --- | --- |
| Before filtration | — | 0.30 | 100 |
| Before filtration (10× diluted) | 0.38 | 0.030 | |
| Recycled | — | 0.079 | 26 |
| Recycled (5× diluted) | 0.20 | 0.016 | |

The activity of CS before and after filtration was quantified at 25° C. according to an activity assay. In a UV/Vis cuvette, 143 μl of the enzyme-containing solution was diluted with HEPES buffers to a total volume of 1.43 ml. Then the following reagents were added successively: 6.0 μl of Ethylenediaminetetraacetic acid (EDTA; 500 mM; final concentration: 2 mM) in water, 15 μl of 5,5'-Dithiobis(2-nitrobenzoate) (DTNB; 10 mM; final concentration: 0.1 mM) in ethanol, and 15 μl of Acetyl Coenzyme A (Acetyl-CoA; 14 mM; final concentration: 0.14 mM) in HEPES buffer. Absorbance at 412 nm ($OD_{412}$) was recorded for a few minutes. Then 30 μl of Oxaloacetate (10 mM; final concentration: 0.2 mM) in HEPES buffer was added and $OD_{412}$ was recorded for another 4-5 minutes (FIG. 38A). The slope of $OD_{412}$ ($\Delta OD_{412}/\Delta t$) in the linear region of the kinetics plot (FIG. 38B) is proportional to the enzymatic activity under saturation condition. Thus, activity of the recycled enzymes was determined to be 29% with respect to the original solution (Table 7). This value is in good agreement with the concentration determined from Bradford test (26%), showing that enzymatic activity is conserved during the filtration and recycling process.

TABLE 8

Slope of the linear fits ($\Delta OD_{412}/\Delta t$) in the initial CS activity kinetics, and calculated relative activity.

| | $\Delta OD_{412}/\Delta t$ [min$^{-1}$] | Relative activity [%] |
| --- | --- | --- |
| Before filtration | 0.6749 | 100 |
| Recycled | 0.1974 | 29 |
| Buffer only | 0.0004 | 0 |

Example 20

Biocatalytic Activity of Immobilized Proteins on the Membrane

Filtration of large enzymes results in their immobilization within the supramolecular network, keeping them exposed to the flux of solvent and solutes. Such an array (membrane/immobilized enzyme) may represent a versatile system to carry out biocatalytic reactions in a heterogeneous manner.

β-Galactosidase Activity

The enzymatic activity of membrane-immobilized β-Galactosidase (β-Gal, 465 kDa) was analyzed. β-Gal is significantly larger than the membrane cutoff, resulting in near-quantitative retention. It is ubiquitous in nature and widely utilized in molecular biology, catalyzing the hydrolysis of the glycosidic bond of β-Galactopyranosides. β-Gal and many other hydrolases do not require presence of coenzymes, making them the most relevant enzyme class for biotechnological applications in industry, e.g., β-Gal has wide application in the dairy industry for the production of low-lactose milk.

For immobilization, 1.5 ml of β-Gal (0.2 mg/ml) was filtered over a freshly prepared supramolecular membrane, and rinsed with 7.5 ml of clean buffer solution. Once the enzyme was retained on the membrane, the solution flux slightly dropped from 20 L h$^{-1}$ m$^{-2}$ to 17 L h$^{-1}$ m$^2$. Subsequently, a typical activity assay solution containing the substrate o-nitrophenyl β-D-galactopyranoside (ONPG, 0.05 mg/ml) was passed through the membrane. As the colorless ONPG feed solution passed through the membrane it turned yellow, indicating the β-Gal-catalyzed conversion of ONPG into o-Nitrophenol (ONP, $\lambda_{max}$=420 nm) (FIG. 39A). In order to quantify the conversion and to study performance under constant substrate flux for prolonged periods of time, the filter was connected to a UV/Vis flow cuvette, and the absorbance of the filtrate at 420 nm was recorded. Importantly, the reaction showed stable conversion over several hours of uninterrupted substrate flow with an average yield of ~90% ONP (FIG. 39B).

Small amounts of enzyme were observed to leach out of the membrane over time, as expected in immobilization that does not involve covalent attachment of the enzyme to the support. However, enzyme leaching was very low (decreasing from 0.24% to 0.046% activity with respect to the original enzyme solution; and did not influence the overall reaction yield. Emphasizing its remarkable robustness and biocompatibility, the supramolecular membrane/embedded enzyme array sustained stable operation under a constant flux of solution for overall 6 hours (incl. preparation, rinsing steps, and test of enzyme leaching), out of which 3 hours were dedicated to biocatalytic substrate conversion.

Hexameric CS Activity

In an additional experiment, hexameric CS was immobilized and tested for its biocatalytic activity. While β-Gal facilitates the degradation of a complex molecule (ONPG)

into smaller parts (Galactose, ONP), CS represents a distinctly different case: a simple precursor (Oxaloacetate) is converted into a more complex product (Citrate), requiring the presence of a coenzyme (Acetyl-CoA). CS immobilization was performed by simply filtering 2 ml enzyme solution (0.3 mg/ml) over a freshly prepared supramolecular membrane, followed by rinsing with 10.5 ml clean buffer solution. The activity of immobilized CS was determined using an assay solution (Srere, P. A.; Brazil, H.; Gonen, L., *Acta Chem. Scand.* 1963, 17, S129-S134). When running the mixed solution of Oxaloacetate, Acetyl-CoA, and 5,5'-Dithiobis(2-nitrobenzoate) (DTNB) through the membrane, biocatalytic formation of Citrate was indicated by the yellow color of the filtrate, which resulted from the subsequent reaction between HS-CoA and DTNB, forming TNB ($\lambda_{max}$=412 nm) (FIG. 40). Thus, conversion of Oxaloacetate into Citrate under constant flow of substrate and coenzyme was readily achieved. Similar to β-Gal, leaching of CS was low (~0.23% activity with respect to the original enzyme solution).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. Noncovalent self-assembled porous membrane comprising a perylene diimide supramolecular structure; providing a chromatography medium for size-selective separation of nano-material; wherein said perylene diimide supramolecular structure comprises a perylene, a salt thereof or metal complex thereof as a monomeric unit represented by the structure of formula I:

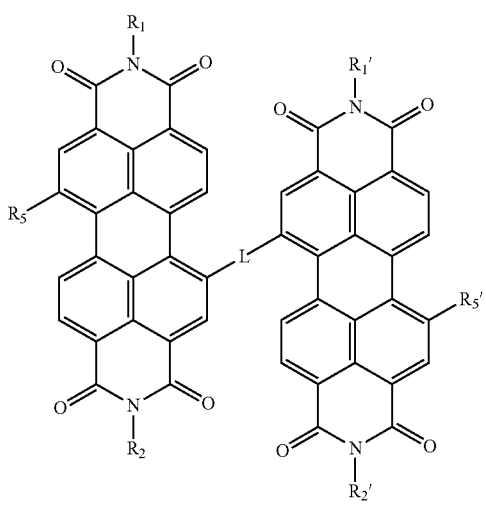

(I)

wherein $R_1$ and $R_1'$ are independently $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)NHR_3NH]_pH$ wherein said aryl or heteroaryl groups are optionally substituted by 1-3 groups selected from halide, CN, $CO_2H$, OH, SH, $NH_2$, $CO_2$—($C_1-C_6$ alkyl), and O—($C_1-C_6$ alkyl); wherein A comprises three same or different of the following substituents Cl, Br, I, O($C_1-C_8$)alkyl or ($C_1-C_8$)alkyl; and wherein $R_3$ in said $[C(O)NHR_3NH]_pH$ is an alkyl, haloalkyl, hydroxyalkyl, hydroxyl, aryl, phenyl, alkylphenyl, alkylamino and independently the same or different when p is larger than 1;

$R_2$ and $R_2'$ are independently $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)NHR_4NH]_sH$ wherein said aryl or heteroaryl groups are optionally substituted by 1-3 groups selected from halide, CN, $CO_2H$, OH, SH, $NH_2$, $CO_2$—($C_1-C_6$ alkyl), and O—($C_1-C_6$ alkyl); wherein A comprises three same or different of the following substituents Cl, Br, I, O($C_1-C_8$)alkyl or ($C_1-C_8$)alkyl; and wherein $R_4$ in said $[C(O)CHR_4NH]_sH$ is an alkyl, haloalkyl, hydroxyalkyl, hydroxyl, aryl, phenyl, alkylphenyl, alkylamino and independently the same or different when s is larger than 1;

$R_5$ and $R_5'$ are independently H, —$OR_x$ where $R_x$ is $C_1-C_6$ alkyl or $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, aryl, heteroaryl, $C\equiv C-R_7$, $CH=CR_8R_9$, $NR_{10}R_{11}$, amino acid, peptide or a saturated carbocyclic or heterocyclic ring wherein said saturated heterocyclic ring or heteroaryl contains at least one nitrogen atom and $R_5$ or $R_5'$ are connected via the nitrogen atom and wherein said saturated carbocyclic ring, heterocyclic ring, aryl and heteroaryl groups are optionally substituted by 1-3 groups selected from halide, aryl, heteroaryl, CN, $CO_2H$, OH, SH, $NH_2$, $CO_2$—($C_1-C_6$ alkyl), and O—($C_1-C_6$ alkyl);

$R_7$ is H, halo, $(C_1-C_{32})$alkyl, aryl, $NH_2$, alkyl-amino, COOH, C(O)H, alkyl-COOH heteroaryl, $Si(H)_3$ or $Si[(C_1-C_8)$alkyl$]_3$ wherein said aryl or heteroaryl groups are optionally substituted by 1-3 groups selected from halide, aryl, heteroaryl, CN, $CO_2H$, OH, SH, $NH_2$, $CO_2$—($C_1-C_6$ alkyl), and O—($C_1-C_6$ alkyl);

$R_8$, $R_9$, $R_{10}$ and $R_{11}$ are independently H, $(C_1-C_{32})$alkyl, aryl, $NH_2$, alkyl-amino, COOH, C(O)H, alkyl-COOH or heteroaryl wherein said aryl or heteroaryl groups are optionally substituted by 1-3 groups selected from halide, CN, $CO_2H$, OH, SH, $NH_2$, $CO_2$—($C_1-C_6$ alkyl), and O—($C_1-C_6$ alkyl);

L is a linker;

n is an integer from 1-5;

o is an integer from 1-100;

p is an integer from 1-100;

q is an integer from 1-5;

r is an integer from 1-100; and s is an integer from 1-100;

wherein if $R_5$ and $R_5'$ independently are amino acid or peptide; said membrane will form a chiral membrane.

2. The membrane of claim 1, wherein said perylene supramolecular structure comprises a perylene represented by the structure of formula III, IV or V:

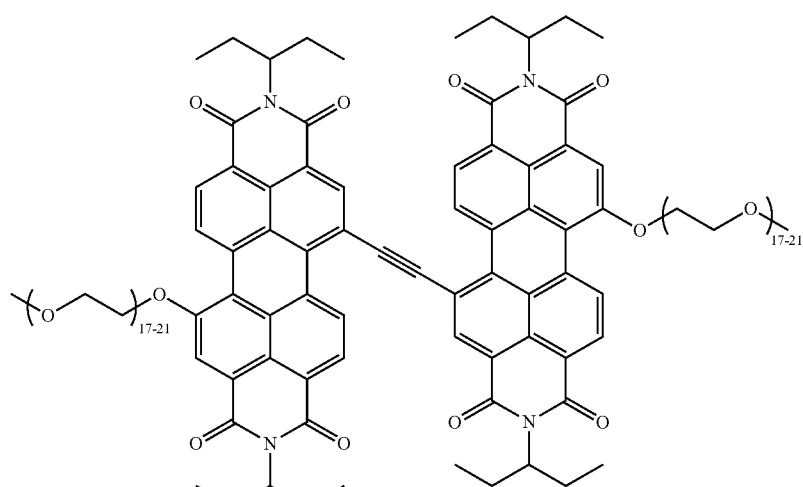
Perylene III
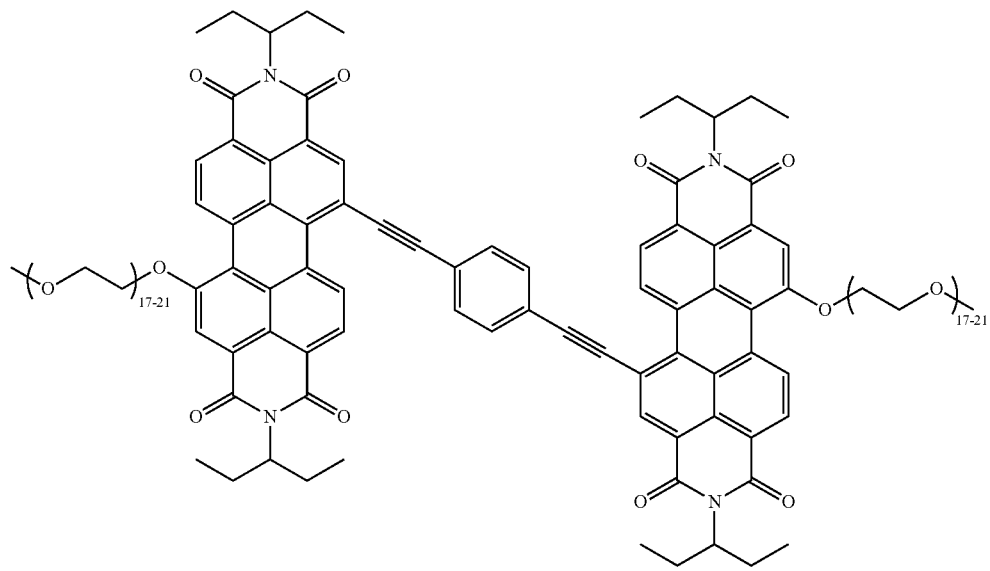
Perylene IV
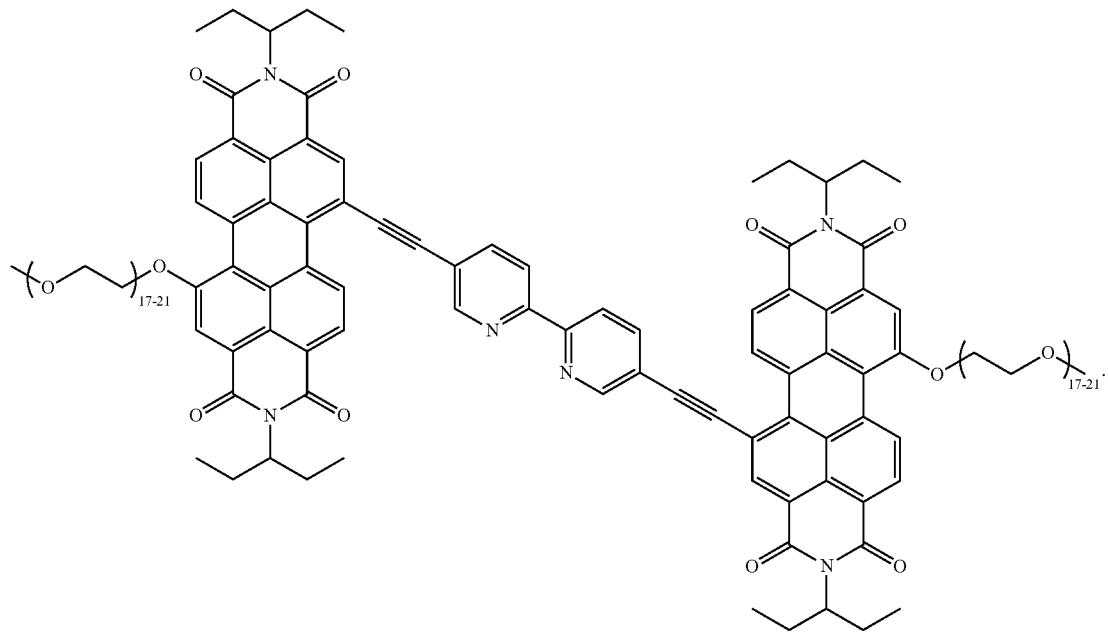
Perylene V

3. The porous membrane of claim 1, wherein the size of the pores in said porous membrane depends on the thickness of said pore membrane wherein said size of the pores in said porous membrane has a cutoff size of between 2-100 nm.

4. The porous membrane of claim 1, wherein said nanomaterials are nanoparticles or biomolecules.

5. The porous membrane of claim 1, wherein the size of the pores depends on the thickness of the porous membrane, wherein the thickness of said porous membrane is between 5-100 µm.

6. A method of separation, filtration or purification of nanomaterials comprising (a) transferring an aqueous solution or emulsion comprising a perylene supramolecular structure through porous solid support, thereby forming a noncovalent self-assembly perylene based membrane on said porous solid support; (b) transferring a solution of nano-materials through said noncovalent self-assembled perylene based membrane of step (a); wherein the particles size which are larger than the pores of said membrane remain on said membrane; wherein said noncovalent self-assembled perylene diimide comprises a perylene, a salt thereof or a metal thereof as a monomeric unit represented by the structure of formula I:

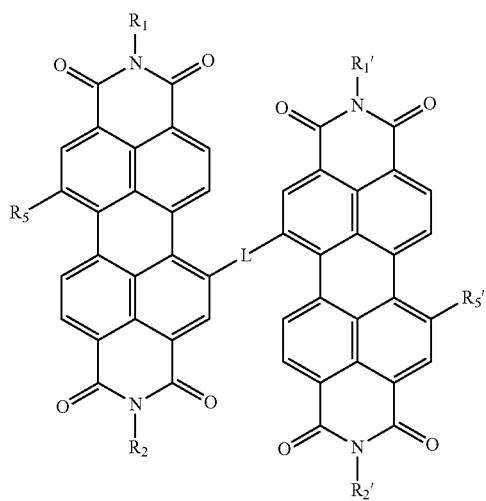

I wherein $R_1$ and $R_1'$ are independently $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)NHR_3NH]_pH$ wherein said aryl or heteroaryl groups are optionally substituted by 1-3 groups selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, $O(C_1-C_8)$alkyl or $(C_1-C_8)$alkyl; and wherein $R_3$ in said $[C(O)NHR_3NH]_pH$ is an alkyl, haloalkyl, hydroxyalkyl, hydroxyl, aryl, phenyl, alkylphenyl, alkylamino and independently the same or different when p is larger than 1;

$R_2$ and $R_2'$ are independently $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)NHR_4NH]_sH$ wherein said aryl or heteroaryl groups are optionally substituted by 1-3 groups selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)NHR_4NH]_sH$ is an alkyl, haloalkyl, hydroxyalkyl, hydroxyl, aryl, phenyl, alkylphenyl, alkylamino and independently the same or different when s is larger than 1;

$R_5$ and $R_5'$ are independently H, —$OR_x$ where $R_x$ is $C_1-C_6$ alkyl or $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, aryl, heteroaryl, C≡C—$R_7$, CH=$CR_8R_9$, $NR_{10}R_{11}$, amino acid, peptide or a saturated carbocyclic or heterocyclic ring wherein said saturated heterocyclic ring or heteroaryl contains at least one nitrogen atom and $R_5$ or $R_5'$ are connected via the nitrogen atom and wherein said saturated carbocyclic ring, heterocyclic ring, aryl and heteroaryl groups are optionally substituted by 1-3 groups selected from halide, aryl, heteroaryl, CN, $CO_2H$, OH, SH, $NH_2$, $CO_2$—$(C_1-C_6$ alkyl), and O—$(C_1-C_6$ alkyl);

$R_7$ is H, halo, $(C_1-C_{32})$alkyl, aryl, $NH_2$, alkyl-amino, COOH, C(O)H, alkyl-COOH heteroaryl, $Si(H)_3$ or $Si[(C_1-C_8)alkyl]_3$ wherein said aryl or heteroaryl groups are optionally substituted by 1-3 groups selected from halide, aryl, heteroaryl, CN, $CO_2H$, OH, SH, $NH_2$, $CO_2$—$(C_1-C_6$ alkyl), and O—$(C_1-C_6$ alkyl);

$R_8$, $R_9$, $R_{10}$ and $R_{11}$ are independently H, $(C_1-C_{32})$alkyl, aryl, $NH_2$, alkyl-amino, COOH, C(O)H, alkyl-COOH or heteroaryl wherein said aryl or heteroaryl groups are optionally substituted by 1-3 groups selected from halide, CN, $CO_2H$, OH, SH, $NH_2$, $CO_2$—$(C_1-C_6$ alkyl), and O—$(C_1-C_6$ alkyl);

L is a linker;
n is an integer from 1-5;
o is an integer from 1-100;
p is an integer from 1-100;
q is an integer from 1-5;
r is an integer from 1-100; and
s is an integer from 1-100;

wherein if $R_5$ and $R_5'$ independently are amino acid or peptide; said membrane will form a chiral membrane.

7. The method of claim 6, wherein said noncovalent self-assembled perylene comprises a perylene represented by the structure of formula III, IV or V:

Perylene III
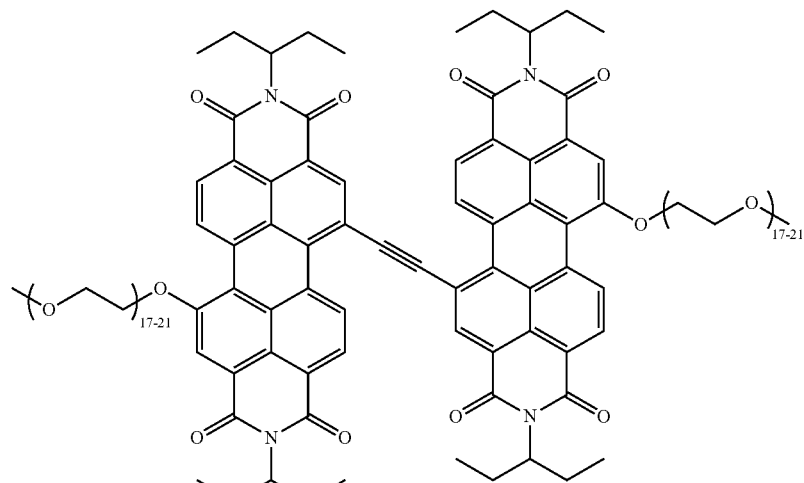
Perylene IV
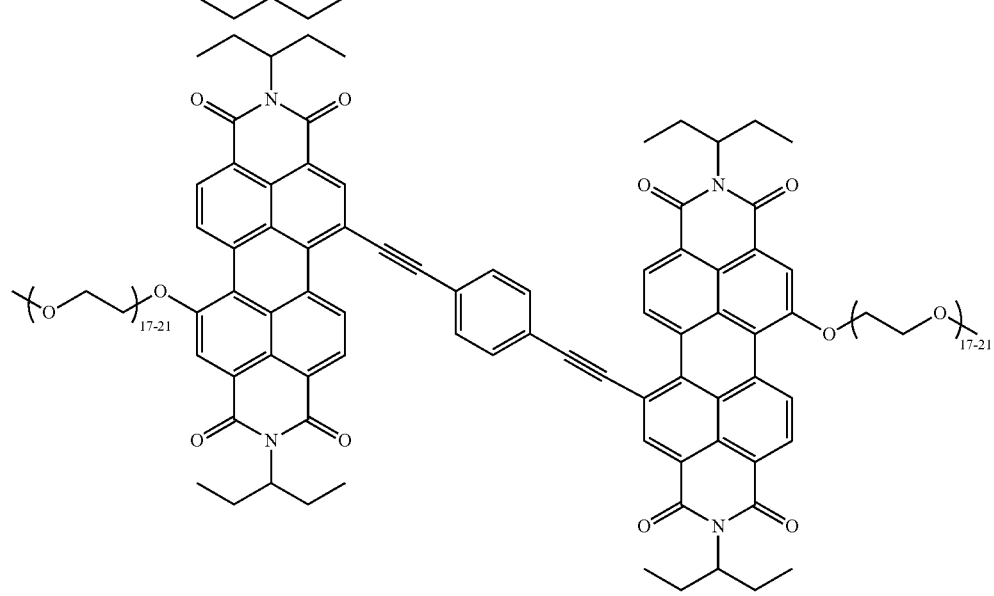
Perylene V
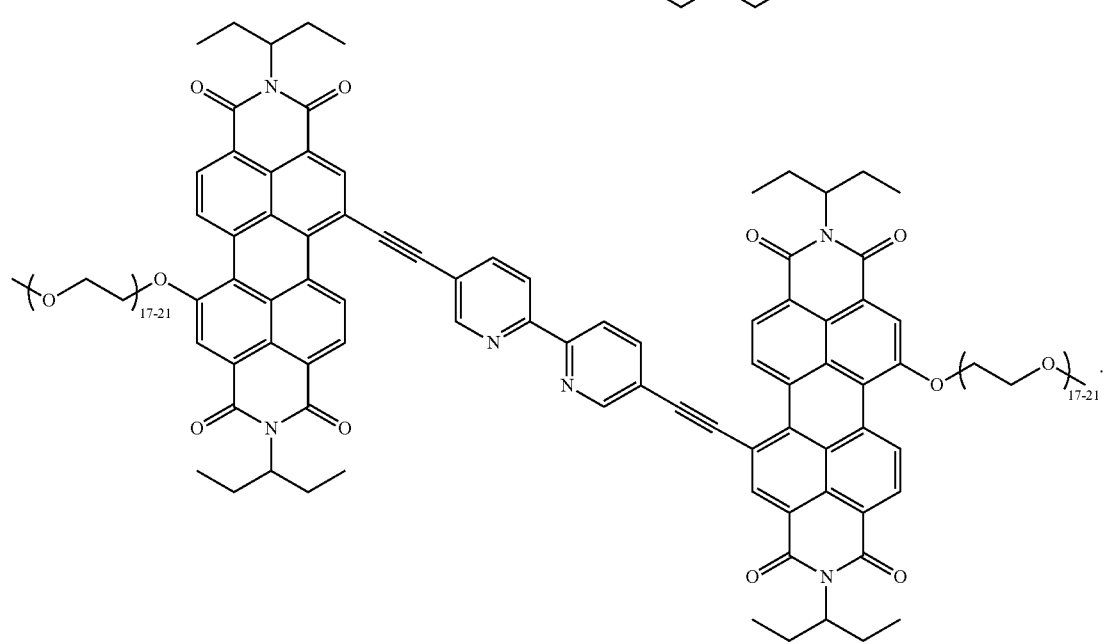

8. The method of claim 6, wherein said nano-materials are nanoparticles or biomolecules.

9. The method of claim 6, wherein the size of the pores in said porous membrane depends on the thickness of said porous membrane wherein said size of the pores in said membrane has a cutoff size of between 2-100 nm and said thickness of said porous membrane is from 5 μm to about 100 μm.

10. The method of claim 6, wherein said solid support is a microfiltration filter comprising cellulose acetate (CA), teflon (PTFE) or polycarbonate.

11. The method of claim 10, wherein said microfiltration filter has a pore size larger than 5 nm.

12. The method of claim 8, wherein said nanoparticles are metal nanoparticles, nanoparticles solubilized in water, quantum dots, CdS, CdSe or CdTe and said biomolecules are peptides, DNA, RNA, proteins and viruses.

13. The method of claim 6, wherein said noncovalent self-assembly perylene based membrane is recycled comprising; (a) washing said microfiltration filter with said membrane and the retenate with a mixture of alcohol and water; (b) extracting said perylene structure with an organic solvent; and (c) isolating said perylene structure which can be further used to form a noncovalent self-assembled perylene based membrane in aqueous conditions.

14. The method of claim 13, wherein said ratio of said water and alcohol mixture is between about 5:5 to 3:7 v/v.

15. The method of claim 13, wherein said organic solvent comprises methylene chloride, chloroform or ethyl acetate.

16. The method of claim 13, wherein the retenate on said membrane are isolated comprising (a) washing said microfiltration filter with said membrane and said retenate with a mixture of alcohol and water; (b) extraction of said perylene structure with an organic solvent, and said retenate remain in the aqueous phase.

17. The method of claim 16, wherein the ratio between said water and alcohol mixture is between about 5:5 to 3:7 v/v.

18. The method of claim 16, wherein said organic solvent comprises methylene chloride, chloroform or ethyl acetate.

19. A method of preparing a noncovalent self-assembled porous perylene based membrane of claim 1 comprising (a) preparing an organic solution of perylene compound, wherein said organic solvent is miscible in water; (b) adding excess of water to said solution of (a); wherein the ratio between said organic solvent to water is between about 3:97% to 8:92% v/v; (c) evaporating said organic solvent; and (d) transferring said aqueous solution or emulsion of (c) through a solid support to obtain a noncovalent self-assembled perylene based membrane.

20. The method of claim 19, wherein organic solvent is tetrahydrofurane (THF), dimethylacetamide (DMA), dimethylformamide (DMF), acetonitrile, acetone, methanol, or ethanol.

21. The method of claim 19, wherein said solid support is a microfiltration filter comprising cellulose acetate (CA), teflon (PTFE) or polycarbonate, or microfiltration filter with pores smaller or equal to 0.45 microns.

22. A biocatalytic membrane comprising a noncovalent self-assembled porous membrane comprising a perylene diimide supramolecular structure and an enzyme; wherein said enzyme is immobilized within said membrane; wherein said noncovalent self-assembled perylene diimide comprises a perylene, a salt thereof or a metal thereof as a monomeric unit represented by the structure of formula I:

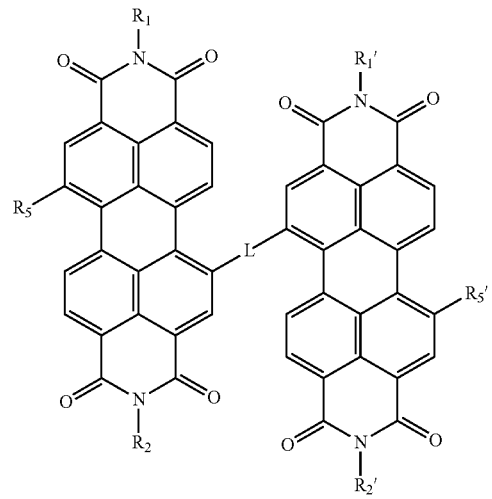

wherein
$R_1$ and $R_1'$ are independently $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $[(alkylene)_nO]_oCH_3$, $[(alkylene)_nC(O)O]_oCH_3$, $[(alkylene)_nC(O)NH]_oCH_3$, $[(alkylene)_nCH_2=CH_2]_oCH_3$, $[(alkylene)_nCH=CH]_oCH_3$, $[(alkylene)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)NHR_3NH]_pH$ wherein said aryl or heteroaryl groups are optionally substituted by 1-3 groups selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, $O(C_1-C_8)$alkyl or $(C_1-C_8)$alkyl; and wherein $R_3$ in said $[C(O)NHR_3NH]_pH$ is an alkyl, haloalkyl, hydroxyalkyl, hydroxyl, aryl, phenyl, alkylphenyl, alkylamino and independently the same or different when p is larger than 1;

$R_2$ and $R_2'$ are independently $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_qO]_rCH_3$, $[(alkylene)_qC(O)O]_rCH_3$, $[(alkylene)_qC(O)NH]_rCH_3$, $[(alkylene)_qCH_2=CH_2]_rCH_3$, $[(alkylene)_qCH=CH]_rCH_3$, $[(alkylene)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)NHR_4NH]_sH$ wherein said aryl or heteroaryl groups are optionally substituted by 1-3 groups selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)NHR_4NH]_sH$ is an alkyl, haloalkyl, hydroxyalkyl, hydroxyl, aryl, phenyl, alkylphenyl, alkylamino and independently the same or different when s is larger than 1;

$R_5$ and $R_5'$ are independently H, —$OR_x$ where $R_x$ is $C_1-C_6$ alkyl or $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $[(alkylene)_q$ O]$_r$CH$_3$, [(alkylene)$_q$C(O)O]$_r$CH$_3$, [(alkylene)$_q$C(O)NH]$_r$CH$_3$, [(alkylene)$_q$CH$_2$=CH$_2$]$_r$CH$_3$, [(alkylene)$_q$CH=CH]$_r$CH$_3$, [(alkylene)$_q$NH]$_r$CH$_3$, aryl, heteroaryl, C≡C—R$_7$, CH=CR$_8$R$_9$, NR$_{10}$R$_{11}$, amino acid, peptide or a saturated carbocyclic or heterocyclic ring wherein said saturated heterocyclic ring or heteroaryl contains at least one nitrogen atom and R$_5$ or R$_5$' are connected via the nitrogen atom and wherein said saturated carbocyclic ring, heterocyclic ring, aryl and heteroaryl groups are optionally substituted by 1-3 groups selected from halide, aryl, heteroaryl, CN, CO$_2$H, OH, SH, NH$_2$, CO$_2$—(C$_1$-C$_6$ alkyl), and O—(C$_1$-C$_6$ alkyl);

R$_7$ is H, halo, (C$_1$-C$_{32}$)alkyl, aryl, NH$_2$, alkyl-amino, COOH, C(O)H, alkyl-COOH heteroaryl, Si(H)$_3$ or Si[(C$_1$-C$_8$)alkyl]$_3$ wherein said aryl or heteroaryl groups are optionally substituted by 1-3 groups selected from halide, aryl, heteroaryl, CN, CO$_2$H, OH, SH, NH$_2$, CO$_2$—(C$_1$-C$_6$ alkyl), and O—(C$_1$-C$_6$ alkyl);

R$_8$, R$_9$, R$_{10}$ and R$_{11}$ are independently H, (C$_1$-C$_{32}$)alkyl, aryl, NH$_2$, alkyl-amino, COOH, C(O)H, alkyl-COOH or heteroaryl wherein said aryl or heteroaryl groups are optionally substituted by 1-3 groups selected from halide, CN, CO$_2$H, OH, SH, NH$_2$, CO$_2$—(C$_1$-C$_6$ alkyl), and O—(C$_1$-C$_6$ alkyl);

L is a linker;
n is an integer from 1-5;
o is an integer from 1-100;
p is an integer from 1-100;
q is an integer from 1-5;
r is an integer from 1-100; and
s is an integer from 1-100;
wherein if R$_5$ and R$_5$' independently are amino acid or peptide; said membrane will form a chiral membrane.

23. The biocatalytic membrane of claim 22, wherein said noncovalent self-assembled perylene comprises a perylene represented by the structure of formula III, IV or V:

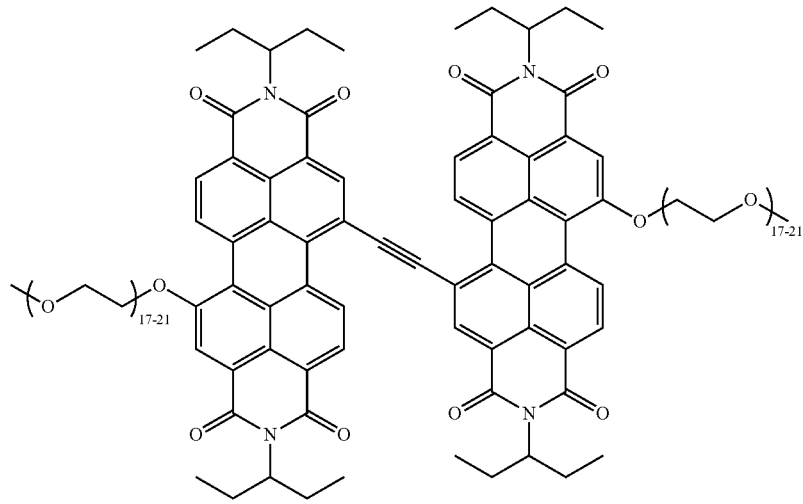

Perylene III

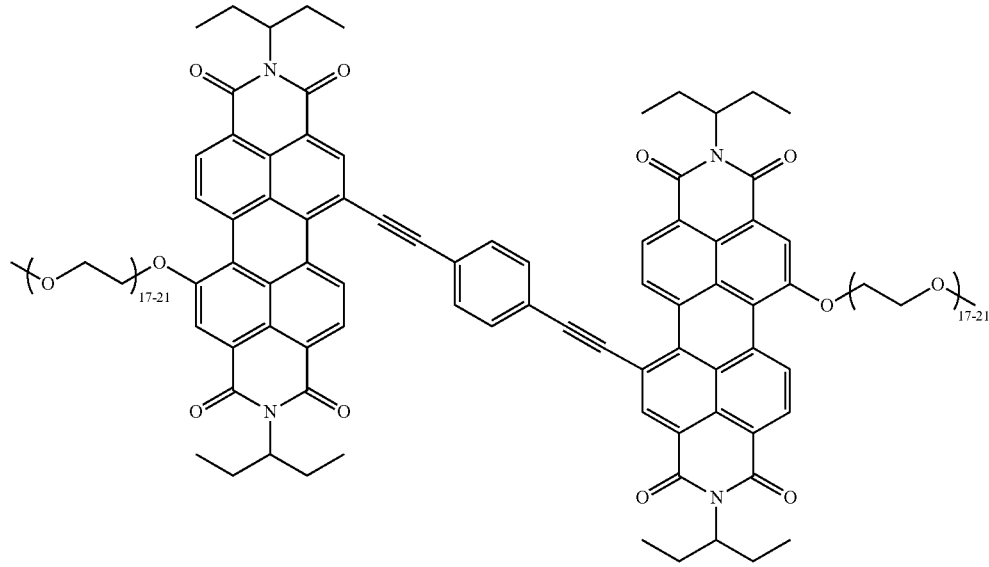

Perylene IV

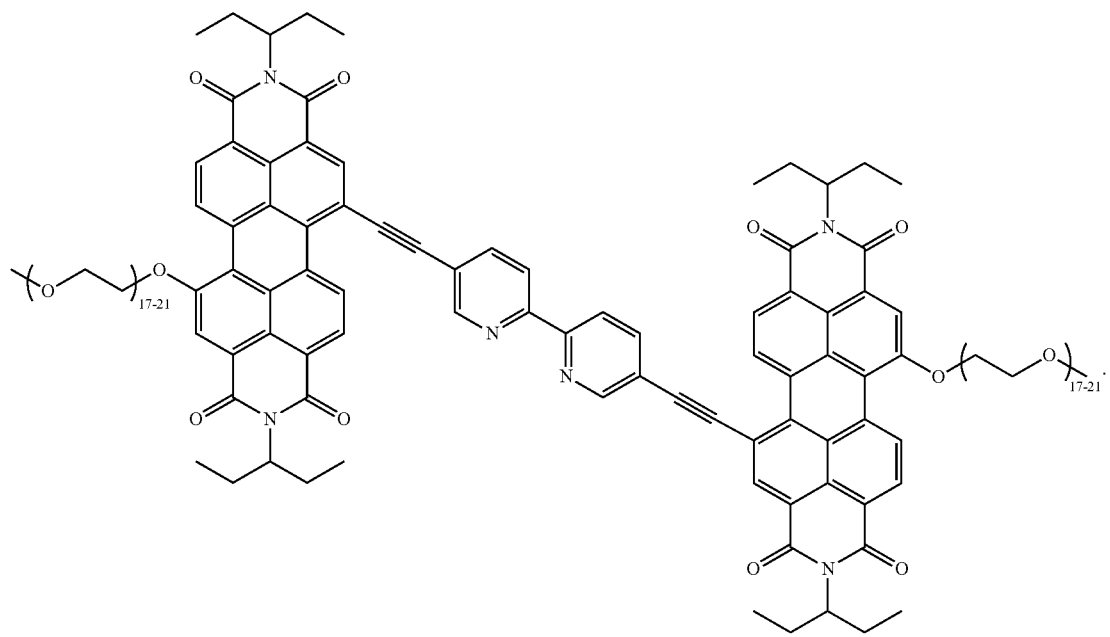

Perylene V

24. The biocatalytic membrane of claim 22, wherein said enzyme is larger than the membrane cutoff.

25. The biocatalytic membrane of claim 22, wherein said enzyme is β Galactosidase; and said β Galactosidase catalyzes conversion of ortho-nitrophenyl-β-galactoside (ONPG) into galactose and o-nitophenol (ONP).

26. The biocatalytic membrane of claim 22, wherein said enzyme is hexameric CS; and said hexameric CS catalyzes conversion of oxaloacetate into citrate in the presence of a coenzyme.

* * * * *